(12) United States Patent
Nagai et al.

(10) Patent No.: US 7,790,885 B2
(45) Date of Patent: Sep. 7, 2010

(54) PROCESS FOR PREPARING PHENOXYPYRIDINE DERIVATIVES

(75) Inventors: Mitsuo Nagai, Tsukuba (JP); Tomohiro Matsushima, Tsukuba (JP); Atsushi Kamada, Tsukuba (JP); Kazunori Wakasugi, Tsukuba (JP); Shuji Shirotori, Tsukuba (JP); Shinya Abe, Tsukuba (JP); Kazumasa Nara, Tsukuba (JP); Takahisa Sakaguchi, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 355 days.

(21) Appl. No.: 11/892,785

(22) Filed: Aug. 27, 2007

(65) Prior Publication Data

US 2008/0214815 A1    Sep. 4, 2008

Related U.S. Application Data

(60) Provisional application No. 60/824,192, filed on Aug. 31, 2006, provisional application No. 60/855,117, filed on Oct. 30, 2006.

(30) Foreign Application Priority Data

Oct. 19, 2006    (JP) .............................. 2006-285327

(51) Int. Cl.
  *C07D 239/02*   (2006.01)
  *C07D 213/00*   (2006.01)
  *C07D 213/81*   (2006.01)
(52) U.S. Cl. .................. 544/297; 546/323; 546/309
(58) Field of Classification Search .................. 544/297; 546/323, 309
See application file for complete search history.

(56) References Cited

U.S. PATENT DOCUMENTS

| | | | |
|---|---|---|---|
| 6,790,852 | B2 | 9/2004 | Brandt et al. |
| 7,531,532 | B2 | 5/2009 | Matsushima et al. |
| 2003/0199691 | A1 | 10/2003 | Brandt et al. |
| 2004/0053908 | A1 | 3/2004 | Funahashi et al. |
| 2004/0214874 | A1 | 10/2004 | Brandt et al. |
| 2004/0242603 | A1 | 12/2004 | Fujiwara et al. |
| 2005/0009840 | A1 | 1/2005 | Cui et al. |
| 2005/0014753 | A1 | 1/2005 | Ding et al. |
| 2005/0245530 | A1 | 11/2005 | Borzilleri et al. |
| 2005/0277652 | A1 | 12/2005 | Matsushima et al. |
| 2006/0252777 | A1 | 11/2006 | Kim et al. |
| 2008/0214815 | A1 | 9/2008 | Nagai et al. |
| 2008/0318924 | A1 | 12/2008 | Matsushima et al. |
| 2008/0319188 | A1 | 12/2008 | Matsushima et al. |
| 2009/0227556 | A1 | 9/2009 | Obaishi |

FOREIGN PATENT DOCUMENTS

| | | |
|---|---|---|
| EP | 1411046 A1 | 4/2004 |
| EP | 1415987 A1 | 5/2004 |
| EP | 1473043 A1 | 11/2004 |
| EP | 1506962 A2 | 2/2005 |
| EP | 1719762 A1 | 11/2006 |
| EP | 1719763 A1 | 11/2006 |
| EP | 1 889 836 A1 | 2/2008 |
| JP | 2007-153894 | 6/2007 |
| JP | 2007-153894 A | 6/2007 |
| WO | WO-02/32872 A1 | 4/2002 |
| WO | WO-02/096361 A2 | 12/2002 |
| WO | WO-03/000660 A1 | 1/2003 |
| WO | WO-03/087026 A1 | 10/2003 |
| WO | WO-03/099771 A2 | 12/2003 |
| WO | WO-2004/076412 A2 | 9/2004 |
| WO | WO-2004/089286 A2 | 10/2004 |
| WO | WO-2005/004607 A1 | 1/2005 |
| WO | WO-2005-004808 A2 | 1/2005 |
| WO | WO-2005/005378 A2 | 1/2005 |
| WO | WO-2005/005389 A2 | 1/2005 |
| WO | WO-2005/010005 A1 | 2/2005 |
| WO | WO-2005/016920 A1 | 2/2005 |
| WO | WO-2005/030140 A2 | 4/2005 |
| WO | WO-2005/040154 A1 | 5/2005 |
| WO | WO-2005/082854 A1 | 9/2005 |
| WO | WO-2005/082855 A1 | 9/2005 |
| WO | WO-2005/117867 A2 | 12/2005 |
| WO | WO-2006/004636 A2 | 1/2006 |

| WO | WO-2006/014325 A2 | 2/2006 |
| WO | WO-2007/023768 A1 | 3/2007 |
| WO | WO-2008/102870 A1 | 8/2008 |

OTHER PUBLICATIONS

Hcaplus 2005:977021, "Preparation of pyridine and pyrimidine derivatives as inhibitors of hepatocyte growth factor receptor (HGFR)", Matsushima et. al., Sep. 9, 2005.*

Ulrich, J., Crystallization—4. Crystal Characteristics, Kirk-Othmer Encyclopedia of Chemical Technology, Aug. 2002.

Vippagunta et al., Crystalline Solids, Advanced Drug Delivery Reviews 48, pp. 3-26, 2001.

West, Solid Solutions, Solid State Chemistry and its applications, pp. 358 & 365, 1988.

Nakagawa et al., Proceedings of the American Association for Cancer Research, No. 4845, vol. 49, pp. 1154, (2008).

Obaishi et al., Proceedings of the American Association for Cancer Research, No. 4846, vol. 49, pp. 1154, (2008).

Nakagawa et al., Proceedings of the American Association for Cancer Research, No. 4845(Poster Manuscript), vol. 49, pp. 1154, (2008).

Obaishi et al., Proceedings of the American Association for Cancer Research, No. 4846(Poster Manuscript), vol. 49, pp. 1154, (2008).

'MET tyrosine kinase inhibitors. Nature Reviews Drug Discovery, vol. 7,p. 469 (2008).

Christine Ting Ting to et al.; Oncology Reports 5: 1013-1024, 1998.

Eliot M. Rosen et al.; Advances in Cancer Research, 67, 257-279, 1995.

N. Maehara et al.; British Journal of Cancer, 84, 864-873, 2001.

Kunio Matsumomto et al.; Cancer Sci., 94, 321-327, 2003.

Matthias Ebert et al.; Cancer Research; 54, pp. 5775-5778, Nov. 15, 1994.

Hiroki Kuniyasu et al.; Biochemical and Biophysical Research Communications; vol. 189, No. 1, pp. 227-232; Nov. 30, 1992.

Chi Liu et al.; Oncogene; 7, pp. 181-185, 1992.

Rola A. D. Ghoussoub et al.; Cancer, 82, pp. 1513-1520, 1998.

Louis L Pisters et al.; The Journal of Urology; vol. 154, pp. 293-298, Jul. 1995.

Iwao Takanami et al.: Oncology; 53; pp. 392-397, 1996.

Laura Schmidt et al.; Oncogene, 18, pp. 2343-2350, 1999.

Shahriar Koochekpour et al.; Cancer Research; 57; pp. 5391-5398, Dec. 1, 1997.

Janos Tanyi et al.; Pathology Oncology Research; vol. 5, No. 3; pp. 187-191, 1999.

Yoshitaka Imaizumi et al.; Clinical Cancer Research, 9, pp. 181-187, Jan. 2003.

Obaishi et al.. "E7050: A novel small molecule inhibitor of the c-Met and VEGFR-2 tyrosine kinases," Abstract of Presentation program of P1-7 in Japanese Association for Molecular Target Therapy of Cancer 2008, May 25, 2008.

Nakagawa et al., "E7050: a novel orally active c-Met and VEGFR-2 tyrosine kinase inhibitor exhibited potent antitumor effect and prolongation of survival in preclinical mice model," Abstract of Presentation program of P1-8 in Japanese Association for Molecular Target Therapy of Cancer 2008, May 25, 2008.

Kolibaba et al., "Protein tyrosine kinases and cancer", B. B. A., 1333, F217-F248, (Jul. 1997), Portland, OR.

Scheijen et al., "Tyrosine kinase oncogenes in normal hematopoiesis and hematological disease", Oncogene, 21, 3314-3333, (2002), Boston, MA.

Blume-Jensen et al., "Activation of the human c-kit product by ligand-induced dimerization mediates circular actin reorganization and chemotaxis", The EMBO Journal, 10, 4121-4128, (1991), Thousand Oaks, CA and Sweden.

Lev et al., "A specific combination of substrates is involved in signal transduction by the kit-encoded receptor" The EMBO Journal, 10, 647-654, (1991), Isreal.

Wang et al., "The Expression of the Proto-Oncogene C-Kit in the Blast Cells of Acute Myeloblastic Leukemia", Leukemia, 3, 699-702, (1989), Toronto, Canada and Cambridge, MA.

Kanakura et al., "Expression, Function and Activation of The Proto-oncogen c-kit Product in Human Leukemia Cells", Leukemia and Lymphoma, 10, 35-41, (1993), Osaka, Japan.

Ikeda et al., "Expression and Functional Role of the Proto-oncogene c-kit in Acute Myeloblastic Leukemia Cells", Blood, 78, 2962-2968, (1991).

Ikeda et al., "Changes in phenotype and proliferative potential of human acute myeloblastic leukemia cells in culture with stem cell factor", Experimental Hematology, 21, 1686-1694, (Aug. 1993), Osaka, Japan.

Furitsu et al., "Identification of Mutations in the Coding Sequence of the Proto-oncogene c-kit in a Human Mast Cell Leukemia Cell Line Causing Ligand-independent Activation of c-kit Product", J. Clin. Invest., 92, 1736-1744, (1993), Osaka, Japan; Rochester, MN and Adelaide, South Australia.

Hibi et al., "Coexpression of the stem cell factor and the c-kit genes in small-cell lung cancer", Oncogene, 6, 2291-2296, (1991), Nagoya, Japan.

Sekido et al., "Preferential Expression of c-kit Protooncogene Transcripts in Small Cell Lung Cancer", Cancer Research, 51, 2416-2419, (May 1, 1991), Nagoya, Japan.

Lasota et al., "Mutations in Exons 9 and 13 of KIT Gene Are Rare Events in Gastrointestinal Stromal Tumors", American Journal of Pathology, 157, 1091-1095, (Oct. 2000), Washington, D.C.; Helsinki, Finland and Krakow, Poland.

Taniguchi et al., Éffect of c-kit Mutation on Prognosis of Gastrointestinal Stromal Tumors, Cancer Research, 59, 4297-4300, (Sep. 1, 1999), Japan.

Strohmeyer et al., "Expression of the hst-1 and c-kit Protooncogenes in Human Testicular Germ Cell Tumors", Cancer Research, 51, 1811-1816, (Apr. 1, 1991), CA and Germany.

Tian et al., "Activating c-kit Gene Mutations in Human Germ Cell Tumors", American Journal of Pathology, 154, 1643-1647, (Jun. 1999), VA.

Tonary et al., "Lack of Expression of c-Kit in Ovarian Cancers is Associated With Poor Prognosis", Int. J. Cancer (Pred. Oncol.), 89, 242-250, (2000), Ottawa, Canada.

Natali et al., "Breat Cancer is Associated With Loss of the c-kit Ikit Oncogene Product". Int. J. Cancer, 52, 713-717, 1992, Rome, Italy.

Hines et al., "Coexpression of the c-kit and Stem Cell Factor Genes in Breast Carcinomas", Cell Growth & Differentiation, 6, 769-779, (Jun. 1995), Richmond, VA.

Berdel et al., "Recombinant Human Stem Cell Factor Stimulates Growth of a Human Glioblastoma Cell Line Expressing c-kit Protooncogene", Cancer Research, 52, 3498-3502, (Jun. 15, 1992), Germany.

Cohen et al., "Expression of Stem Cell Factor and c-kit in Human Neuroblastoma", Blood, 84, 3465-3472, (1994).

Bellone et al., "Growth Stimulation of Colorectal Carcinoma Cells Via the c-Kit Receptor is Inhibited by TGF-β1", Journal of Cellular Physiology, 172, 1-11, (1997), Torino, Italy and Philadelphia, PA.

Hamel et al., "The road less travelled: c-kit and stem cell factor", Journal of Neuro-Oncology, 35, 327-333, (1997), Hamburg, Germany and San Francisco, CA.

Kitamura et al., "Regulation of Development, Survival and Neoplastic Growth of Mast Cells through the c-kit Receptor", Int. Arch. Allergy Immunol., 107, 54-56, (1995), Osaka, Japan.

Metcalfe, "Classification and Diagnosis of Mastocytosis: Current Status", J. Invest. Derm., 96, 2S-4S, (1991), Bethesda, MD.

Golkar et al., "Mastocytosis", The Lancet, 349, 1379-1385, (1997).

Nagata et al., "Elevated expression of the proto-oncogene c-kit in patients with mastocytosis", Leukemia, 12, 175-181, (1998), Bethesda, MD.

Longley et al., "Altered Metabolims of Mast-Cell Growth Factor (c-kit Ligand) in Cutaneous Mastocytosis", New England Journal of Medicine, 328, 1302-1307, (May 6, 1993).

Longley et al., "Somatic c-Kit activating mutation in urticaria pigmentosa and aggressive mastocytosis: establishment of clonality in a human mast cell neoplasm", Nature Genetics, 12, 312-314, (Mar. 1996).

Thomas et al., "The Eosinophil and its Role in Asthma", Gen. Pharmac., 27, 593-597, (1996), Southampton, UK.

Metcalfe et al., "Mast Cells", Physiological Reviews, 77, 1033-1079, (Oct. 1997), Tel Aviv, Israel.

Naclerio et al., "Rhinitis and Inhalant Allergens", JAMA, 278, 1842-1848, (Dec. 10, 1997).

Meltzer, "The pharmacological basis for the treatment of perennial allergic rhinitis and non-allergic rhinitis with topical corticosteroids", Allergy, 52, 33-40, (1997), San Diego, CA.

Okayama et al., "Activation of Eosinophils with Cytokines Produced by Lung Mast Cells", International Archives of Allergy and Immunology, 114, 75-77, (1997), Maebashi, Japan; Southampton, UK and Adelaide, Australia.

Okayama et al., "Human lung mast cells are enriched in the capacity to produce granulocyte-macrophage colony-stimulating factor in response to IgE-dependent stimulation", Eur. J. Immunol., 28, 708-715, (1998), Maebashi, Japan, Adelaide, Australia and Southampton, GB.

Metcalf, "Lineage commitment in the progeny of murine hematopoietic preprogenitor cells: Influence of thrombopoietin and interleukin", Proc. Natl. Acad. Sci., 95, 6408-6412, (May 1998), Victoria, Australia.

Kay et al., "Eosinophils and Eosinophil-Associated Cytokines in Allergic Inflammation", International Archives of Allergy and Immunology, 113, 196-199, (1997), London, UK.

Hogaboam et al., "Novel Role of Transmembrane SCF for Mast Cell Activation and Eotaxin Production in Mast Cell-Fibroblast Interactions", The Journal of Immunology, 160, 6166-6171, Feb. 17, 1998), Ann Arbor, MI and Frederick, MD.

Luckas et al., "Stem Cell Factor (c-kit Ligand) Influences Eosinophil Recruitment and Histamine Levels in Allergic Airway Inflammation", The Journal of Immunology, 156, 3945-3951, Feb. 28, 1996, Ann Arbor, MI; Frederick, MD and New Haven, CT.

Folkman et al., "Angiogenesis", The Journal of Biological Chemistry, 267, 10931-10934, (1992), Boston, MA.

Jakeman et al., "Developmental Expression of Binding Sites and Messenger Ribonucleic Acis for Vascular Endothelial Growth Factor Suggests a Role for This Protein in Vasculogenesis and Angiogenesis", Endocrinology, 133, 848-859, (1993), San Francisco, CA.

Folkman, "Clinical Applications of Research on Angiogenesis", The New England Journal of Medicine, 333, 1757-1763, (Dec. 28, 1995).

Folkman, "What Is the Evidence That Tumors Are Angiogenesis Dependent?", Journal of the National Cancer Institute, 82, 4-6, (Jan. 3, 1990), Boston, MA.

Ferrara et al., "Molecular and Biological Properties of the Vascular Endothelial Growth Factor Family of Proteins", Endocrine Reviews, 13, 18-32, (1992), San Francisco, CA.

Plate et al., "Vascular endothelial growth factor is a potential tumour angiogenesis factor in human gliomas in vivo", Letter to Nature, 359, 845-848, (1992), Germany.

Plate et al., "Up-Regulation of Vascular Endothelial Growth Factor and Its Cognate Receptors in a Rat Glioma Model of Tumor Angiogenesis", Cancer Research, 53, 5822-5827, (Dec. 1, 1993), Germany.

Berkman et al., "Expression of the Vascular Permeability Factor/Vascular Endothelial Growth Factor Gene in Central Nervous System Neoplasms", The Journal of Clinical Investigation, 91, 153-159, (Jan. 1993), Bethesda, MD and Memphis, TN.

Nakamura et al., "Vascular Endothelial Growth Factor is a Potent Angiogenic Factor in AIDS-Associated Kaposi's Sarcoma-Derived Spindle Cells", The Journal of Immnology, 158, 4992-5001, (Feb. 12, 1997), Germany and CA.

Mustonen et al., "Endothelial Receptor Tyrosine Kinases Involved in Angiogenesis", The Journal of Cell Biology, 129, 895-898, (May 1995), Helsinki, Finland.

Bardella et al., "Truncated RON Tyrosine Kinase Drives Tumor Cell Progression and Abrogates Cell-Cell Adhesion Through E-Cadherin Transcriptional Repression", Cancer Research, 64, 5154-5161, (Aug. 1, 2004), Italy.

O'Toole et al., "Therapeutic Implications of a Human Neutralizing Antibody to the Macrophage-Stimulating Protein Receptor Tyrosine Kinase (RON), a c-MET Family Member", Cancer Research, 66, 9162-9170, (2006), Stonybrook, NY and Cincinnati, OH.

Carlomagno et al., "ZD6474, an Orally Available Inhibitor of KDR Tyrosine Kinase Activity, Efficiently Blocks Oncogenic RET Kinases", Cancer Research, 62, 7284-7290, (Dec. 15, 2002), Italy and UK.

Carlomagno et al., "BAY 43/9006 Inhibition of Oncogenic RET Mutants", Journal of National Cancer Institute, 98, 326-334, (Mar. 1, 2006).

Terman et al., "Identification of a new endothelial cell growth factor receptro tyrosine kinase", Oncogene, 6, 1677-1683, (1991), NY.

Park et al., "Homogeneous Proximity Tyrosine Kinase Assays: Scintillation Proximity Assay versus Homogeneous Time-Resolved Fluorescence", Analytical Biochemistry, 269, 94-104, (1999), Rahway, NJ.

"Cell Culture Technique", Lectures on New Biochemical Experiments, 18, 197-202, with English language translation.

Watson et al., "Inhibition of c-Met as a Therapeutic Strategy for Esophageal Adenocarcinoma," Neoplasia, vol. 8, No. 11, Nov. 2006, pp. 949-955.

English Translation of International Search Report and Written Opinion for PCT/IB2008/003880 issued Aug. 11, 2009.

Office Action dated Dec. 3, 2008 in related Russian patent application No. 2008110932, with English translation.

Office Action dated Nov. 5, 2007 in related patent application No. 184/2006/4959 in Bangladesh, in English.

Office Action (dated Oct. 21, 2008 and Dec. 12, 2007) in related patent application No. 1024/2006 in Pakistan, in English.

Office Action (dated Oct. 21, 2008) in related patent application No. 375/2008 in Pakistan, in English.

English translation of WO 2008/102870 published Aug. 28, 2008.

English translation of International Preliminary Report on Patentability (IPRP-Chapter I) issued in International Application No. PCT/JP2007/066185 dated Mar. 5, 2009 (6 pages).

Office Action issued Sep. 29, 2009 in corresponding Japanese Application No. 2006-510543.

Miller et al., "Genomic amplification of MET with boundaries within fragile site FRA7G and upregulation of MET pathways in esophageal adenocarcinoma", Oncogene, 2006, vol. 25, pp. 409-418.

Smolen et. al. "Amplification of MET may identify a subset of cancers with extreme sensitivity to the selective tyrosine kinase inhibitor PHA-665752" Proc. Nat. Acad. Sci. USA, 103(7): 2316-2321, 2006.

H. Saeki et al., "Concurrent overexpression of Ets-1 and c-Met correlates with a phenotype of high cellular motility in human esophageal cancer", International Journal of Cancer, vol. 98, No. 1, pp. 8-13, 2002.

U.S. Office Action mailed May 29, 2009 in U.S. Appl. No. 11/508,322.

U.S. Office Action mailed Dec. 18, 2008 in U.S. Appl. No. 11/508,322.

Berge et al., "Pharmaceutical Salts", Journal of Pharmaceutical Sciences, vol. 66, No. 1, pp. 1-19, Jan. 1977.

Naran et al., "Inhibition of HGF/MET as therapy for malignancy", Expert Opin. Ther. Targets, vol. 13, No. 5, pp. 569-581, 2009.

Office Action mailed Feb. 5, 2010 in co-pending U.S. Appl. No. 12/031,568.

* cited by examiner

*Primary Examiner*—Janet L Andres
*Assistant Examiner*—Binta M Robinson
(74) *Attorney, Agent, or Firm*—Birch, Stewart, Kolasch & Birch, LLP

(57) ABSTRACT

A process for preparing a compound represented by the formula (I):

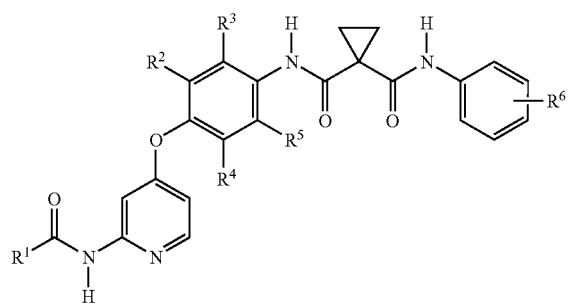

comprising reacting a compound represented by the formula (II) or salt thereof:

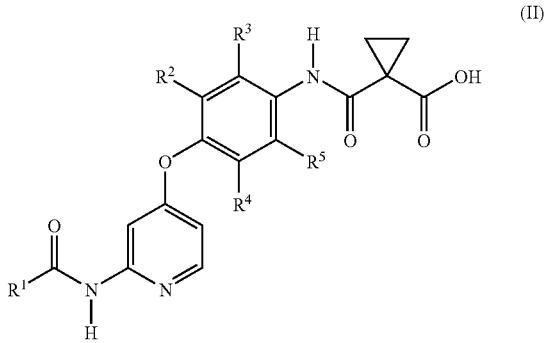

with a compound represented by the formula (III):

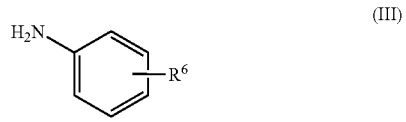

in the presence of a condensation reagent,
wherein $R^1$ represents 1) optionally substituted azetidin-1-yl, 2) optionally substituted pyrrolidin-1-yl, 3) optionally substituted piperidin-1-yl, etc.; $R^2$, $R^3$, $R^4$ and $R^5$ may be the same or different and each represents hydrogen or fluorine; and $R^6$ represents hydrogen or fluorine.

22 Claims, 1 Drawing Sheet

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: an artificially synthesized primer sequence

<400> SEQUENCE: 1
ccggccggat ccaaaaagag aaagcaaatt aaa                                33

<210> SEQ ID NO 2
<211> LENGTH: 33
<212> TYPE: DNA
<213> ORGANISM: Artificial Sequence
<220> FEATURE:
<223> OTHER INFORMATION: an artificially synthesized primer sequence

<400> SEQUENCE: 2
ttaattctgc agctatgatg tctcccagaa gga                                33
```

PROCESS FOR PREPARING PHENOXYPYRIDINE DERIVATIVES

RELATED APPLICATIONS

This application claims priority to U.S. Provisional Applications 60/824,192 filed on Aug. 31, 2006 and 60/855,117 filed on Oct. 30, 2006 as well as Japanese Patent Application 2006-285,327 filed on Oct. 19, 2006, all of which are herein incorporated by reference in their entirety.

BACKGROUND OF THE INVENTION

1. Field of the Invention

The present invention relates to processes for preparing phenoxypyridine derivatives (hereafter referred to as "the present compound") useful as an anti-tumor agent and an inhibitor for cancer metastasis having inhibitory activity against hepatocyte growth factor receptor (hereafter referred to as "HGFR"), anti-tumor activity, inhibitory activity against angiogenesis, inhibitory activity against cancer metastasis or the like, and to preparation intermediates in the processes.

2. Related Background Art

Overexpression of HGFR is reported in various kinds of tumors such as a pancreatic cancer, a gastric cancer, a colorectal cancer, a breast cancer, a prostate cancer, a lung cancer, a renal cancer, a brain tumor or an ovarian cancer (non-patent document 1). HGFR expressed in these cancer cells is considered to be involved in cancer malignancy (aberrant growth, invasion or enhanced metastasis), because HGFR cause autophosphorylation of intracellular tyrosine kinase constitutively or upon stimulation by hepatocyte growth factor (hereafter referred to as "HGF").

It is also reported that HGFR is expressed in vascular endothelial cells and is involved in tumor angiogenesis since HGF stimulates HGFR to facilitate proliferation and migration of vascular endothelial cells (non-patent document 2).

Furthermore, NK4, an antagonistic peptide for HGF, is reported to block HGF-HGFR signal to inhibit invasion of cancer cells and tumor angiogenesis (non-patent documents 3 and 4).

Therefore, a compound having inhibitory activity against HGFR is expected to be useful as an anti-tumor agent, an angiogenesis inhibitor or an inhibitor for cancer metastasis.

By the way, patent document 1 discloses compounds similar to the present compounds in structure and processes for preparing the same, but does not disclose the processes for preparing the present compounds according to the present invention and the preparation intermediates in the processes as well as the present compounds.

[Patent document 1] WO 2005/082855
[Non-patent document 1] Oncology Reports, 5, 1013-1024 (1998)
[Non-patent document 2] Advances in Cancer Research, 67, 257-279 (1995)
[Non-patent document 3] British Journal of Cancer, 84, 864-873 (2001)
[Non-patent document 4] Cancer Sci., 94, 321-327 (2003)

SUMMARY OF THE INVENTION

An object of the invention is to find processes for preparing phenoxypyridine derivatives having inhibitory activity against HGFR, anti-tumor activity, inhibitory activity against angiogenesis, inhibitory activity against cancer metastasis or the like, and preparation intermediates in the processes.

As a result of diligent studies in view of the above situation, the inventors have found processes for preparing phenoxypyridine derivatives suitable for industrial large scale synthesis, and preparation intermediates in the processes, and completed the invention.

Specifically, the present invention provides [1] to [21] below:

[1] A process for preparing a compound represented by the formula (I):

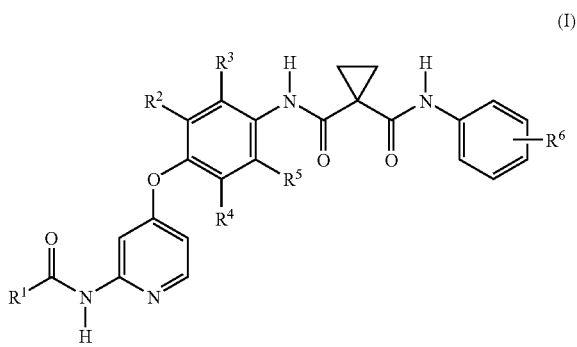

comprising reacting a compound represented by the formula (II) or salt thereof:

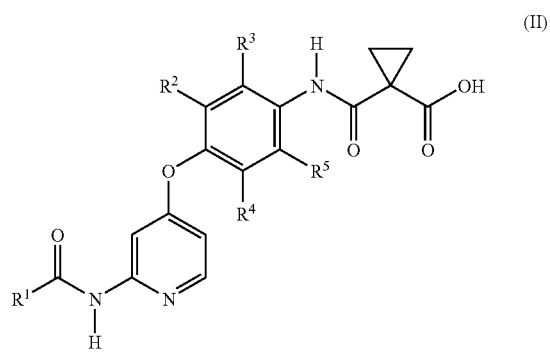

with a compound represented by the formula (III):

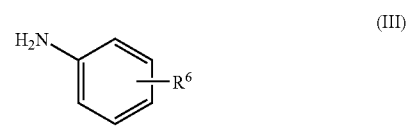

in the presence of a condensation reagent,
wherein $R^1$ represents 1) azetidin-1-yl optionally substituted with a substituent selected from Substituent Group A, 2) pyrrolidin-1-yl optionally substituted with a substituent selected from Substituent Group A, 3) piperidin-1-yl optionally substituted with a substituent selected from Substituent Group A, 4) piperazin-1-yl optionally substituted with a substituent selected from Substituent Group A, 5) diazepan-1-yl optionally substituted with a substituent selected from Substituent Group A, 6) morpholin-4-yl optionally substituted with a substituent selected from Substituent Group A, or 7)

—NR$^{11a}$R$^{11b}$, wherein R$^{11a}$ represents hydrogen or methyl, and R$^{11b}$ represents n-propyl, n-butyl, pyrrolidin-3-yl, piperidin-3-yl, piperidin-4-yl or tetrahydropyran-4-yl, and R$^{11b}$ may be substituted with a substituent selected from Substituent Group B;

R$^2$, R$^3$, R$^4$ and R$^5$ may be the same or different and each represents hydrogen or fluorine;

Substituent Group A consists of hydroxyl, dimethylaminoacetoxy, methyl, ethyl, dimethylamino, azetidinyl, pyrrolidinyl, piperidinyl and piperazinyl, where each group included in Substituent Group A other than hydroxyl and dimethylaminoacetoxy may be substituted with hydroxyl, methyl, dimethylamino, azetidinyl, pyrrolidinyl or piperidinyl;

Substituent Group B consists of methyl, ethyl, n-propyl, acetyl, dimethylamino, diethylamino, azetidinyl, pyrrolidinyl and piperazinyl, where each group included in Substituent Group B may be substituted with methyl or dimethylamino; and R$^6$ represents hydrogen or fluorine.

[2] The process according to [1], wherein the compound represented by the formula (II) or salt thereof:

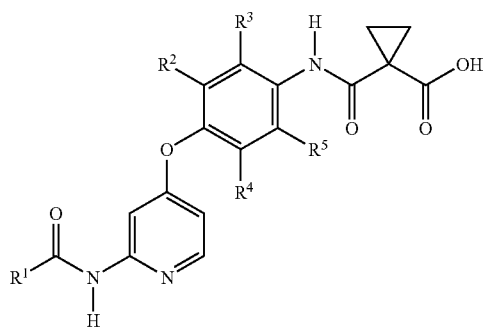

(II)

wherein R$^1$, R$^2$, R$^3$, R$^4$ and R$^5$ have the same definitions as defined in [1], is prepared by hydrolysis or catalytic hydrogenation of a compound represented by the formula (IV) or salt thereof:

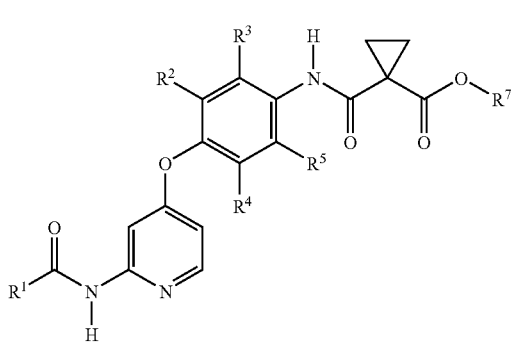

(IV)

wherein R$^1$, R$^2$, R$^3$, R$^4$ and R$^5$ have the same definitions as defined in [1], and R$^7$ represents C$_{1-6}$ alkyl or benzyl optionally substituted with one or two substituents selected from (1) halogen, (2) hydroxyl, (3) nitro, (4) cyano, (5) trifluoromethyl, (6) C$_{1-6}$ alkyl, (7) C$_{1-6}$ alkoxy, (8) amino, (9) mono-C$_{1-6}$ alkylamino and (10) di-C$_{1-6}$ alkylamino on the benzene ring.

[3] The process according to [2], wherein the compound represented by the formula (IV) or salt thereof:

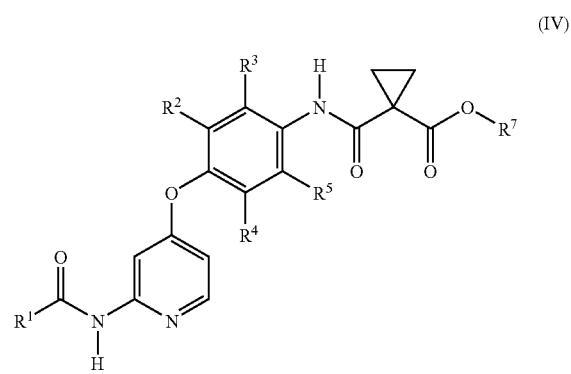

(IV)

wherein R$^1$, R$^2$, R$^3$, R$^4$ and R$^5$ have the same definitions as defined in [1], and R$^7$ has the same definition as defined in [2], is prepared by reacting a compound represented by the formula (V):

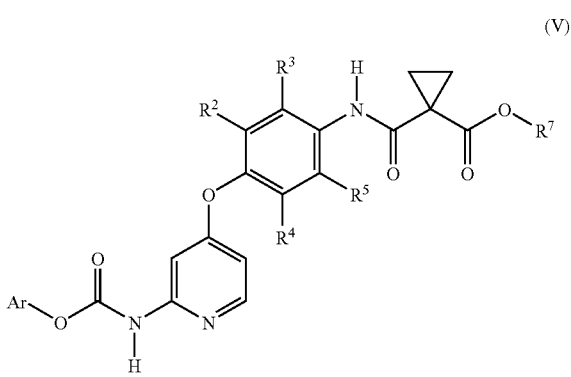

(V)

wherein R$^2$, R$^3$, R$^4$ and R$^5$ have the same definitions as defined in [1], R$^7$ has the same definition as defined in [2], and Ar represents phenyl optionally substituted with one or two substituents selected from halogen, methyl, methoxy, nitro, cyano and trifluoromethyl, with an amine or salt thereof selected from 1) azetidine optionally substituted with a substituent selected from Substituent Group A in [1], 2) pyrrolidine optionally substituted with a substituent selected from Substituent Group A in [1], 3) piperidine optionally substituted with a substituent selected from Substituent Group A in [1], 4) piperazine optionally substituted with a substituent selected from Substituent Group A in [1], 5) diazepane optionally substituted with a substituent selected from Substituent Group A in [1], 6) morpholine optionally substituted with a substituent selected from Substituent Group A in [1], or 7) HNR$^{11a}$R$^{11b}$, wherein R$^{11a}$ and R$^{11b}$ have the same definitions as defined in [1].

[4] The process according to [3], wherein the compound represented by the formula (V):

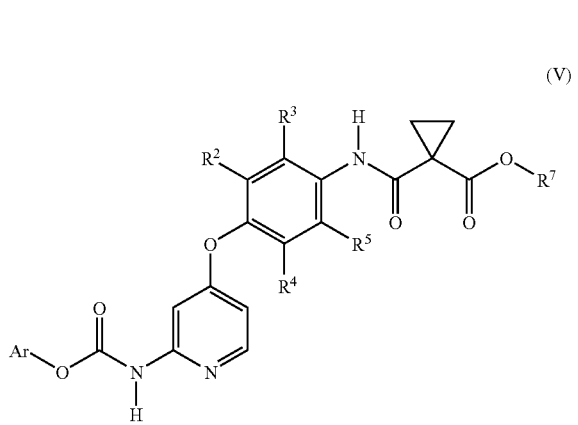

wherein $R^2$, $R^3$, $R^4$ and $R^5$ have the same definitions as defined in [1], $R^7$ has the same definition as defined in [2], and Ar has the same definition as defined in [3], is prepared by reacting a compound represented by the formula (VI):

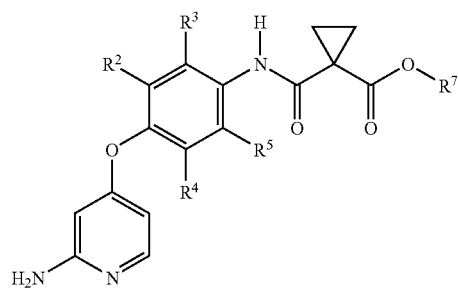

wherein $R^2$, $R^3$, $R^4$ and $R^5$ have the same definitions as defined in [1], and $R^7$ has the same definition as defined in [2], with a compound represented by the formula (VII):

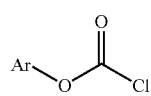

wherein Ar has the same definition as defined in [3], in the presence of a base.

[5] The process according to [4], wherein the compound represented by the formula (VI):

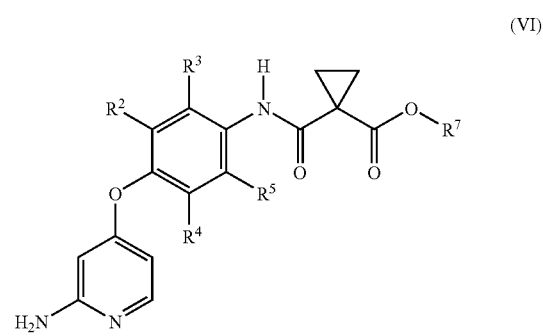

wherein $R^2$, $R^3$, $R^4$ and $R^5$ have the same definitions as defined in [1], and $R^7$ has the same definition as defined in [2], is prepared by reacting a compound represented by the formula (VIII):

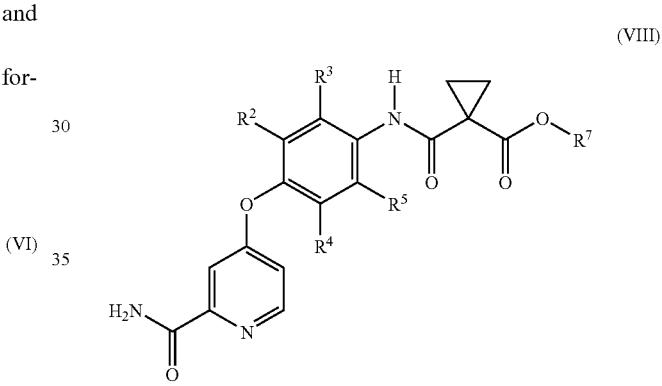

wherein $R^2$, $R^3$, $R^4$ and $R^5$ have the same definitions as defined in [1], and $R^7$ has the same definition as defined in [2], with a Hofmann rearrangement reagent.

[6] The process according to [5], wherein the compound represented by the formula (VIII):

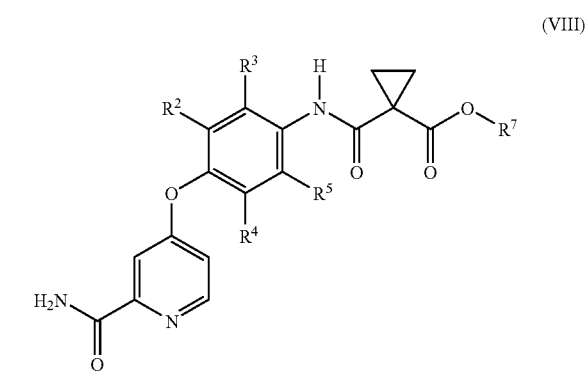

wherein $R^2$, $R^3$, $R^4$ and $R^5$ have the same definitions as defined in [1], and $R^7$ has the same definition as defined in [2], is prepared by reacting a compound represented by the formula (IX):

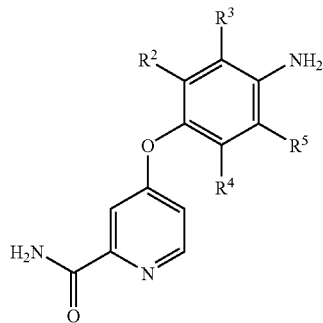

wherein $R^2$, $R^3$, $R^4$ and $R^5$ have the same definitions as defined in [1], with a compound represented by the formula (X):

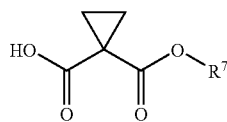

wherein $R^7$ has the same definition as defined in [2], in the presence of a halogenation reagent or a condensation reagent.

[7] The process according to [1] or [6], wherein the condensation reagent is 4-(4,6-dimethoxy[1.3.5]triazin-2-yl)-4-methylmorpholinium chloride hydrate or 2-chloro-4,6-dimethoxy-1,3,5-triazine.

[8] The process according to [3], wherein the amine is 1-(2-dimethylaminoethyl)piperazine, 4-(pyrrolidin-1-yl)piperidine, 4-(dimethylaminomethyl)piperidine, 4-(azetidin-1-yl)piperidine, N,N-dimethyl-N-[1-(piperidin-4-yl)azetidin-3-yl]amine, 1-methyl-4-(piperidin-4-yl)piperazine, 4-(1-methylpiperidin-4-yl)piperazine, 1-(1-methylazetidin-3-yl)piperazine, 4-(dimethylamino)piperidine, 4-(azetidin-1-ylmethyl)piperidine, 4-(pyrrolidin-1-ylmethyl)piperidine, (3S)-3-(dimethylamino)pyrrolidine, (3R)-3-(dimethylamino)pyrrolidine, azetidine, pyrrolidine, morpholine, 1-methylpiperazine, 3-hydroxyazetidine, 3-(azetidin-1-yl)azetidine, 3-(hydroxymethyl)azetidine, 3-(dimethylamino)azetidine, 3-(dimethylaminomethyl)azetidine, 4-hydroxypiperidine, 4-(hydroxymethyl)piperidine, (3R)-3-hydroxypyrrolidine, (3S)-3-hydroxypyrrolidine, 3-(azetidin-1-ylmethyl)azetidine, 3-(2-dimethylaminoacetoxy)azetidine, 1-methyl-4-(methylamino)piperidine, N-(1-ethylpiperidin-4-yl)-N-methylamine, N,N-dimethyl-N'-methylpropane-1,3-diamine or N,N-diethyl-N'-methylpropane-1,3-diamine.

[9] The process according to [5], wherein the Hofmann rearrangement reagent is iodobenzene diacetate or iodobenzene bis(trifluoroacetate).

[10] The process according to any one of [1] to [3], wherein $R^1$ is 4-[2-(dimethylamino)ethyl]piperazin-1-yl, 4-pyrrolidin-1-ylpiperidin-1-yl, 4-[(dimethylamino)methyl]piperidin-1-yl, 4-azetidin-1-ylpiperidin-1-yl, 4-[3-(dimethylamino)azetidin-1-yl]piperidin-1-yl, 4-(4-methylpiperazin-1-yl)piperidin-1-yl, 4-(1-methylpiperidin-4-yl)piperazin-1-yl, 4-(1-methylazetidin-3-yl)piperazin-1-yl, 4-(dimethylamino)piperidin-1-yl, 4-(azetidin-1-ylmethyl)piperidin-1-yl, 4-(pyrrolidin-1-ylmethyl)piperidin-1-yl, (3S)-3-(dimethylamino)pyrrolidin-1-yl, (3R)-3-(dimethylamino)pyrrolidin-1-yl, azetidin-1-yl, pyrrolidin-1-yl, morpholin-4-yl, 4-methylpiperazin-1-yl, 3-hydroxyazetidin-1-yl, 1,3'-biazetidin-1'-yl, 3-(hydroxymethyl)azetidin-1-yl, 3-(dimethylamino)azetidin-1-yl, 3-[(dimethylamino)methyl]azetidin-1-yl, 4-hydroxypiperidin-1-yl, 4-(hydroxymethyl)piperidin-1-yl, (3R)-3-hydroxypyrrolidin-1-yl, (3S)-3-hydroxypyrrolidin-1-yl, 3-(azetidin-1-ylmethyl)azetidin-1-yl, 3-(2-dimethylaminoacetoxy)azetidin-1-yl, methyl(1-methylpiperidin-4-yl)amino, (1-ethylpiperidin-4-yl)(methyl)amino, [3-(dimethylamino)propyl](methyl)amino or [3-(diethylamino)propyl](methyl)amino.

[11] The process according to any one of [1] to [6], wherein the group represented by the formula:

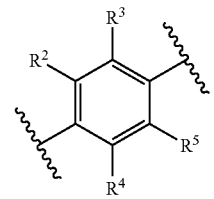

is a group represented by the formula:

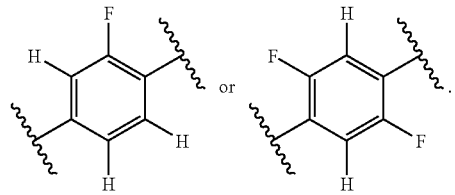

[12] The process according to any one of [2] to [6], wherein $R^7$ is benzyl.

[13] A compound represented by the formula (IV-1) or salt thereof:

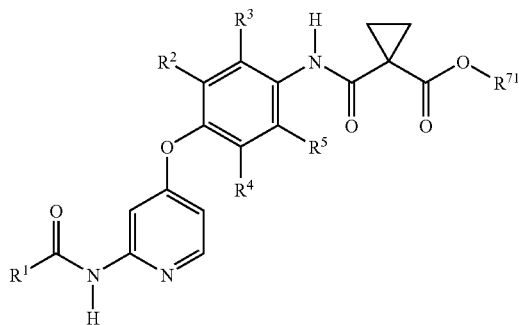

wherein $R^1$ represents 1) azetidin-1-yl optionally substituted with a substituent selected from Substituent Group A, 2) pyrrolidin-1-yl optionally substituted with a substituent selected from Substituent Group A, 3) piperidin-1-yl optionally substituted with a substituent selected from Substituent Group A, 4) piperazin-1-yl optionally substituted with a substituent selected from Substituent Group A, 5) diazepan-1-yl optionally substituted with a substituent selected from Substituent Group A, 6) morpholin-4-yl optionally substituted with a substituent selected from Substituent Group A, or 7) —NR$^{11a}$R$^{11b}$, wherein R$^{11a}$ represents hydrogen or methyl, and R$^{11b}$ represents n-propyl, n-butyl, pyrrolidin-3-yl, piperidin-3-yl, piperidin-4-yl or tetrahydropyran-4-yl, and R$^{11b}$ may be substituted with a substituent selected from Substituent Group B;

R$^2$, R$^3$, R$^4$ and R$^5$ may be the same or different and each represents hydrogen or fluorine;

R$^{71}$ represents hydrogen, C$_{1-6}$ alkyl or benzyl optionally substituted with one or two substituents selected from (1) halogen, (2) hydroxyl, (3) nitro, (4) cyano, (5) trifluoromethyl, (6) C$_{1-6}$ alkyl, (7) C$_{1-6}$ alkoxy, (8) amino, (9) mono-C$_{1-6}$ alkylamino and (10) di-C$_{1-6}$ alkylamino on the benzene ring;

Substituent Group A consists of hydroxyl, dimethylaminoacetoxy, methyl, ethyl, dimethylamino, azetidinyl, pyrrolidinyl, piperidinyl and piperazinyl, where each group included in Substituent Group A other than hydroxyl and dimethylaminoacetoxy may be substituted with hydroxyl, methyl, dimethylamino, azetidinyl, pyrrolidinyl or piperidinyl; and Substituent Group B consists of methyl, ethyl, n-propyl, acetyl, dimethylamino, diethylamino, azetidinyl, pyrrolidinyl and piperazinyl, where each group included in Substituent Group B may be substituted with methyl or dimethylamino.

[14] A compound represented by the formula (V) or salt thereof:

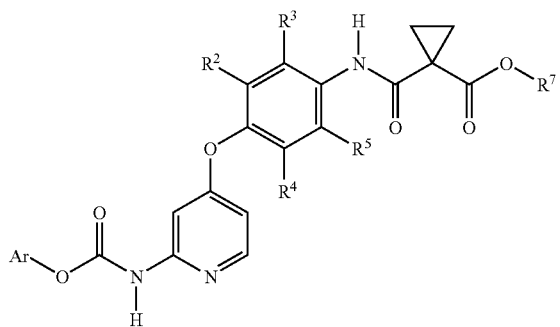

(V)

wherein R$^2$, R$^3$, R$^4$ and R$^5$ have the same definitions as defined in [13];

R$^7$ represents C$_{1-6}$ alkyl or benzyl optionally substituted with one or two substituents selected from (1) halogen, (2) hydroxyl, (3) nitro, (4) cyano, (5) trifluoromethyl, (6) C$_{1-6}$ alkyl, (7) C$_{1-6}$ alkoxy, (8) amino, (9) mono-C$_{1-6}$ alkylamino and (10) di-C$_{1-6}$ alkylamino on the benzene ring; and Ar represents phenyl optionally substituted with one or two substituents selected from halogen, methyl, methoxy, nitro, cyano and trifluoromethyl.

[15] A compound represented by the formula (VI) or salt thereof:

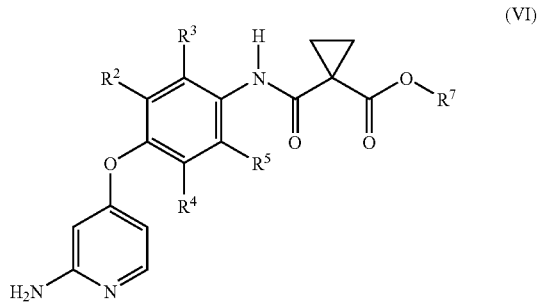

(VI)

wherein R$^2$, R$^3$, R$^4$ and R$^5$ have the same definitions as defined in [13], and R$^7$ has the same definition as defined in [14].

[16] A compound represented by the formula (VIII) or salt thereof:

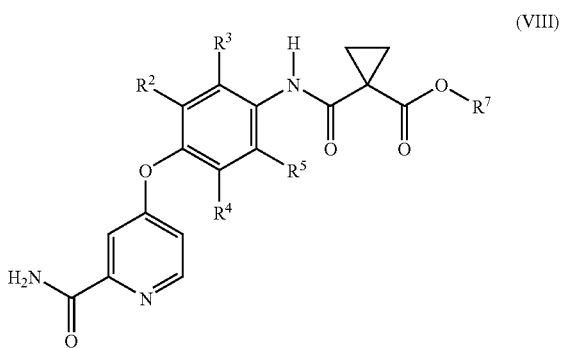

(VIII)

wherein R$^2$, R$^3$, R$^4$ and R$^5$ have the same definitions as defined in [13], and R$^7$ has the same definition as defined in [14].

[17] The compound or salt thereof according to [13], wherein R$^1$ is 4-[2-(dimethylamino)ethyl]piperazin-1-yl, 4-pyrrolidin-1-ylpiperidin-1-yl, 4-[(dimethylamino)methyl]piperidin-1-yl, 4-azetidin-1-ylpiperidin-1-yl, 4-[3-(dimethylamino)azetidin-1-yl]piperidin-1-yl, 4-(4-methylpiperazin-1-yl)piperidin-1-yl, 4-(1-methylpiperidin-4-yl)piperazin-1-yl, 4-(1-methylazetidin-3-yl)piperazin-1-yl, 4-(dimethylamino)piperidin-1-yl, 4-(azetidin-1-ylmethyl)piperidin-1-yl, 4-(pyrrolidin-1-ylmethyl)piperidin-1-yl, (3S)-3-(dimethylamino)pyrrolidin-1-yl, (3R)-3-(dimethylamino)pyrrolidin-1-yl, azetidin-1-yl, pyrrolidin-1-yl, morpholin-4-yl, 4-methylpiperazin-1-yl, 3-hydroxyazetidin-1-yl, 1,3'-biazetidin-1'-yl, 3-(hydroxymethyl)azetidin-1-yl, 3-(dimethylamino)azetidin-1-yl, 3-[(dimethylamino)methyl]azetidin-1-yl, 4-hydroxypiperidin-1-yl, 4-(hydroxymethyl)piperidin-1-yl, (3R)-3-hydroxypyrrolidin-1-yl, (3S)-3-hydroxypyrrolidin-1-yl, 3-(azetidin-1-ylmethyl)azetidin-1-yl, 3-(2-dimethylaminoacetoxy)azetidin-1-yl, methyl (1-methylpiperidin-4-yl)amino, (1-ethylpiperidin-4-yl)(methyl)amino, [3-(dimethylamino)propyl](methyl)amino or [3-(diethylamino)propyl](methyl)amino.

[18] The compound or salt thereof according to any one of [13] to [16], wherein the group represented by the formula:

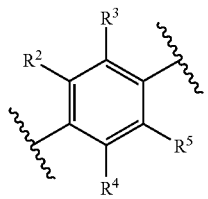

is a group represented by the formula:

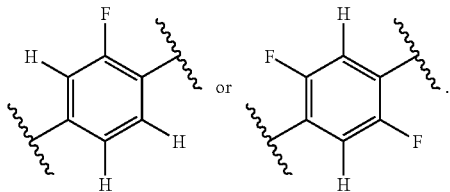

[19] The compound or salt thereof according to any one of [14] to [16], wherein $R^7$ is benzyl.

[20] A Crystal of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide.

[21] The crystal according to [20], having diffraction peaks at diffraction angles (2θ±0.2°) of 6.3°, 12.3° and 17.3° in a powder X-ray diffraction.

EFFECT OF THE INVENTION

The present invention provides processes for preparing phenoxypyridine derivatives having inhibitory activity against HGFR, anti-tumor activity, inhibitory activity against angiogenesis, inhibitory activity against cancer metastasis or the like, which are suitable for industrial large scale synthesis. The present invention also provides preparation intermediates useful in the processes.

DESCRIPTION OF THE PREFERRED EMBODIMENTS

Figure 1:
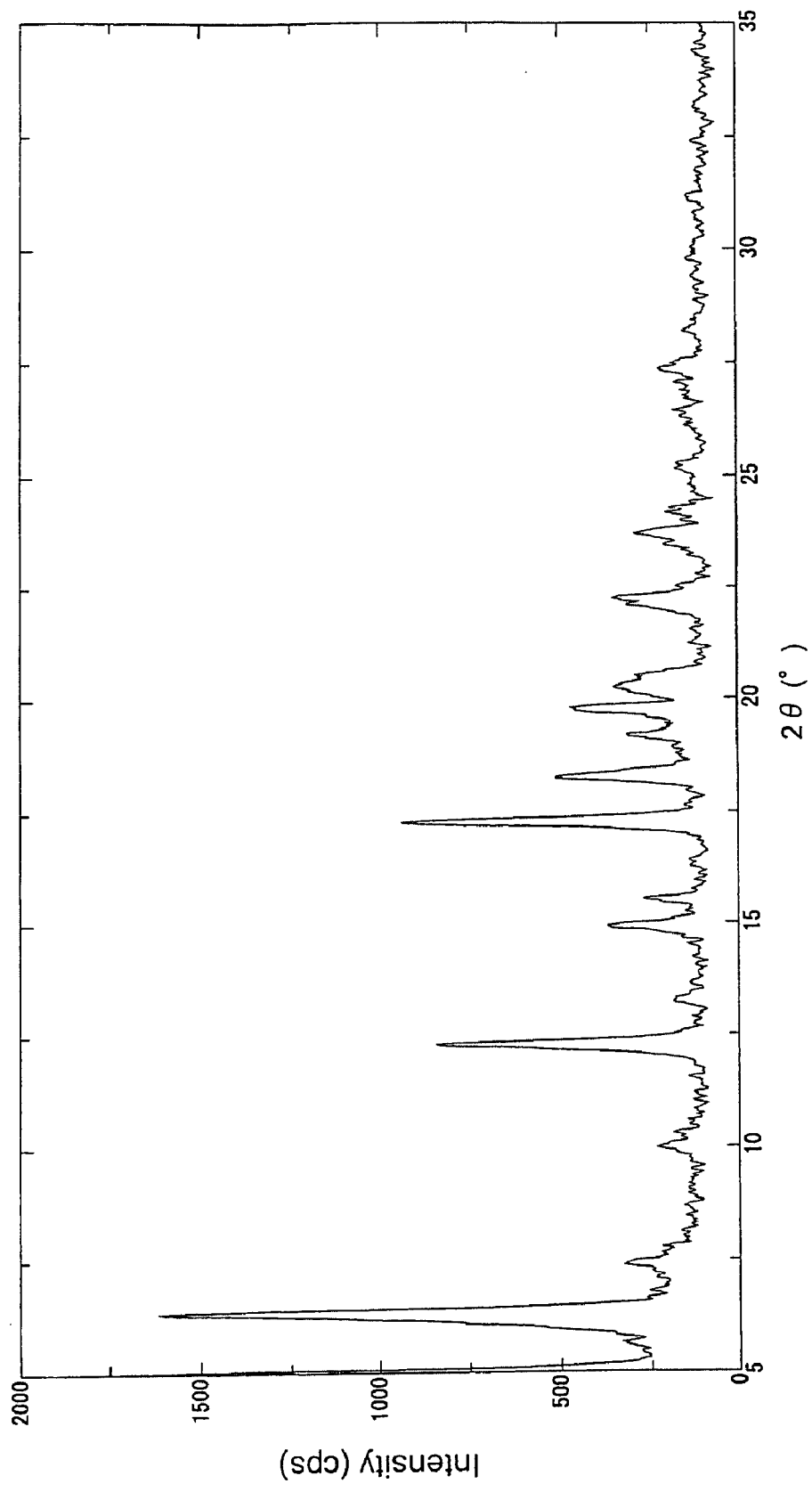
FIG. 1 represents a powder X-ray diffraction pattern for the crystals obtained in Example 9 (Method 3).

The symbols and terms as used herein will be defined below and the present invention will be described in details.

Several of the structural formulas for the compounds throughout the present specification represent only one isomeric form for convenience, but the invention encompasses any and all of the geometric isomers as well as optical isomers based on asymmetric carbons, stereoisomers and tautomers, and mixtures of those isomers, which are implied by the structures of the compounds, without being limited to any of the formulas shown for convenience. The compounds of the invention therefore include all those having asymmetric carbons therein and existing in optically active or racemic form, with no particular restrictions on the invention. There are also no restrictions when polymorphic crystalline forms thereof exist, and the compounds may be in one crystalline form or a mixture of different crystalline forms, while anhydrates and hydrates of the compounds of the invention are also included.

The "salt" is not particularly limited so long as it can form a salt with the compound according to the present invention and includes, for example, a salt with an inorganic acid, a salt with an organic acid, a salt with an inorganic base, a salt with an organic base, a salt with an acidic or basic amino acid or the like.

The preferable salt with an inorganic acid includes, for example, a salt with hydrochloric acid, hydrobromic acid, sulfuric acid, nitric acid, phosphoric acid or the like. The preferable salt with an organic acid includes, for example, a salt with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid or the like.

The preferable salt with an inorganic base includes, for example, an alkali metal salt such as sodium salt and potassium salt, an alkali earth metal salt such as calcium salt and magnesium salt, aluminum salt, ammonium salt or the like. The preferable salt with an organic base includes, for example, a salt with diethylamine, diethanolamine, meglumine, N,N-dibenzylethylenediamine or the like.

The preferable salt with an acidic amino acid includes, for example, a salt with aspartic acid, glutamic acid or the like. The preferable salt with a basic amino acid includes, for example, a salt with arginine, lysine, ornithine or the like.

The "halogen" represents fluorine, chlorine, bromine or iodine.

The "$C_{1-6}$ alkyl" represents an alkyl of straight or branched chain having a carbon number of 1 to 6, and includes, for specific example, methyl, ethyl, 1-propyl (n-propyl), 2-propyl (i-propyl), 2-methyl-1-propyl (i-butyl), 2-methyl-2-propyl (t-butyl), 1-butyl (n-butyl) and 2-butyl (s-butyl).

The "$C_{1-6}$ alkoxy" represents a group obtained by adding oxygen to the terminal of the above defined "$C_{1-6}$ alkyl", and includes, for specific example, methoxy, ethoxy, 1-propoxy (n-propoxy), 2-propoxy (1-propoxy), 2-methyl-1-propoxy (i-butoxy), 2-methyl-2-propoxy (t-butoxy), 1-butoxy (n-butoxy), 2-butoxy (s-butoxy) or the like.

The "mono-$C_{1-6}$ alkylamino" represents a group obtained by substituting one hydrogen of amino with the above defined "$C_{1-6}$ alkyl", and includes, for specific example, methylamino, ethylamino, 1-propylamino (n-propylamino), 2-propylamino (i-propylamino), 2-methyl-1-propylamino (1-butylamino), 2-methyl-2-propylamino (t-butylamino), 1-butylamino (n-butylamino), 2-butylamino (s-butylamino) or the like.

The "di-$C_{1-6}$ alkylamino" represents a group obtained by substituting two hydrogen of amino with the same or different groups of the above defined "$C_{1-6}$ alkyl", and includes, for specific example, N,N-dimethylamino, N,N-diethylamino, N,N-di-n-propylamino, N,N-di-i-propylamino, N,N-di-n-butylamino, N,N-di-1-butylamino, N,N-di-s-butylamino, N,N-di-t-butylamino, N-ethyl-N-methylamino, N-n-propyl-N-methylamino, N-i-propyl-N-methylamino, N-n-butyl-N-methylamino, N-i-butyl-N-methylamino, N-s-butyl-N-methylamino, N-t-butyl-N-methylamino or the like.

The "condensation reagent" in the above [1] and [6] represents 4-(4,6-dimethoxy[1.3.5]triazin-2-yl)-4-methylmorpholinium chloride hydrate, 2-chloro-4,6-dimethoxy-1,3,5-triazine, 2,4,6-trichloro-1,3,5-triazine, dicyclohexyl carbodiimide (DCC), 1-ethyl-3,(3'-dimethylaminopropyl) carbodiimide HCl salt (EDC or WSC HCl), O-(1H-benzothiazol-1-yl)-N,N,N',N'-tetramethyluronium hexafluorophosphate (HBTU), O-(1H-benzothiazol-1-yl)-N,N,N',N'-tetramethyluronium tetrafluoroborate (TBTU) or the like, and 4-(4,6-dimethoxy[1.3.5]triazin-2-yl)-4-methylmorpholinium chloride hydrate or 2,4,6-trichloro-1,3,5-triazine is preferable.

The "base" in the above [3] represents potassium carbonate, sodium carbonate, pyridine, triethylamine, diisopropylethylamine or the like, and potassium carbonate is preferable.

The "salt" of the "amine or salt thereof" in the above [3] is not particularly limited so long as it can form salt with amine, and includes, for example, a salt with hydrochloric acid, acetic acid, trifluoroacetic acid or the like.

The "base" in the above [4] represents pyridine, triethylamine, diisopropylethylamine, potassium carbonate, sodium carbonate or the like, and pyridine is preferable.

The "Hofmann rearrangement reagent" in the above [5] represents iodobenzene diacetate, iodobenzene bis(trifluoroacetate), sodium hypochlorite, potassium hypobromite, bromine, iodine or the like, and iodobenzene diacetate or iodobenzene bis(trifluoroacetate) is preferable.

The "halogenation reagent" in the above [6] represents thionyl chloride, oxalyl chloride, phosphorus trichloride, phosphorus oxychloride, phosphorus pentachloride or the like, and thionyl chloride is preferable.

The crystal of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide has diffraction peaks at diffraction angles (2θ±0.2°) of 6.3°, 12.3° and 17.3° in a powder X-ray diffraction, and preferably has diffraction peaks of 6.3°, 12.3°, 17.3°, 18.3°, 18.4°, 19.2°, 19.8°, 20.0°, 20.1°, 20.2°, 22.1° and 23.7°.

As for a diffraction angle (2θ) in the powder X-ray diffraction analysis, errors in the diffraction angle, generally, may occur within the range of ±0.2°. It is, therefore, to be understood that the values of the diffraction angles may include numerals on the order of ±0.2°. Accordingly, this invention encompasses not only crystal having completely matching diffraction angles of the peaks in powder X-ray diffraction, but also crystal having matching diffraction angles of the peaks within the errors of about ±0.2°.

The respective substituents of the compound represented by the above formula (I) according to the present invention will be described.

[The Definition of $R^1$]

$R^1$ represents 1) azetidin-1-yl optionally substituted with a substituent selected from Substituent Group A below, 2) pyrrolidin-1-yl optionally substituted with a substituent selected from Substituent Group A below, 3) piperidin-1-yl optionally substituted with a substituent selected from Substituent Group A below, 4) piperazin-1-yl optionally substituted with a substituent selected from Substituent Group A below, 5) diazepan-1-yl optionally substituted with a substituent selected from Substituent Group A below, 6) morpholin-4-yl optionally substituted with a substituent selected from Substituent Group A below, or 7) —NR$^{11a}$R$^{11b}$, wherein R$^{11a}$ represents hydrogen or methyl, and R$^{11b}$ represents n-propyl, n-butyl, pyrrolidin-3-yl, piperidin-3-yl, piperidin-4-yl or tetrahydropyran-4-yl, and R$^{11b}$ may be substituted with a substituent selected from Substituent Group B below.

Preferable examples of $R^1$ include 4-[2-(dimethylamino)ethyl]piperazin-1-yl, 4-pyrrolidin-1-ylpiperidin-1-yl, 4-[(dimethylamino)methyl]piperidin-1-yl, 4-azetidin-1-ylpiperidin-1-yl, 4-[3-(dimethylamino)azetidin-1-yl]piperidin-1-yl, 4-(4-methylpiperazin-1-yl)piperidin-1-yl, 4-(1-methylpiperidin-4-yl)piperazin-1-yl, 4-(1-methylazetidin-3-yl)piperazin-1-yl, 4-(dimethylamino)piperidin-1-yl, 4-(azetidin-1-ylmethyl)piperidin-1-yl, 4-(pyrrolidin-1-ylmethyl)piperidin-1-yl, (3S)-3-(dimethylamino)pyrrolidin-1-yl, (3R)-3-(dimethylamino)pyrrolidin-1-yl, azetidin-1-yl, pyrrolidin-1-yl, morpholin-4-yl, 4-methylpiperazin-1-yl, 3-hydroxyazetidin-1-yl, 1,3'-biazetidin-1'-yl, 3-(hydroxymethyl)azetidin 1-yl, 3-(dimethylamino)azetidin-1-yl, 3-[(dimethylamino)methyl]azetidin-1-yl, 4-hydroxypiperidin-1-yl, 4-(hydroxymethyl)piperidin-1-yl, (3R)-3-hydroxypyrrolidin-1-yl, (3S)-3-hydroxypyrrolidin-1-yl, 3-(azetidin-1-ylmethyl)azetidin-1-yl, 3-(2-dimethylaminoacetoxy)azetidin-1-yl, methyl(1-methylpiperidin-4-yl)amino, (1-ethylpiperidin-4-yl)(methyl)amino, [3-(dimethylamino)propyl](methyl)amino, [3-(diethylamino)propyl](methyl)amino or the like.

More preferable examples of $R^1$ include 4-(4-methylpiperazin-1-yl)piperidin-1-yl, 3-hydroxyazetidin-1-yl, (3R)-3-hydroxypyrrolidin-1-yl, (3S)-3-hydroxypyrrolidin-1-yl, methyl(1-methylpiperidin-4-yl)amino or the like.

[The Definition of Substituent Group A]

Substituent Group A represents a group consists of hydroxyl, dimethylaminoacetoxy, methyl, ethyl, dimethylamino, azetidinyl, pyrrolidinyl, piperidinyl and piperazinyl.

Each group included in Substituent Group A other than hydroxyl and dimethylaminoacetoxy may be substituted with hydroxyl, methyl, dimethylamino, azetidinyl, pyrrolidinyl or piperidinyl.

[The Definition of Substituent Group B]

Substituent Group B consists of methyl, ethyl, n-propyl, acetyl, dimethylamino, diethylamino, azetidinyl, pyrrolidinyl and piperazinyl.

Each group included in Substituent Group B may be substituted with methyl or dimethylamino.

[The Definition of $R^2$, $R^3$, $R^4$ and $R^5$]

$R^2$, $R^3$, $R^4$ and $R^5$ may be the same or different and each represents hydrogen or fluorine.

$R^2$, $R^3$, $R^4$ and $R^5$ may be (1) the case where all represent hydrogen, (2) the case where all represent fluorine, or (3) the case where some represent hydrogen and other represent fluorine, and preferably two or three of $R^2$, $R^3$, $R^4$ and $R^5$ are hydrogen.

Preferable examples of the group represented by the formula:

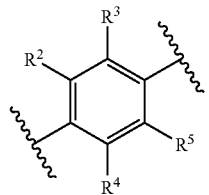

include a group represented by the formula:

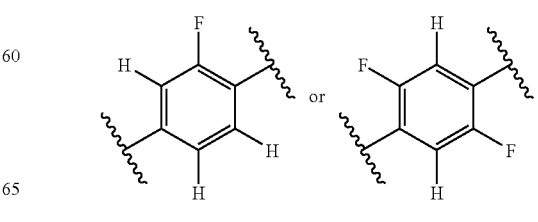

[The Definition of $R^6$]

$R^6$ represents hydrogen or fluorine.

Preferable examples of $R^6$ include fluorine.

[The Definition of $R^7$]

$R^7$ represents $C_{1-6}$ alkyl or benzyl optionally substituted with one or two substituents selected from (1) halogen, (2) hydroxyl, (3) nitro, (4) cyano, (5) trifluoromethyl, (6) $C_{1-6}$ alkyl, (7) $C_{1-6}$ alkoxy, (8) amino, (9) mono-$C_{1-6}$ alkylamino and (10) di-$C_{1-6}$ alkylamino on the benzene ring.

Preferable examples of $R^7$ include benzyl.

[The Definition of $R^{71}$]

$R^{71}$ represents hydrogen, $C_{1-6}$ alkyl or benzyl optionally substituted with one or two substituents selected from (1) halogen, (2) hydroxyl, (3) nitro, (4) cyano, (5) trifluoromethyl, (6) $C_{1-6}$ alkyl, (7) $C_{1-6}$ alkoxy, (8) amino, (9) mono-$C_{1-6}$ alkylamino and (10) di-$C_{1-6}$ alkylamino on the benzene ring.

Preferable examples of $R^{71}$ include hydrogen or benzyl.

[The Definition of Ar]

Ar represents phenyl optionally substituted with one or two substituents selected from halogen, methyl, methoxy, nitro, cyano and trifluoromethyl.

Preferable examples of Ar include phenyl.

The preparing process according to the invention will be describe below in detail.

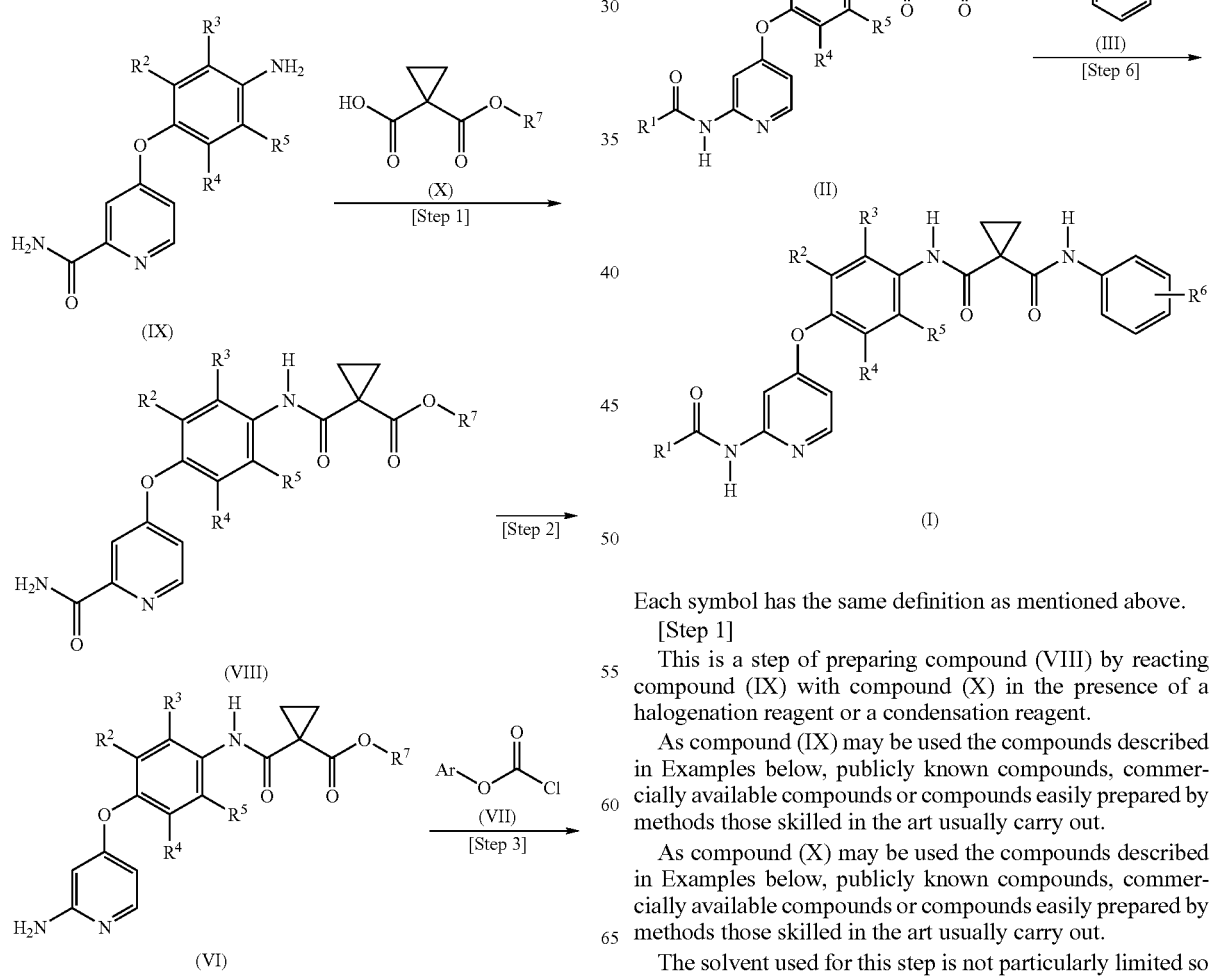

Each symbol has the same definition as mentioned above.

[Step 1]

This is a step of preparing compound (VIII) by reacting compound (IX) with compound (X) in the presence of a halogenation reagent or a condensation reagent.

As compound (IX) may be used the compounds described in Examples below, publicly known compounds, commercially available compounds or compounds easily prepared by methods those skilled in the art usually carry out.

As compound (X) may be used the compounds described in Examples below, publicly known compounds, commercially available compounds or compounds easily prepared by methods those skilled in the art usually carry out.

The solvent used for this step is not particularly limited so long as it dissolves starting materials to some extent and does not inhibit the reaction, and includes, for example, ether solvents such as tetrahydrofuran, 1,2-dimethoxyethane, tert-butyl methyl ether, cyclopentyl methyl ether, diethyl ether, diisopropyl ether, dibutyl ether and dicyclopentyl ether; aromatic hydrocarbon solvents such as benzene and toluene; aliphatic hydrocarbon solvents such as heptane and hexane; N,N-dimethylformamide; N-methyl-2-pyrrolidone; or a mixed solvent thereof, or the like and tetrahydrofuran is preferable.

The halogenation reagent represents thionyl chloride, oxalyl chloride, phosphorus trichloride, phosphorus oxychloride, phosphorus pentachloride or the like, and thionyl chloride is preferable.

The condensation reagent represents 4-(4,6-dimethoxy[1.3.5]triazin-2-yl)-4-methylmorpholinium chloride hydrate, 2-chloro-4,6-dimethoxy-1,3,5-triazine, 2,4,6-trichloro-1,3,5-triazine, dicyclohexyl carbodiimide (DCC), 1-ethyl-3,(3'-dimethylaminopropyl)carbodiimide HCl salt (EDC or WSC HCl), O-(1H-benzothiazol-1-yl)-N,N,N',N'-tetramethyluronium hexafluorophosphate (HBTU), O-(1H-benzothiazol-1-yl)-N,N,N',N'-tetramethyluronium tetrafluoroborate (TBTU) or the like, and 4-(4,6-dimethoxy[1.3.5]triazin-2-yl)-4-methylmorpholinium chloride hydrate or 2,4,6-trichloro-1,3,5-triazine is preferable.

The reaction temperature will generally differ depending on the starting materials, the solvent and the other reagents used in the reaction, and it is preferably 0° C. to 5° C. (internal temperature of the reaction vessel) and more preferably 0° C. to 30° C. (internal temperature of the reaction vessel).

The reaction time will generally differ depending on the starting materials, the solvent, the other reagents used in the reaction and the reaction temperature, and stirring at the above reaction temperature for 1 to 48 hours after the addition of the reagents is preferable and stirring for 4 to 24 hours is more preferable.

Compound (X) can be used in an amount of 1.0- to 3.0-fold molar amount with respect to compound (IX), and preferably it is used in an amount of 1.0- to 1.3-fold molar.

The halogenation reagent can be used in an amount of 1.0- to 2.0-fold molar amount with respect to compound (IX), and preferably it is used in an amount of 1.1-fold molar.

The condensation reagent can be used in an amount of 1.0- to 3.0-fold molar amount with respect to compound (IX), and preferably it is used in an amount of 1.1- to 1.3-fold molar.

[Step 2]

This is a step of preparing compound (VI) by reacting compound (VIII) with a Hofmann rearrangement reagent.

The solvent used for this step is not particularly limited so long as it dissolves starting materials to some extent and does not inhibit the reaction, and include, for example, N,N-dimethylformamide, N,N-dimethylacetamide, dimethyl sulfoxide, N-methyl-2-pyrrolidone or the like, and N,N-dimethylformamide or N-methyl-2-pyrrolidone is preferable.

The Hofmann rearrangement reagent represents iodobenzene diacetate, iodobenzene bis(trifluoroacetate), sodium hypochlorite, potassium hypobromite, bromine, iodine or the like, and iodobenzene diacetate or iodobenzene bis(trifluoroacetate) is preferable.

The reaction temperature will generally differ depending on the starting materials, the solvent and the other reagents used in the reaction, and it is preferably −10° C. to 50° C. (internal temperature of the reaction vessel) and more preferably 20° C. to 30° C. (internal temperature of the reaction vessel).

The reaction time will generally differ depending on the starting materials, the solvent, the other reagents used in the reaction and the reaction temperature, and stirring at the above reaction temperature for 1 to 24 hours after the addition of the reagents is preferable and stirring for 3 to 5 hours is more preferable.

The Hofmann rearrangement reagent can be used in an amount of 1.0- to 3.0-fold molar amount with respect to compound (VIII), and preferably it is used in an amount of 1.0- to 1.2-fold molar.

[Step 3]

This is a step of preparing compound (V) by reaction compound (VI) with compound (VII) in the presence of a base, As compound (VII) may be used publicly known compounds, commercially available compounds or compounds easily prepared by methods those skilled in the art usually carry out.

The solvent used for this step is not particularly limited so long as it dissolves starting materials to some extent and does not inhibit the reaction, and includes, for example, ether solvents such as tetrahydrofuran, 1,2-dimethoxyethane, tert-butyl methyl ether, cyclopentyl methyl ether, diethyl ether, diisopropyl ether, dibutyl ether and dicyclopentyl ether; aromatic hydrocarbon solvents such as benzene and toluene; aliphatic hydrocarbon solvents such as heptane and hexane; acetonitrile; or a mixed solvent thereof or the like, and a mixed solvent of tetrahydrofuran and acetonitrile is preferable.

The base represents pyridine, triethylamine, diisopropylethylamine, potassium carbonate, sodium carbonate or the like, and pyridine is preferable.

The reaction temperature will generally differ depending on the starting materials, the solvent and the other reagents used in the reaction, and it is preferably −10° C. to 50° C. (internal temperature of the reaction vessel) and more preferably 0° C. to 30° C. (internal temperature of the reaction vessel).

The reaction time will generally differ depending on the starting materials, the solvent, the other reagents used in the reaction and the reaction temperature, and stirring at the above reaction temperature for 1 to 24 hours after the addition of the reagents is preferable and stirring for 2 to 5 hours is more preferable.

Compound (VII) can be used in an amount of 1.0- to 3.0-fold molar amount with respect to compound (VI), and preferably it is used in an amount of 1.1- to 2.0-fold molar.

The base can be used in an amount of 1.0- to 3.0-fold molar amount with respect to compound (VI), and preferably it is used in an amount of 1.1- to 2.0-fold molar.

[Step 4]

This is a step of preparing compound (IV) or salt thereof by reacting compound (V) with an appropriate amine (or salt thereof) in the presence or absence of a base.

As amine may be used the compounds described in Examples below, publicly known compounds, commercially available compounds or compounds easily prepared by methods those skilled in the art usually carry out.

The solvent used for this step is not particularly limited so long as it dissolves starting materials to some extent and does not inhibit the reaction, and includes, for example, N,N-dimethylformamide, N-methyl-2-pyrrolidone, N,N-dimethylacetamide, dimethyl sulfoxide or the like, and N-methyl-2-pyrrolidone is preferable.

The base represents potassium carbonate, sodium carbonate, pyridine, triethylamine, diisopropylethylamine or the like, and potassium carbonate is preferable.

The reaction temperature will generally differ depending on the starting materials, the solvent and the other reagents used in the reaction, and it is preferably 10° C. to 100° C.

(internal temperature of the reaction vessel) and more preferably 20° C. to 50° C. (internal temperature of the reaction vessel).

The reaction time will generally differ depending on the starting materials, the solvent, the other reagents used in the reaction and the reaction temperature, and stirring at the above reaction temperature for 1 to 24 hours after the addition of the reagents is preferable and stirring for 1 to 4 hours is more preferable.

The amine (or salt thereof) can be used in an amount of 1.0- to 3.0-fold molar amount with respect to compound (V), and preferably it is used in an amount of 1.1- to 1.3-fold molar.

The base can be used in an amount of 1.0- to 3.0-fold molar amount with respect to compound (V), and preferably it is used in an amount of 1.1- to 1.3-fold molar.

After the above step, the reaction generally used such as oxidation, reduction, esterification, amidation, introduction of protecting groups, deprotection, hydrolysis or the like can be carried out if necessary in order to convert the substituents on $R^1$.

[Step 5]

This is a step of preparing compound (II) or salt thereof by hydrolysis or catalytic hydrogenation of compound (IV) or salt thereof.

(1) In the Case of Hydrolysis

Compound (II) or salt thereof can be prepared by hydrolysis of compound (IV) or salt thereof in the presence of an acid or a base.

The solvent used for this step is not particularly limited so long as it dissolves starting materials to some extent and does not inhibit the reaction, and includes for example, alcohol solvents such as methanol, ethanol, propanol and butanol; ether solvents such as tetrahydrofuran, 1,2-dimethoxyethane, tert-butyl methyl ether, cyclopentyl methyl ether, diethyl ether, diisopropyl ether, dibutyl ether and dicyclopentyl ether; water; or a mixed solvent thereof or the like, and a mixed solvent of water and methanol, ethanol or tetrahydrofuran is preferable.

The acid represents hydrochloric acid or the like.

The base represents sodium hydroxide, potassium hydroxide, potassium carbonate, sodium carbonate or the like.

The reaction temperature will generally differ depending on the starting materials, the solvent and the other reagents used in the reaction, and it is preferably 0° C. to 80° C. (internal temperature of the reaction vessel) and more preferably 30° C. to 50° C. (internal temperature of the reaction vessel).

The reaction time will generally differ depending on the starting materials, the solvent, the other reagents used in the reaction and the reaction temperature, and stirring at the above reaction temperature for 1 to 24 hours after the addition of the reagents is preferable and stirring for 2 to 5 hours is more preferable.

The acid can be used in an amount of 1.0- to 5.0-fold molar amount with respect to compound (IV), and preferably it is used in an amount of 1.0- to 2.0-fold molar. The base can be used in an amount of 1.0- to 5.0-fold molar amount with respect to compound (IV), and preferably it is used in an amount of 1.0- to 2.0-fold molar.

(2) In the Case of Catalytic Hydrogenation

This is a step of preparing compound (II) or salt thereof by catalytic hydrogenation of compound (IV) or salt thereof in the presence of a reduction catalyst under a hydrogen atmosphere.

The solvent used for this step is not particularly limited so long as it dissolves starting materials to some extent and does not inhibit the reaction, and includes, for example, alcohol solvents such as methanol, ethanol, propanol and butanol; ether solvents such as tetrahydrofuran, 1,2-dimethoxyethane, tert-butyl methyl ether, cyclopentyl methyl ether, diethyl ether, diisopropyl ether, dibutyl ether and dicyclopentyl ether; N,N-dimethylformamide; N-methyl-2-pyrrolidone; formic acid; water; or a mixed solvent thereof, and a mixed solvent of water, methanol and tetrahydrofuran, a mixed solvent of water, ethanol and tetrahydrofuran, or a mixed solvent of water and ethanol is preferable.

The reduction catalyst represents palladium on carbon, palladium hydroxide, platinum oxide, Raney nickel or the like, and palladium on carbon is preferable.

This step can be carried out under a hydrogen atmosphere at 0.1 MPa (ordinary pressure) to 1.0 MPa, and more preferably under a hydrogen atmosphere at 0.1 MPa to 0.3 MPa.

When formic acid or a mixed solvent containing formic acid is used as a solvent for this step, this step can be carried out without using hydrogen gas.

The reaction temperature will generally differ depending on the starting materials, the solvent and the other reagents used in the reaction, and it is preferably 0° C. to 50° C. (internal temperature of the reaction vessel) and more preferably 20° C. to 30° C. (internal temperature of the reaction vessel).

The reaction time will generally differ depending on the starting materials, the solvent, the other reagents used in the reaction and the reaction temperature, and stirring at the above reaction temperature for 1 to 48 hours after the addition of the reagents is preferable and stirring for 3 to 18 hours is more preferable.

The reduction catalyst can be used in an amount of 0.1- to 5.0-fold molar amount with respect to compound (IV), and preferably it is used in an amount of 0.5- to 1.5-fold molar.

[Step 6]

This is a step of preparing compound (I) by reacting compound (II) or salt thereof with compound (III) in the presence of a condensation reagent and in the presence or absence of a base.

As compound (III) may be used publicly known compounds, commercially available compounds or compounds easily prepared by methods those skilled in the art usually carry out.

The solvent used for this step is not particularly limited so long as it dissolves starting materials to some extent and does not inhibit the reaction, and includes, for example, ether solvents such as tetrahydrofuran, 1,2-dimethoxyethane, tert-butyl methyl ether, cyclopentyl methyl ether, diethyl ether, diisopropyl ether, dibutyl ether and dicyclopentyl ether; alcohol solvents such as ethanol, 1-propanol, 2-propanol; N,N-dimethylformamide; N-methyl-2-pyrrolidone; N,N-dimethylformamide; or a mixed solvent thereof, and a mixed solvent of tetrahydrofuran and N,N-dimethylformamide or a mixed solvent of tetrahydrofuran and 2-propanol is preferable.

The condensation reagent represents 4-(4,6-dimethoxy[1.3.5]triazin-2-yl)-4-methylmorpholinium chloride hydrate, 2-chloro-4,6-dimethoxy-1,3,5-triazine, 2,4,6-trichloro-1,3,5-triazine, dicyclohexyl carbodiimide (DCC), 1-ethyl-3,(3'-dimethylaminopropyl)carbodiimide HCl salt (EDC or WSC HCl), O-(1H-benzothiazol-1-yl)-N,N,N',N'-tetramethyluronium hexafluorophosphate (HBTU), O-(1H-benzothiazol-1-yl)-N,N,N',N'-tetramethyluronium tetrafluoroborate (TBTU) or the like, and 4-(4,6-dimethoxy[1.3.5]triazin-2-yl)-4-methylmorpholinium chloride hydrate or 2,4,6-trichloro-1,3,5-triazine is preferable.

The base represents N-methylmorpholine, pyridine, triethylamine, diisopropylethylamine, 1-methylimidazole, potassium carbonate, sodium carbonate or the like, and N-methylmorpholine is preferable.

The reaction temperature will generally differ depending on the starting materials, the solvent and the other reagents used in the reaction, and it is preferably −10° C. to 50° C. (internal temperature of the reaction vessel) and more preferably 20° C. to 30° C. (internal temperature of the reaction vessel).

The reaction time will generally differ depending on the starting materials, the solvent, the other reagents used in the reaction and the reaction temperature, and stirring at the above reaction temperature for 1 to 48 hours after the addition of the reagents is preferable and stirring for 3 to 18 hours is more preferable.

Compound (III) can be used in an amount of 1.0- to 3.0-fold molar amount with respect to compound (II), and preferably it is used in an amount of 1.0- to 2.0-fold molar.

The condensation reagent can be used in an amount of 1.0- to 3.0-fold molar amount with respect to compound (II), and preferably it is used in an amount of 1.0- to 2.0-fold molar.

The base can be used in an amount of 1.0- to 10-fold molar amount with respect to compound (II), and preferably it is used in an amount of 2.0- to 4.0-fold molar.

EXAMPLE

Examples are illustrated below for the purpose of the easy understanding of the present invention, but the present invention is not limited to these Examples.

Production Example 1 tert-Butyl [1-(2-dimethylaminoacetyl)piperidin-4-yl]carbamate

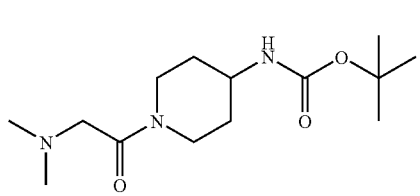

N,N-Dimethylglycine (2.97 g), 1-hydroxybenzotriazole (3.89 g) and 1-ethyl-3-(3-dimethylaminopropyl)carbodiimide hydrochloride (5.27 g) were added to a solution of 4-(tert-butoxycarbonylamino)piperidine (5.0 g) in N,N-dimethylformamide (70 ml), followed by stirring at room temperature under a nitrogen atmosphere for 46 hours. Ethyl acetate (400 ml), brine (200 ml) and a 1N aqueous solution of sodium hydroxide (50 ml) were added to the reaction mixture, followed by stirring at room temperature for 30 minutes, and the mixture was partitioned. The aqueous layer was extracted with ethyl acetate. The organic layer was collected, washed with a 1N aqueous solution of sodium hydroxide and brine in this order, and dried over anhydrous sodium sulfate. The dried organic layer was concentrated under reduced pressure to give the title compound (8.03 g, quant.) as white crystals.

ESI-MS (m/z): 286[M+H]$^+$.

Production Example 2

N-[1-(2-Dimethylaminoethyl)piperidin-4-yl]-N-methylamine

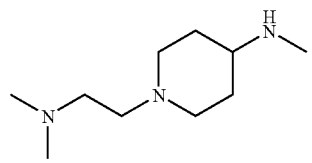

A solution of tert-butyl [1-(2-dimethylaminoacetyl)piperidin-4-yl]carbamate (7.07 g) in tetrahydrofuran (100 ml) was stirred with cooling on ice under a nitrogen atmosphere. Lithium aluminium hydride (280 mg) was added thereto, followed by stirring on an ice bath for 15 minutes, then at room temperature for 15 minutes. The reaction mixture was heated and refluxed under a nitrogen atmosphere at 100° C. for 11 hours. The reaction mixture was cooled on ice. Water (2.8 ml), a 5N aqueous solution of sodium hydroxide (2.8 ml) and water (14.0 ml) was added thereto in this order, followed by stirring for 2 hours. Insoluble matter was removed by filtration. The filtrate was concentrated to give the title compound (4.65 g, quant.) as a yellow oil.

$^1$H-NMR Spectrum (CDCl$_3$) δ (ppm): 1.34-1.43 (2H, m), 1.87-1.90 (2H, m), 2.02-2.08 (2H, m), 2.25 (6H, s), 2.31-2.50 (7H, m), 2.90 (2H, m), 3.14-3.27 (1H, m).

ESI-MS (m/z): 186[M+H]$^+$.

Production Example 3

(4-Benzoylpiperazin-1-yl)acetic acid ethyl ester

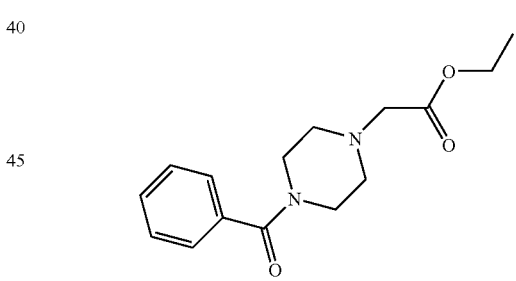

1-(Ethoxycarbonylmethyl)piperazine (5.1 g) was dissolved in tetrahydrofuran (300 ml) under a nitrogen atmosphere, and triethylamine (8.25 ml) and benzoyl chloride (3.44 ml) was added thereto with cooling in an ice water bath. The reaction mixture was brought to room temperature, followed by stirring for 4 hours. The reaction mixture was partitioned between ethyl acetate (200 ml) and a saturated aqueous solution of sodium hydrogencarbonate (100 ml). The separated organic layer was washed with a saturated aqueous solution of sodium hydrogencarbonate (100 ml), water (100 ml) and brine (100 ml), and dried over sodium sulfate. The solvent was distilled off under reduced pressure to give the title compound (8.19 g, quant.) as a colorless oil.

$^1$H-NMR Spectrum (CDCl$_3$) δ (ppm): 1.28 (3H, t, J=7.2 Hz), 2.20-2.85 (4H, m), 3.26 (2H, m), 3.48 (2H, m), 3.85 (2H, m), 4.19 (2H, m), 7.41 (5H, m).

Production Example 4

1-(Azetidin-1-yl)-2-(4-benzoylpiperazin-1-yl)ethanone

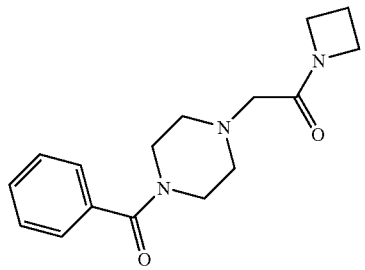

Methanol (300 ml) and water (50 ml) were added to (4-benzoylpiperazin-1-yl)acetic acid ethyl ester (8.19 g), and lithium hydroxide (1.34 g) was added thereto with cooling in an ice water bath, followed by stirring for 10 minutes. The reaction mixture was brought to room temperature, followed by stirring for 24 hours. After adding 1N hydrochloric acid (55.9 ml), the reaction mixture was concentrated under reduced pressure, and ethanol (200 ml) was added to the resultant residue. The precipitated insoluble matter was removed by filtration through celite. The filtrate was concentrated under reduced pressure to give a crude product of (4-benzoylpiperazin-1-yl)acetic acid (8.6 g) as a white solid. N,N-Dimethylformamide (80 ml) was added to (4-benzoylpiperazin-1-yl)acetic acid (2 g) at room temperature under a nitrogen atmosphere, and azetidine hydrochloride (1.51 g), triethylamine (4.49 ml), 1-ethyl-3-(3-dimethylaminopropyl)carbodiimide hydrochloride (3.09 g) and 1-hydroxybenzotriazole (2.18 g) were added in this order, followed by stirring at room temperature for 66 hours. Ethyl acetate (100 ml) and a saturated aqueous solution of sodium hydrogencarbonate (50 ml) were added to the reaction mixture, which was partitioned. The organic layer was washed with a saturated aqueous solution of sodium hydrogencarbonate (50 ml), water (50 ml) and brine (50 ml) in this order, and dried over anhydrous sodium sulfate. The residue obtained by distilling off the solvent under reduced pressure was purified by silica gel column chromatography (Fuji Silysia NH, eluent; ethyl acetate). The residue obtained by concentrating the fractions containing the target compound under reduced pressure was suspended by the addition of diethyl ether (10 ml). The solid was collected by filtration, and dried under aeration to give the title compound (731.5 mg) as white powder.

$^1$H-NMR Spectrum (CDCl$_3$) δ (ppm): 2.40-2.80 (6H, m), 3.03 (2H, s), 3.47 (2H, m), 3.83 (2H, m), 4.06 (2H, m), 4.22 (2H, m), 7.30-7.50 (5H, m).

Production Example 5

1-[2-(Azetidin-1-yl)ethyl]-4-benzylpiperazine

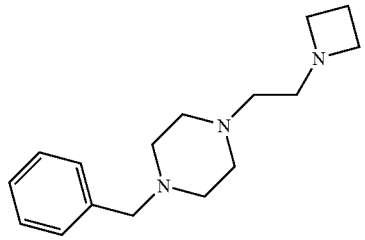

Lithium aluminium hydride (405 mg) was suspended in tetrahydrofuran (10 ml) under a nitrogen atmosphere with stirring in an ice water bath, 1-(azetidin-1-yl)-2-(4-benzoylpiperazin-1-yl)ethanone (730 mg) and tetrahydrofuran (5 ml×3) was added thereto. The reaction mixture was stirred at 60° C. for 3 hours. The reaction mixture was allowed to cool down to room temperature, and water (0.4 ml), a 5N aqueous solution of sodium hydroxide (0.4 ml) and water (1.2 ml) were added thereto, followed by stirring for 13 hours. The insoluble matter in the reaction mixture was removed by filtration through celite, and washed with ethyl acetate (100 ml). The solvent was distilled off under reduced pressure to give a crude product of the title compound (687 mg) as a pale yellow oil.

ESI-MS (m/z): 260[M+H]$^+$.

Production Example 6

1-[2-(Azetidin-1-yl)ethyl]piperazine trihydrochloride

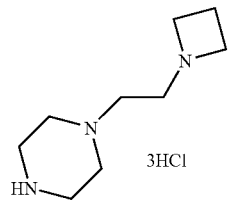

1-[2-(Azetidin-1-yl)ethyl]-4-benzylpiperazine (687 mg) was dissolved in methanol (30 ml), and 20% palladium hydroxide on carbon (372 mg) was added thereto, followed by stirring under a pressurized hydrogen atmosphere (0.4 MPa) for 10 hours. The catalyst was removed by filtration and washed with methanol. 4N hydrochloric acid in ethyl acetate (1.33 ml) was added to the filtrate, followed by stirring. Excess hydrochloric acid was removed by pressure reduction in the system with stirring. The solvent was distilled off to give the title compound (736 mg, quant.) as a pale brown oil.

ESI-MS (m/z): 170[M+H]$^+$.

Production Example 7

1-Benzhydrylazetidin-3-one

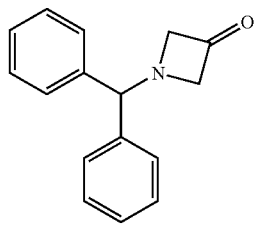

A solution of pyridine sulfur trioxide complex (19.7 g) in dimethyl sulfoxide (80 ml) was added dropwise to a mixture of 1-benzhydrylazetidin-3-ol hydrochloride (5.52 g) and triethylamine (27.9 ml) at room temperature. The reaction mixture was stirred at 50° C. for 30 minutes. The reaction mixture was allowed to cool down to room temperature, and poured into ice water. This was extracted with ethyl acetate, and the organic layer was washed with brine. Activated carbon (5 g) was added to the organic layer, followed by stirring at room temperature for 3 days. The activated carbon was removed by filtration, and the filtrate was concentrated. The residue was dissolved in methanol (200 ml), and activated carbon (10 g) was added thereto, followed by stirring at room temperature for 3 days. The activated carbon was removed by filtration, and the filtrate was concentrated. The residue was purified by silica gel column chromatography (eluent; heptane:ethyl acetate=4:1, then 2:1). The fractions containing the target compound were concentrated to give the target compound (3.21 g) as a pale yellow oil. Hexane was added thereto to precipitate crystals, and the crystals were collected by filtration. Drying under aeration gave the title compound (1.11 g, 23.4%) as white crystals. Hexane was added to the residue obtained by concentration of the filtrate, which was allowed to stand at room temperature. After crystals precipitated, the supernatant was removed using a pipette. These were dried under reduced pressure to give the title compound (940 mg, 19.8%) as pale yellow crystals.

$^1$H-NMR Spectrum (CDCl$_3$) δ (ppm): 4.01 (4H, s), 4.60 (1H, s), 7.22 (2H, m), 7.30 (4H, m), 7.48 (4H, m).

Production Example 8

3-(Azetidin-1-yl)-1-benzhydrylazetidine

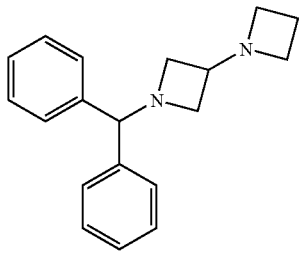

Azetidine hydrochloride (326 mg) was added to a solution of 1-benzhydrylazetidin-3-one (750 mg) in dichloromethane (12 ml), followed by stirring at room temperature. Sodium triacetoxyborohydride (1.01 g) was added thereto, followed by stirring at room temperature for 25 hours. Sodium carbonate (until bubbling stopped), water (50 ml) and ethyl acetate (100 ml) was added to the reaction mixture. The organic layer was separated, washed with brine and dried over anhydrous sodium sulfate. The dried organic layer was concentrated under reduced pressure. The residue was purified by silica gel column chromatography (Fuji Silysia NH, eluent; heptane:ethyl acetate=1:1, 1:2, then ethyl acetate) to give the title compound (643 mg, 73.1%) as a pale yellow solid.

$^1$H-NMR Spectrum (CDCl$_3$) δ (ppm): 2.06 (2H, m), 2.91 (2H, m), 3.16-3.24 (7H, m), 4.35 (1H, s), 7.15 (2H, m), 7.25 (4H, m), 7.40 (4H, d, J=7.6 Hz).

ESI-MS (m/z): 279[M+H]$^+$.

Production Example 9

3-(Azetidin-1-yl)azetidine dihydrochloride

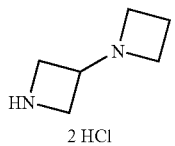

2 HCl 4N hydrochloric acid in ethyl acetate (1.16 ml) was added to a solution of 3-(azetidin-1-yl)-1-benzhydrylazetidine (643 mg) in ethyl acetate, and the mixture was concentrated. The resultant residue was dissolved in methanol (65 ml), and 20% palladium hydroxide (811 mg) was added thereto. This mixture was stirred under a pressurized hydrogen atmosphere (0.3 to 0.4 MPa) at room temperature for 4 hours. The catalyst was removed by filtration, and the filtrate was concentrated. The solid was suspended by the addition of heptane to the residue. The supernatant was removed using a pipette and the residue was concentrated under reduced pressure to give a crude product of the title compound (471.2 mg) as a pale yellow oil.

ESI-MS (m/z): 113[M+H]$^+$.

Production Example 10

1-Benzhydryl-3-(methanesulfonyloxy)azetidine

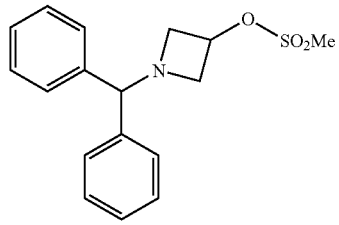

A suspension of 1-benzhydrylazetidin-3-ol (15.0 g) in pyridine (100 ml) was cooled down to −20° C. under a nitrogen atmosphere, and methanesulfonyl chloride (6.33 ml) was added dropwise. The reaction mixture was stirred under a nitrogen atmosphere at −20° C. for 1 hour, then in a water bath for 2.5 days. The reaction mixture was partitioned after addition of water and ethyl acetate. The organic layer was washed with a saturated aqueous solution of sodium hydrogencarbonate, water and brine, and dried over anhydrous sodium sulfate. The solvent was concentrated under reduced pressure. Ethanol (10 ml) and hexane (50 ml) was added to the residue, and the precipitated crystals were suspended. The crystals were collected by filtration and washed with hexane. This was dried under aeration at room temperature to give the title compound (5.943 g, 44.8%) as pale yellow crystals. The filtrate was concentrated, and the residue was purified by silica gel column chromatography (eluent; heptane:ethyl acetate=2:1, 1:1, heptane:ethyl acetate:methanol=50:50:1. 40:60:1, then ethyl acetate:methanol=100:1). The fractions containing the target compound were concentrated to give the title compound (1.58 g, 11.9%) as pale yellow crystals.

$^1$H-NMR Spectrum (CDCl$_3$) δ (ppm): 2.99 (3H, s), 3.18-3.21 (2H, m), 3.62-3.66 (2H, m), 4.40 (1H, s), 5.11 (1H, m), 7.18-7.22 (2H, m), 7.26-7.31 (4H, m), 7.39 (4H, d, J=7.2 Hz).

Production Example 11

1-Benzhydryl-3-cyanoazetidine

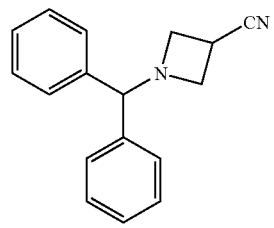

Water (7.2 ml) and sodium cyanate (3.48 g) were added to a solution of 1-benzhydryl-3-(methanesulfonyloxy)azetidine (7.52 g) in N,N-dimethylformamide (60 ml), followed by stirring at 65° C. for 9 hours. Water, sodium carbonate and ethyl acetate were added to the reaction mixture, which was partitioned. The aqueous layer was extracted with ethyl acetate. The organic layer was collected, washed with brine, and dried over anhydrous sodium sulfate. This was concentrated under reduced pressure, and the resultant crystals were suspended by addition of diethyl ether (10 ml). The crystals were collected by filtration, and washed with diethyl ether. This was dried under aeration to give the title compound (5.43 g, 92.3%) as pale yellow crystals.

$^1$H-NMR Spectrum (CDCl$_3$) δ (ppm): 3.20-3.31 (3H, m), 3.47 (2H, m), 4.36 (1H, s), 7.19-7.23 (2H, m), 7.26-7.30 (4H, m), 7.39 (4H, m).

Production Example 12

1-Benzhydrylazetidine-3-carboxylic acid

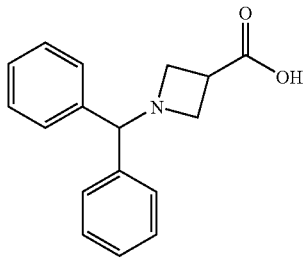

Potassium hydroxide (6.48 g) and water (3.25 ml) were added to a solution of 1-benzhydryl-3-cyanoazetidine (5.43 g) in methoxyethanol (54 ml), followed by stirring at 100° C. for 4 hours. The reaction mixture was allowed to cool down to room temperature, and poured into ice. After pH of the mixture was adjusted to 5 with 1N hydrochloric acid, sodium chloride was added thereto. This was extracted with a mixed solvent of ethyl acetate and tetrahydrofuran. The organic layer was washed with brine, and dried over anhydrous sodium sulfate. The dried organic layer was concentrated under reduced pressure to give a crude product of the title compound as pale yellow crystals. The crystals were suspended by the addition of diethyl ether (15 ml). The crystals were collected by filtration and washed with diethyl ether. This was dried under aeration to give the title compound (4.20 g, 71.7%) as pale yellow crystals.

$^1$H-NMR Spectrum (CDCl$_3$) δ (ppm): 3.00-3.90 (5H, m), 4.95 (1H, s), 7.25-7.28 (2H, m), 7.33 (4H, m), 7.53 (4H, m).

Production Example 13

Methyl 1-benzhydrylazetidine-3-carboxylate

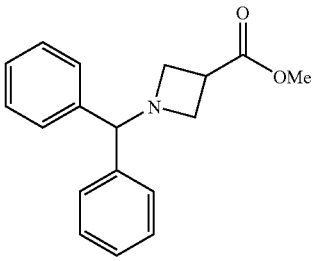

Potassium carbonate (6.53 g) and iodomethane (0.976 ml) were added to a solution of 1-benzhydrylazetidine-3-carboxylic acid (4.20 g) in N,N-dimethylformamide (45 ml), followed by stirring at room temperature for 20.5 hours. The reaction mixture was poured into ice water, and extracted with ethyl acetate. The organic layer was washed with brine, and dried over anhydrous sodium sulfate. The solvent was distilled off, and the residue was purified by silica gel column chromatography (eluent; heptane:ethyl acetate=5:1, then 3:1). The fractions containing the target compound were concentrated to give the title compound (3.57 g, 80.8%) as yellow crystals.

$^1$H-NMR Spectrum (CDCl$_3$) δ (ppm): 3.26 (2H, m), 3.31 (1H, m), 3.44 (2H, m), 3.69 (3H, s), 4.38 (1H, s), 7.16-7.20 (2H, m), 7.25-7.28 (4H, m), 7.39-7.41 (4H, m).

ESI-MS (m/z): 282[M+H]$^+$.

Production Example 14

Methyl azetidine-3-carboxylate hydrochloride

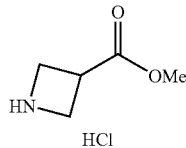

4N hydrochloric acid in ethyl acetate (12.7 ml) and 20% palladium hydroxide (3.57 g) were added to a solution of methyl 1-benzhydrylazetidine-3-carboxylate (3.57 g) in methanol (360 ml), followed by stirring under a pressurized hydrogen atmosphere (0.4 MPa) at room temperature for 11 hours. The catalyst was removed by filtration, and washed with methanol and water. The filtrate was concentrated to give a crude product of the target compound as a pale yellow oil, which was used in the next reaction supposing that the reaction proceeded quantitatively and 1.93 g of the product was obtained.

ESI-MS (m/z): 116[M+H]$^+$.

Production Example 15

Methyl 1-tert-butoxycarbonylazetidine-3-carboxylate

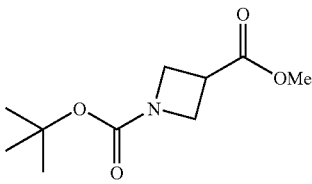

A crude product of methyl azetidine-3-carboxylate hydrochloride (calculated as 1.93 g of pure product) was dissolved in water (26 ml), sodium hydrogencarbonate (3.2 g), then a solution of di-t-butyl dicarbonate (2.91 g) in tetrahydrofuran (13 ml) were added with stirring and cooling in an ice bath, followed by stirring at the same temperature for 0.5 hours. The reaction mixture was stirred at room temperature for 19.5 hours. Tetrahydrofuran in the reaction mixture was distilled off, extraction was performed with ethyl acetate. The organic layer was washed with brine (70 ml) and dried over anhydrous sodium sulfate. The concentrated organic layer and the aqueous layer were combined, and tetrahydrofuran (50 ml) was added thereto. This was stirred with cooling in an ice bath, and sodium hydrogencarbonate (3.2 g), then di-t-butyl dicarbonate (2.91 g) were again added thereto. The reaction mixture was stirred at the same temperature for 0.5 hours, then at room temperature for 2.5 days. The reaction mixture was partitioned, and the aqueous layer was extracted with ethyl acetate. The organic layers were combined, and dried over anhydrous sodium sulfate. The solvent was distilled off, and the residue was purified by silica gel column chromatography (eluent; heptane:ethyl acetate=2:1, 1:1, ethyl acetate, then ethyl acetate:methanol=10:1). The fractions containing the target compound were concentrated to give the title compound (370 mg, 13.5%) as a colorless oil.

$^1$H-NMR Spectrum (CDCl$_3$) δ (ppm): 1.44 (9H, s), 3.35 (1H, m), 3.75 (3H, s), 4.10 (4H, d, J=7.6 Hz).

Production Example 16 tert-Butyl 3-(hydroxymethyl)azetidine-1-carboxylate

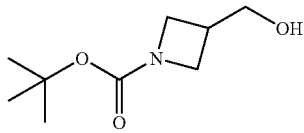

Lithium aluminium hydride (128 mg) was placed in a round bottomed flask, and suspended in tetrahydrofuran (30 ml). The suspension was cooled in an ice bath, and a solution of methyl 1-tert-butoxycarbonylazetidine-3-carboxylate (970 mg) in tetrahydrofuran (10 ml) was added gradually, followed by stirring at the same temperature under a nitrogen atmosphere for 1 hour. Water (0.13 ml), a 5N aqueous solution of sodium hydroxide (0.13 ml) and water (0.39 ml) was added to the reaction mixture with cooling in an ice bath, followed by stirring at the same temperature for 1 hour. Insoluble matter in the reaction mixture was removed by filtration. The filtrate was concentrated to give the title compound (805 mg, 95.3%) as a colorless oil.

$^1$H-NMR Spectrum (CDCl$_3$) δ (ppm): 1.44 (9H, s), 2.71 (1H, m), 3.69 (2H, dd, J=5.2, 8.4 Hz), 3.79 (2H, d, J=6.8 Hz), 4.00 (2H, m).

Production Example 17

3-(Hydroxymethyl)azetidine trifluoroacetate

Trifluoroacetic acid (0.413 ml) was added to tert-butyl 3-(hydroxymethyl)azetidine-1-carboxylate (125 mg) with cooling in an ice bath, followed by stirring at the same temperature for 30 minutes. Then the reaction mixture was stirred at room temperature for 1.5 hours. The reaction mixture was concentrated to give a crude product of the title compound (209.8 mg) as a yellow oil.

ESI-MS (m/z): 88[M+H]$^+$.

Production Example 18 tert-Butyl 3-[(methanesulfonyloxy)methyl]azetidine-1-carboxylate

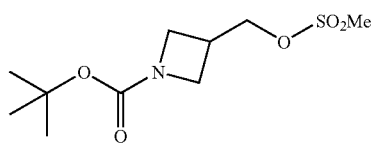

Triethylamine (1.80 ml) was added to a solution of tert-butyl 3-(hydroxymethyl)azetidine-1-carboxylate (806 mg) in tetrahydrofuran (25 ml). This was cooled on ice under a nitrogen atmosphere, and methanesulfonyl chloride (0.499 ml) was added dropwise, followed by stirring at the same temperature for 30 minutes. The reaction mixture was partitioned after the addition of ethyl acetate (100 ml) and water (70 ml). The aqueous layer was extracted with ethyl acetate. The combined organic layer was washed with brine, and dried over anhydrous sodium sulfate. The solvent was distilled off, and the residue was purified by silica gel column chromatography (eluent; ethyl acetate). The fractions containing the target compound were concentrated to give the title compound (1.05 g, 92.0%) as a colorless oil.

$^1$H-NMR Spectrum (CDCl$_3$) δ (ppm): 1.44 (9H, s), 2.93 (1H, m), 3.05 (3H, s), 3.72 (2H, dd, J=.5.0, 9.0 Hz), 4.06 (2H, m), 4.35 (2H, d, J=6.8 Hz).

ESI-MS (m/z): 288[M+Na]$^+$.

Production Example 19 tert-Butyl 3-(dimethylaminomethyl)azetidine-1-carboxylate

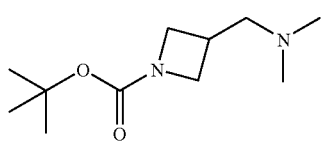

A 2M solution of dimethylamine in tetrahydrofuran (20 ml) was added to a solution of tert-butyl 3-[(methanesulfonyloxy)methyl]azetidine-1-carboxylate (1.05 g) in methanol (20 ml), and the reaction mixture was heated in a sealed tube at 70° C. for 40 hours. The reaction mixture was allowed to cool down to room temperature. The reaction mixture was concentrated, and partitioned between ethyl acetate and a saturated aqueous solution of sodium hydrogencarbonate. The organic layer was washed with brine, and dried over anhydrous sodium sulfate. The solvent was distilled off to give the title compound (678 mg, 79.9%) as a yellow oil.

$^1$H-NMR Spectrum (CDCl$_3$) δ (ppm): 1.43 (9H, s), 2.22 (6H, s), 2.50 (2H, d, J=7.6 Hz), 2.69 (1H, m), 3.59 (2H, dd, J=5.2, 8.4 Hz), 4.16 (2H, m).

ESI-MS (m/z): 215[M+H]$^+$, 269[M+Na+MeOH]$^+$.

Production Example 20

3-(Dimethylaminomethyl)azetidine bistrifluoroacetate

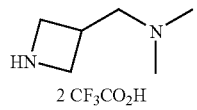

Trifluoroacetic acid (1.95 ml) was added to tert-butyl 3-(dimethylaminomethyl)azetidine-1-carboxylate (678 mg) with cooling on ice, followed by stirring at the same temperature for 30 minutes. Then, the reaction mixture was stirred at room temperature for 1.5 hours. The reaction mixture was concentrated and azeotropically distilled with toluene to give a crude product of the title compound (1.79 g) as a yellow oil.

ESI-MS (m/z): 115[M+Na]$^+$.

Production Example 21 tert-Butyl 3-methoxyazetidine-1-carboxylate

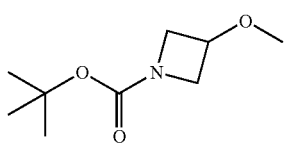

A suspension of sodium hydride (2.89 g) in tetrahydrofuran (50 ml) was stirred with cooling in an ice bath. A solution of tert-butyl 3-hydroxyazetidine-1-carboxylate (5.00 g) in tetrahydrofuran (50 ml) was gradually added, followed by stirring at the same temperature for 30 minutes. Then, the reaction mixture was stirred at room temperature for 30 minutes. The reaction mixture was stirred with cooling in an ice bath again for 15 minutes. Iodomethane (3.09 ml) was added dropwise to the reaction mixture, followed by stirring for 2 hours. Water was gradually added to the reaction mixture. When bubbling stopped, the organic layer was separated. The aqueous layer was extracted with ethyl acetate. The organic layers were combined, washed with brine, and dried over anhydrous sodium sulfate. The solvent was distilled off, and the residue was purified by silica gel column chromatography (eluent; heptane:ethyl acetate=3:1, 2:1, 1:1, then ethyl acetate). The fractions containing the target compound were concentrated to give the title compound (1.80 g, 33.3%) as a colorless oil. The fractions containing the starting material were concentrated and collected (2.10 g, 42.0%).

$^1$H-NMR Spectrum (CDCl$_3$) δ (ppm): 1.44 (9H, s), 3.28 (3H, s), 3.82 (2H, m), 4.06 (2H, m), 4.14 (1H, m).

Production Example 22

3-Methoxyazetidine trifluoroacetate

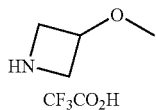

tert-Butyl 3-methoxyazetidine-1-carboxylate (125 mg) was dissolved in dichloromethane (0.618 ml), and trifluoroacetic acid (0.618 ml) was added thereto, followed by stirring at room temperature for 3.5 hours. The reaction mixture was concentrated to give a crude product of the target compound (232 mg) as a yellow oil.

ESI-MS (m/z): 88[M+H]$^+$.

Production Example 23

3-(Azetidin-1-ylcarbonyl)-1-benzhydrylazetidine

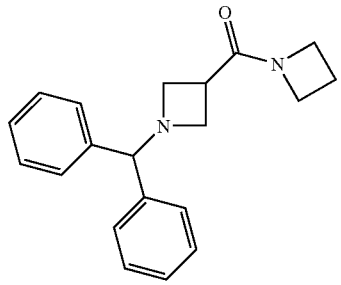

1-Benzhydrylazetidine-3-carboxylic acid (1.52 g) was dissolved in N,N-dimethylformamide (30 ml) at room temperature under a nitrogen atmosphere. Triethylamine (3.17 ml), BOP reagent (benzotriazole-1-yl-oxy-tris-(dimethylamino)-phosphonium hexafluorophosphate; 5.03 g) and azetidine hydrochloride (1.06 g) were added in this order, followed by stirring for 24 hours. A 1N aqueous solution of sodium hydroxide (50 ml) was added to the reaction mixture, followed by stirring. Then the reaction mixture was extracted after addition of ethyl acetate (100 ml). The separated organic layer was washed with a 1N aqueous solution of sodium hydroxide, water and brine, and dried over anhydrous sodium sulfate. To the residue (1.83 g) obtained by distilling off the solvent were added ethyl acetate (2 ml) and tert-butyl methyl ether (10 ml) to precipitate crystals. The crystals were collected by filtration, and dried under aeration to give the title compound (1.14 g, 65%) as pale yellow crystals.

$^1$H-NMR Spectrum (CDCl$_3$) δ (ppm): 2.15-2.30 (2H, m), 3.20-3.50 (5H, m), 3.90-4.10 (4H, m), 4.45 (1H, s), 7.15-7.45 (10H, m).

ESI-MS (m/z): 307[M+H]$^+$.

Production Example 24

3-(Azetidin-1-ylmethyl)-1-benzhydrylazetidine

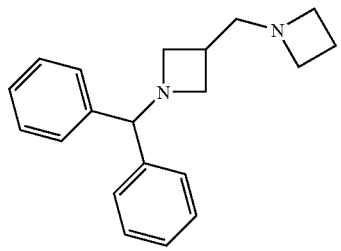

Lithium aluminium hydride (300 mg) was suspended in tetrahydrofuran (10 ml) at room temperature under a nitrogen atmosphere, and a solution of 3-(azetidin-1-ylcarbonyl)-1-benzhydrylazetidine (1.14 g) in tetrahydrofuran (30 ml) was added dropwise. After the addition, the reaction mixture was stirred at 60° C. for 2 hours. After the reaction mixture was cooled in an ice water bath, water (0.3 ml), a 5N aqueous solution of sodium hydroxide (0.3 ml) and water (0.9 ml) were added, followed by stirring overnight. Insoluble matter was removed by filtration, and washed with ethyl acetate (100 ml). The filtrate was concentrated under reduced pressure to give the title compound (1.115 g, quant.) as a pale brown oil.

¹H-NMR Spectrum (CDCl₃) δ (ppm): 2.07 (2H, m), 2.40-2.60 (3H, m), 2.74 (2H, m), 3.11-3.15 (4H, m), 3.32 (2H, m), 4.29 (1H, s), 7.14-7.40 (10H, m).
ESI-MS (m/z): 293[M+H]⁺.

Production Example 25

3-(Azetidin-1-ylmethyl)azetidine dihydrochloride

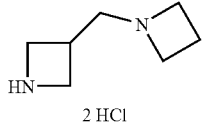

2 HCl 3-(Azetidin-1-ylmethyl)-1-benzhydrylazetidine (1.115 g) was dissolved in methanol (25 ml). 10% palladium on carbon (1.1 g) was added under a nitrogen atmosphere, followed by stirring under a pressurized hydrogen atmosphere (0.4 MPa) for 12 hours. After replacing the air of the vessel by nitrogen, the catalyst was removed by filtration, and washed with methanol. 4N hydrochloric acid in ethyl acetate (4 ml) was added to the reaction mixture, which was concentrated under reduced pressure. Heptane (25 ml) was added to the residue, and the supernatant was removed. This procedure was repeated once more. The resultant residue was dried under reduced pressure for 2 days to give the title compound (680 mg, 90%) as a pale brown oil.
ESI-MS (m/z): 127[M+H]⁺.

Production Example 26

1-Benzhydryl-3-(hydroxymethyl)azetidine

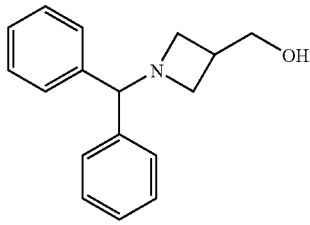

1-Benzhydryl-3-azetidinecarboxylic acid (3.12 g) was suspended in tetrahydrofuran (60 ml), and cooled in an ice-methanol bath under a nitrogen atmosphere. Triethylamine (1.96 ml) was added dropwise, and a solution of ethyl chlorocarbonate (1.34 ml) in tetrahydrofuran (5 ml) was added dropwise over 20 minutes. After the addition, the reaction mixture was stirred at the same temperature for 30 minutes. The reaction mixture was filtered, and the residue was washed with tetrahydrofuran (30 ml). The filtrate was added dropwise to a solution of an aqueous (15 ml) solution of sodium borohydride (1.33 g) cooled in an ice water bath over 15 minutes. After the addition, the reaction mixture was stirred at room temperature. 1N hydrochloric acid (35 ml) was gradually added to the reaction mixture to degrade excess sodium borohydride, and a 1N aqueous solution of sodium hydroxide (35 ml) was added. This was extracted with ethyl acetate (100 ml). The organic layer was washed with brine, and dried over anhydrous sodium sulfate. The solvent was concentrated, and the residue was dried under reduced pressure to give the title compound (1.59 g, 54%) as a pale brown solid.
¹H-NMR Spectrum (CDCl₃) δ (ppm): 2.57 (1H, m), 3.03 (2H, m), 3.24 (2H, m), 3.80 (2H, d, J=5.2 Hz), 4.33 (1H, s), 7.15-7.45 (10H, m).
ESI-MS (m/z): 254[M+H]⁺.

Production Example 27

3-(Hydroxymethyl)azetidine hydrochloride

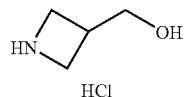

HCl

1-Benzhydryl-3-(hydroxymethyl)azetidine (1.59 g) was dissolved in methanol (30 ml) and palladium hydroxide on carbon (1.0 g) was added under a nitrogen atmosphere, followed by stirring under a pressurized hydrogen atmosphere (0.4 MPa). After replacing the air of the vessel by nitrogen, the catalyst was removed by filtration and washed with methanol. 4N hydrochloric acid in ethyl acetate (2 ml) was added to the reaction mixture, which was concentrated under reduced pressure. Heptane (15 ml) was added to the residue, and the supernatant was removed. This 1.0 procedure was repeated once more. The residue Was dried under reduced pressure overnight to give a crude product of the title compound (832 mg) as a pale yellow oil.
ESI-MS (m/z): 88[M+H]⁺.

Production Example 28

1-(Benzyloxy)-2,5-difluoro-4-nitrobenzene

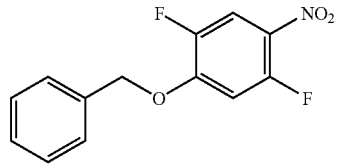

Potassium carbonate (11.1 g) was added to a solution of 2,4,5-trifluoronitrobenzene (9.48 g) and benzyl alcohol (5.54 ml) in N,N-dimethylformamide (40 ml), followed by stirring at room temperature for 60 hours. Water (120 ml) was added to the reaction mixture at 0° C., followed by stirring at 4° C. for 24 hours. The precipitated crystals were collected by filtration, and washed with water. The crystals were dried under reduced pressure to give the title compound (11.5 g, 81%) as pale yellow crystals.
¹H-NMR Spectrum (DMSO-d₆) δ (ppm): 5.35 (2H, s), 7.40-7.50 (5H, m), 7.64 (1H, dd, J=7.2, 13.2 Hz), 8.20 (1H, dd, J=7.2, 10.8 Hz).

Production Example 29

4-Amino-2,5-difluorophenol

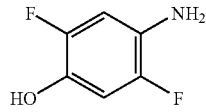

10% palladium on carbon (921 mg) was added to a solution of 1-(benzyloxy)-2,5-difluoro-4-nitrobenzen (9.21 g) in methanol (300 ml), followed by stirring at room temperature under hydrogen atmosphere for 24 hours and 20 minutes. The air of the flask was replaced with nitrogen to stop the reaction, and the catalyst was removed by filtration using celite. The filtrate was distilled off under reduced pressure to give the title compound (4.96 g, 99%) as a pale brown solid.
¹H-NMR Spectrum (DMSO-d₆) δ (ppm): 4.67 (1H, s), 6.53-6.64 (1H, m), 9.03 (1H, s).

Example 1

1-(Benzyloxycarbonyl)cyclopropanecarboxylic acid

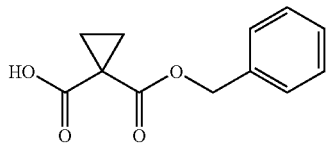

(Method 1)

1,1-Cyclopropanedicarboxylic acid (5.02 g) was dissolved in tetrahydrofuran (50 ml) under a nitrogen atmosphere, and triethylamine (5.38 ml) was added dropwise with stirring and cooling in an ice water bath. After stirring at the same temperature for 30 minutes, thionyl chloride (2.82 ml) was added dropwise with cooling in ice water bath. After stirring at the same temperature for 30 minutes, a solution of benzyl alcohol (4.39 ml) in tetrahydrofuran (25 ml) was added with cooling in an ice water bath, and the reaction mixture was gradually brought to room temperature and stirred overnight. A 2N aqueous solution of sodium hydroxide (100 ml) was added to the reaction mixture, and tetrahydrofuran was distilled off under reduced pressure. tert-Butyl methyl ether (25 ml) was added to the resultant aqueous solution, followed by stirring. The organic layer and the aqueous layer were separated. The aqueous layer was cooled in an ice water bath, and 2N hydrochloric acid (50 ml) was added to adjust pH 4. Ethyl acetate (150 ml) was added, and the reaction mixture was stirred for a while. The organic layer was separated, washed with brine, and dried over anhydrous sodium sulfate. The residue obtained by distilling off the solvent was dried under reduced pressure to give the title compound (6.29 g, 74%) as a pale yellow oil.

$^1$H-NMR Spectrum (DMSO-$d_6$) δ (ppm): 1.30-1.40 (4H, m), 5.15 (2H, s), 7.30-7.38 (5H, m).

ESI-MS (m/z): 243[M+Na]$^+$.

(Method 2)

1,1-Cyclopropanedicarboxylic acid (50 g) was dissolved in acetonitrile (500 ml) under a nitrogen atmosphere, and N-methylimidazole (31 ml) was added dropwise with stirring and cooling in an ice water bath. After stirring at the same temperature for 30 minutes, thionyl chloride (29 ml) was added dropwise. After stirring at the same temperature for 30 minutes, a mixed solution of benzyl alcohol (45.7 g) and N-methylimidazole (31 ml) was added with cooling in an ice water bath, and the reaction mixture was stirred at the same temperature for 6 hours. A 2N aqueous solution of sodium hydroxide (900 ml) was added to adjust pH 8. tert-Butyl methyl ether (500 ml) was added to the resultant solution, and the mixture was stirred. The organic layer and the aqueous layer were separated, and the organic layer was extracted with a 5% aqueous solution of sodium hydrogencarbonate (200 ml). The aqueous layers were combined, cooled in an ice water bath, and 5N hydrochloric acid (300 ml) was added to adjust pH 4. Ethyl acetate (1000 ml) was added, and the mixture was stirred for a while. The organic layer was separated, washed with brine, and dried over anhydrous sodium sulfate. The residue obtained by distilling off the solvent was dissolved in methanol (120 ml), and water (120 ml) was added dropwise with stirring at room temperature. After stirring at room temperature for 30 minutes, and with cooling in an ice water bath for 2 hours, the precipitated solid was suction filtered, and washed with water (60 ml, twice). The resultant solid was dried under reduced pressure at 40° C. to give the title compound (59 g, 69%).

Example 2

4-(4-Amino-3-fluorophenoxy)pyridine-2-carboxamide

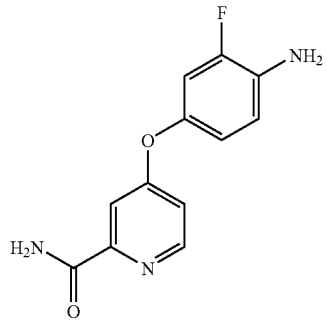

(Method 1)

4-Amino-3-fluorophenol (5.7 g) was dissolved in dimethyl sulfoxide (57 ml) under a nitrogen stream, potassium tert-butoxide (5.6 g) was added at room temperature, and the reaction mixture was stirred for 15 minutes. 4-Chloropyridine-2-carboxamide (5.0 g) was added to the reaction mixture, followed by stirring in an oil bath at 80° C. (external temperature) under a nitrogen stream for 50 minutes. The reaction mixture was allowed to cool down to room temperature. A 1N aqueous solution of sodium hydroxide (85.5 ml) was added to the reaction mixture, followed by stirring. The precipitated solid was collected by filtration and washed with water. The residue was dried under aeration and then dried by hot air at 100° C. to give the title compound (5.88 g, 74.3%) as pale brown powder.

$^1$H-NMR Spectrum (DMSO-$d_6$) δ (ppm): 5.18-5.30 (2H, m), 6.80 (1H, dd, J=2.4, 8.4 Hz), 6.81-6.90 (1H, m), 7.02 (1H, dd, J=2.4, 11.6 Hz), 6.99-7.14 (1H, m), 7.32-7.39 (1H, m), 7.69 (1H, brs), 8.10 (1H, brs), 8.48 (1H, m).

(Method 2)

Potassium tert-butoxide (214 g) was dissolved in dimethyl sulfoxide (750 ml) and tetrahydrofuran (250 ml) under a nitrogen stream, and a solution of 4-amino-3-fluorophenol ½ naphthalene-2,6-disulfonate (242 g) and 4-chloropyridine-2-carboxamide (100 g) in dimethyl sulfoxide (1000 ml) was added dropwise to the solution with stirring and cooling on ice. The reaction mixture was stirred at room temperature for 30 minutes, then in an oil bath at 90° C. (external temperature) for 2 hours. The reaction mixture was allowed to cool down to room temperature, and water (3000 ml) was added, and the reaction mixture was stirred for 2 hours. The precipitated crystals were collected by filtration, and washed with water (500 ml, twice). The residue was suspended in water (2000 ml), stirred for 30 minutes, collected by filtration again, and washed with water (500 ml, twice). Drying by hot air at 60° C. gave the title compound (119 g, 75.3%).

Example 3

1-[4-(2-Carbamoylpyridin-4-yloxy-2-fluorophenyl-carbamoyl]cyclopropanecarboxylic acid benzyl ester

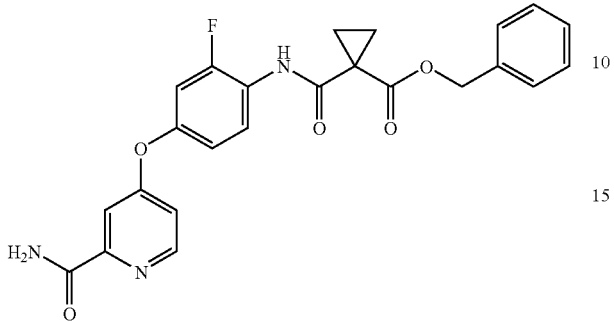

(Method 1)

A mixture of 1-(benzyloxycarbonyl)cyclopropanecarboxylic acid (11.5 g), tetrahydrofuran (148 ml) and N-methylmorpholine (10.9 g) was stirred with cooling on ice. Thionyl chloride (6.19 g) was added dropwise at the internal temperature between 4.4° C. and 25.2° C., and the reaction mixture was stirred for 47 minutes. 4-(4-Amino-3-fluorophenoxy)pyridine-2-carboxamide (9.89 g) was added over 2 minutes at the internal temperature between 1.9° C. and 13.4° C., and the reaction mixture was stirred for 4 hours and 40 minutes with keeping the internal temperature between 3° C. and 6° C. The reaction mixture was partitioned after the addition of ethyl acetate (346 ml), a 2N aqueous solution of sodium hydroxide (100 ml), tetrahydrofuran (49 ml) and water (20 ml). The organic layer was washed twice with a 5% aqueous solution of sodium chloride (49 ml). The organic layer was concentrated under reduced pressure, and the precipitated crystals were triturated with a mixed solvent of ethyl acetate (15 ml) and heptane (15 ml). This was filtered and washed with a mixed solvent of ethyl acetate (5 ml) and heptane (5 ml) to give the title compound (13.44 g).

$^1$H-NMR Spectrum (DMSO-$d_6$) δ (ppm): 1.58 (4H, s), 5.20 (2H, s), 7.06-7.11 (1H, m), 7.19-7.23 (1H, m), 7.31-7.44 (7H, m), 7.72 (1H, s), 8.13 (1H, s), 8.51-8.56 (1H, m), 8.75 (1H, t, J=8.4 Hz), 10.71 (1H, s).

(Method 2)

N-Methylmorpholine (12.8 g) was added to a solution of 2-chloro-4,6-dimethoxy-1,3,5-triazine (24.5 g) in tetrahydrofuran (625 ml) with stirring at room temperature, at the internal temperature between 25.0° C. and 27.5° C. After stirring at room temperature for 50 minutes, 1-(benzyloxycarbonyl)cyclopropanecarboxylic acid (24.5 g) was added at the same temperature. After 10 minutes, 4-(4-amino-3-fluorophenoxy)pyridine-2-carboxamide (25.5 g) was added with stirring at room temperature. The reaction mixture was stirred at room temperature for 12 hours and 50 minutes. A 5% aqueous solution of sodium hydrogencarbonate (1250 ml) was added to the reaction mixture, followed by stirring at room temperature for 3 hours. The mixture was filtered, and the collected crystals were washed with water (100 ml). The crystals were dried at 60° C. for 13 hours to give the target title compound (45.4 g).

Example 4

1-[4-(2-Aminopyridin-4-yloxy)-2-fluorophenylcarbamoyl]cyclopropanecarboxylic acid benzyl ester

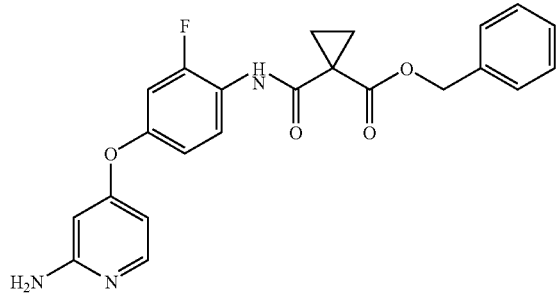

(Method 1)

1-[4-(2-Carbamoylpyridin-4-yloxy)-2-fluorophenylcarbamoyl]-cyclopropanecarboxylic acid benzyl ester (2 g) was dissolved in N,N-dimethylformamide (20 ml) at room temperature, and water (0.481 ml) was added. Iodobenzene diacetate (2.87 g) was added at room temperature with stirring, and the reaction mixture was stirred for 2.5 hours. Water (40 ml) was added to the reaction mixture, and the reaction was quenched by the addition of a 2N aqueous solution of sodium hydroxide until pH became 11 and ethyl acetate was added and the layers were separated. The organic layer was washed with water and a 5% aqueous solution of sodium chloride, dried over magnesium sulfate, filtered, and concentrated. The resultant crude brown oil was purified by silica gel column chromatography (eluent; heptane:ethyl acetate=1:1, then 1:2) to give the title compound (819 mg) as cream crystals.

$^1$H-NMR Spectrum (DMSO-$d_6$) δ (ppm): 1.50-1.60 (4H, brs), 3.30 (2H, s), 5.19 (2H, s), 5.85 (1H, d, J=2.4 Hz), 5.96 (1H, m), 6.15 (1H, dd, J=2.4 Hz, 6.4 Hz), 6.96 (1H, m), 7.20 (1H, dd, J=2.4 Hz, 11.2 Hz), 7.30-7.42 (4H, m), 7.81 (1H, d, J=5.6 Hz), 7.96 (1H, m), 10.62 (1H, s).

(Method 2)

1-[4-(2-Carbamoylpyridin-4-yloxy)-2-fluorophenylcarbamoyl]cyclopropanecarboxylic acid benzyl ester (10 g) was dissolved in N,N-dimethylformamide (100 ml) at room temperature, and water (2.41 ml) was added. Iodobenzene diacetate (7.91 g) was added with stirring at room temperature, the reaction mixture was stirred for 3 hours, iodobenzene diacetate (360 mg) was further added, and the reaction mixture was stirred for 2 hours. Ethyl acetate (100 ml) and a 5% aqueous solution of sodium hydrogencarbonate (100 g) were added to the reaction mixture, and layers were separated. The organic layer was washed with water, dried over magnesium sulfate, filtered, and concentrated. Ethyl acetate (30 ml) was added to the resultant crude crystals, and the mixture was heated and stirred at 60° C. After confirming the crystals were dissolved, the mixture was allowed to cool down to room temperature. Seed crystals obtained in Method 1 (50 mg) were added, and the mixture was stirred for 30 minutes. After confirming the precipitation of the crystals, heptane (100 ml) was added, and the mixture was further stirred for 30 minutes. The crystals were collected by filtration and dried to give the title compound (6.84 g).

(Method 3)

1-[4-(2-Carbamoylpyridin-4-yloxy)-2-fluorophenylcarbamoyl]cyclopropanecarboxylic acid benzyl ester (17.9 g) was dissolved in N-methyl-2-pyrrolidone (125 ml) at room temperature, and water (7.2 ml) was added. Iodobenzene diacetate (14.1 g) was added with stirring at room temperature, followed by stirring for 4 hours and 7 minutes. Ethyl acetate (268 ml) and a 1N aqueous solution of sodium hydroxide (179 ml) were added to the reaction mixture, and the layers were separated. The organic layer was washed with a 5% aqueous solution of sodium chloride (179 ml) three times and water (179 ml) once, dried over magnesium sulfate, filtered, and concentrated. Toluene (72 ml) was added to the resultant crystals, and the mixture was heated and stirred at 90° C. After confirming the crystals were dissolved, the mixture was allowed to cool down to room temperature. The precipitated crystals were collected by filtration, washed with toluene (18 ml), and dried under reduced pressure at 50° C. for 4 hours to give the title compound (11.9 g) as pale orange crystals.

Example 5

1-[2-Fluoro-4-(2-phenoxycarbonylaminopyridin-4-yloxy)phenylcarbamoyl]cyclopropanecarboxylic acid benzyl ester

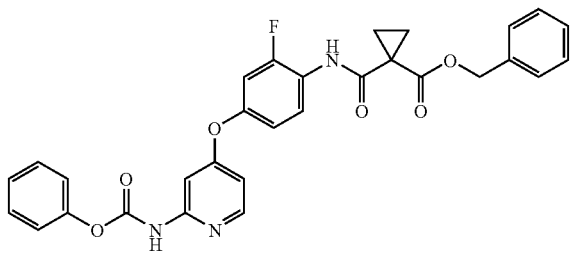

Tetrahydrofuran (41 ml), acetonitrile (41 ml) and pyridine (2.07 g) was added to 1-[4-(2-aminopyridin-4-yloxy)-2-fluorophenylcarbamoyl]cyclopropanecarboxylic acid benzyl ester (6.0 g, content 5.51 g), which was dissolved by stirring. Phenyl chloroformate (4.1 g) was added dropwise to this solution with cooling on ice at the internal temperature between 8.8° C. and 14.9° C. The reaction mixture was stirred at the same temperature for 2 hours and 9 minutes, then at room temperature for 3 hours and 5 minutes. The precipitate was collected by filtration, washed with a mixed solvent of tetrahydrofuran and acetonitrile (2:1, 16 ml), and dried under aeration to give the target title compound (6.39 g).

Example 6

1-[2-Fluoro-4-(2-{[4-(4-methylpiperazin-1-yl)piperidine-1-carbonyl]amino}piperidin-4-yloxy)phenylcarbamoyl]cyclopropanecarboxylic acid benzyl ester

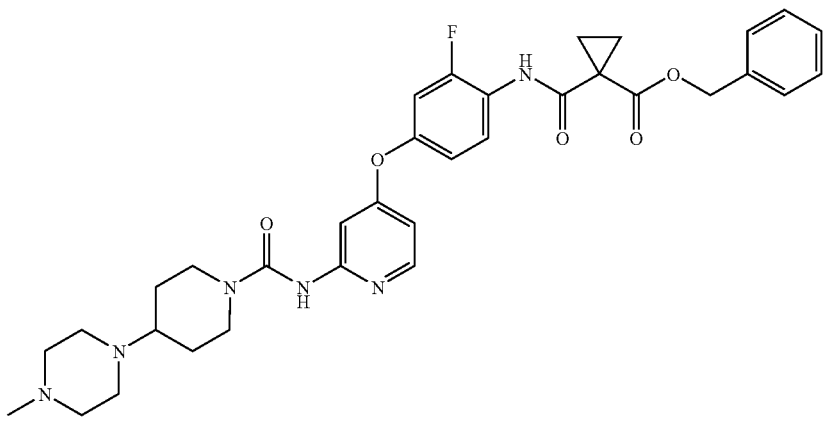

(Method 1)

Potassium carbonate (772 mg) was added to a mixture of 1-[2-fluoro-4-(2-phenoxycarbonylaminopyridin-4-yloxy)phenylcarbamoyl]cyclopropanecarboxylic acid benzyl ester (2.75 g) and N,N-dimethylformamide (13.8 ml) was added, followed by stirring. 1-Methyl-4-(piperidin-4-yl)piperazine (1.02 g) was added, followed by stirring for 6 hours. The reaction mixture was partitioned after the addition of ethyl acetate (41 ml) and water (27.5 ml). The resultant organic layer was washed with water (13.8 ml, three times), dried over sodium sulfate, and filtered, and the filtrate was concentrated. The resultant residue was purified by silica gel column chromatography (Fuji Silysia NH, eluent; ethyl acetate:methanol=30:1). The eluate was concentrated under reduced pressure, and the precipitate appeared by the addition of tert-butyl methyl ether (3 ml) and the application of a stimulus. tert-Butyl methyl ether (40 ml) was further added, followed by stirring overnight. The resultant precipitate was collected by filtration, washed with tert-butyl methyl ether (3 ml), and dried under aeration to give the target title compound (1.61 g).

$^1$H-NMR Spectrum (DMSO-$d_6$) δ (ppm): 1.20-1.34 (2H, m), 1.57 (4H, s), 1.72 (2H, d, J=10.8 Hz), 2.12 (3H, s), 2.18-2.40 (4H, m), 2.45 (3H, brs), 2.74 (2H, t, J=11.6 Hz), 3.30 (2H, s), 4.10 (2H, d, J=13.6 Hz), 5.20 (2H, s), 6.43-6.55 (1H, m), 6.97-7.10 (1H, m), 7.22-7.29 (1H, m), 7.30-7.44 (6H, m), 7.98-8.08 (1H, m), 8.13 (1H, d, J=6.0 Hz), 9.21 (1H, s), 10.67 (1H, s).

(Method 2)

1-Methyl-4-(piperidin-4-yl)piperazine (1.46 g) was added to a mixture of 1-[2-fluoro-4-(2-phenoxycarbonylaminopyridin-4-yloxy)phenylcarbamoyl]cyclopropanecarboxylic acid benzyl ester (3.60 g) and N-methyl-2-pyrrolidone (25 ml), followed by stirring with heating at 40° C. for 1 hour and 51 minutes. The reaction mixture was partitioned after the addition of ethyl acetate (180 mL) and water (90 mL). The resultant organic layer was washed with water (36 ml, twice) and a 10% aqueous solution of sodium chloride (36 ml), dried over anhydrous magnesium sulfate (10 g), and filtered, and the filtrate was concentrated. The resultant residue was purified by silica gel column chromatography (Fuji Silysia NH, eluent; heptane:ethyl acetate=1:1, ethyl acetate, ethyl acetate: isopropyl alcohol=9:1). The eluate was concentrated under reduced pressure, and the precipitate appeared after the addition of tert-butyl methyl ether (60 ml) and seed crystals obtained in (Method 1). The resultant precipitate was collected by filtration, washed with tert-butyl methyl ether (10 ml), and dried under reduced pressure at 40° C. for 2 hours to give the target title compound (2.57 g).

Example 7

1-[2-Fluoro-4-(2-{[4-(4-methylpiperazin-1-yl)piperidine-1-carbonyl]amino}piperidin-4-yloxy)phenylcarbamoyl]cyclopropanecarboxylic acid benzyl ester trihydrochloride nopyridin-4-yloxy)phenylcarbamoyl]cyclopropanecarboxylic acid benzyl ester (2.0 g) and N-methyl-2-pyrrolidone (14 ml), followed by stirring at 40° C. for 2 hours and 31 minutes. The reaction mixture was partitioned after the addition of ethyl acetate (60 ml) and water (40 ml). The organic layer was washed with a 5% aqueous solution of sodium chloride (10 ml, three times) and water (10 ml). 4N Hydrochloric acid in ethyl acetate (0.5 ml) was added to a portion (10 ml) of the resultant organic layer, and seed crystals obtained in (Method 1) were added. Isopropyl alcohol (1 ml) was added, and the precipitate appeared after sonication. The resultant precipitate was filtered, and washed with ethyl acetate (2 ml) to give the title compound (322 mg).

(Method 3)

1-Methyl-4-(piperidin-4-yl)piperazine (2.68 g) was added to a mixture of 1-[2-fluoro-4-(2-phenoxycarbonylaminopyridin-4-yloxy)phenylcarbamoyl]cyclopropanecarboxylic acid benzyl ester (6.63 g) and N-methyl-2-pyrrolidone (33 ml), followed by stirring at 40° C. for 2 hours and 10 minutes. The reaction mixture was partitioned after the addition of ethyl acetate (132 ml) and water (99 ml). The organic layer was washed with a 5% aqueous solution of sodium chloride

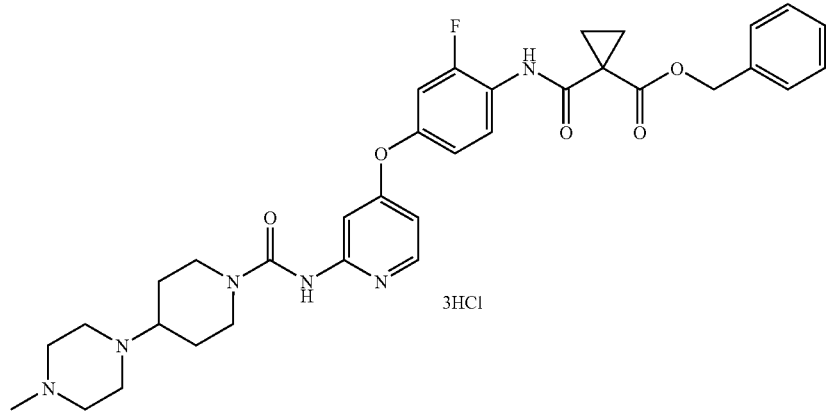

(Method 1)

1-[2-Fluoro-4-(2-{[4-(4-methylpiperazin-1-yl)piperidine-1-carbonyl]amino}piperidin-4-yloxy)phenylcarbamoyl]cyclopropanecarboxylic acid benzyl ester (189 mg) was dissolved in ethyl acetate (6 ml), and 4N hydrochloric acid in ethyl acetate (0.3 ml) was added. The resultant mixture was concentrated under reduced pressure, and methanol (0.5 ml) and ethyl acetate (4 ml) was added. The precipitate obtained by filtration was hygroscopic, thus it was collected using methanol (10 ml). The collected solution was again concentrated under reduced pressure, and methanol (0.5 ml) and tert-butyl methyl ether (4 ml) was added. The precipitate was filtered to give the title compound (102 mg).

$^1$H-NMR Spectrum (DMSO-$d_6$) δ (ppm): 1.58 (4H, s), 1.60-1.74 (2H, m), 2.17 (2H, d, J=10.4 Hz), 2.83 (3H, s), 2.91 (2H, t, J=12.4 Hz), 3.50-3.57 (9H, m), 4.39 (2H, d, J=12.8 Hz), 5.20 (2H, s), 7.03-7.09 (1H, m), 7.13-7.19 (1H, m), 7.30-7.42 (6H, m), 7.46 (1H, dd, J=2.4, 8.8 Hz), 8.14 (1H, t, J=8.8 Hz), 8.30 (1H, d, J=7.2 Hz), 10.78 (1H, s), 10.93 (1H, brs).

(Method 2)

1-Methyl-4-(piperidin-4-yl)piperazine (812 mg) was added to a mixture of 1-[2-fluoro-4-(2-phenoxycarbonylami- (33 ml, twice) and water (33 ml). 4N hydrochloric acid in ethyl acetate (10 ml) was added to isopropyl alcohol (13 ml), then the above washed organic layer (8 ml) was added dropwise thereto, the seed crystals obtained in (Method 2) was added, and the organic layer was father added dropwise. During the addition, isopropyl alcohol (13 ml) was added, and the mixture was treated with sonication, and the drop continued. After the completion of the addition, the mixture was stirred for 5 hours and 38 minutes. The precipitate was filtered, washed with a mixed solvent of ethyl acetate and isopropyl alcohol (5:1, 20 ml), and the solvent was replaced by ethyl acetate (20 ml). Drying under aeration under a nitrogen stream and drying under reduced pressure at 40° C. for 2 hours gave the target title compound (6.12 g).

(Method 4)

A solution of 1-methyl-4-(piperidin-4-yl)piperazine in N-methyl-2-pyrrolidone (24.8%, 26.3 g) was added to a mixture of 1-[2-fluoro-4-(2-phenoxycarbonylaminopyridin-4-yloxy)phenylcarbamoyl]cyclopropanecarboxylic acid benzyl ester (16.1 g) and N-methyl-2-pyrrolidone (46 ml), washing with N-methyl-2-pyrrolidone (15 ml) was performed. The mixture was stirred at 37° C. for 1 hour and 52 minutes. The reaction mixture was partitioned after the addition of ethyl acetate (242 ml) and water (242 ml). The organic layer was washed with 1N hydrochloric acid (81 ml). The aqueous layer was separated, ethyl acetate (161 ml) was added, and a 2N aqueous solution of sodium hydroxide (81 mL) was added, and the partition was performed. The organic layer was separated and washed with a 1% aqueous solution of sodium chloride (81 g), and the organic layer (151.3 g) was collected. A portion (104.2 g) of the above organic layer was added to ethanol (48 ml), and concentrated hydrochloric acid (7.41 ml) was added to the mixture with stirring on ice. A portion (ca. 15 ml) of the rest of the organic layer was added and seed crystals (48.3 mg) were added, and the mixture was stirred at room temperature for 1 hour and 14 minutes. The whole amount of the rest of the organic layer was added dropwise over 29 minutes, followed by stirring for 16 hours and 19 minutes. The precipitate was removed by filtration, washed with a mixed solvent of ethyl acetate and ethanol (3:1, 32.4 ml), and the solvent was replaced by ethyl acetate (32.2 ml). Drying under aeration under a nitrogen stream and drying under reduced pressure at 40° C. for 2 hours and 20 minutes gave the title compound (15.0 g).

Example 8

1-[2-Fluoro-4-(2-{[4-(4-methylpiperazin-1-yl)piperidine-1-carbonyl]amino}pyridin-4-yloxy)phenylcarbamoyl]cyclopropanecarboxylic acid

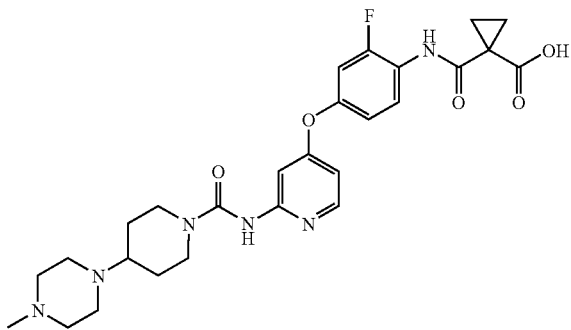

(Method 1)
1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester (800 mg) was dissolved in a mixed solvent of tetrahydrofuran (4 ml) and ethanol (4 ml), palladium on carbon (400 mg) was added, and the mixture was stirred at room temperature under a hydrogen atmosphere (0.15 MPa) for 4 hours. Water (4 ml) was added to the reaction mixture, which was filtered, and the residue was washed with a 50% aqueous ethanol (8 ml) and water (4 ml), and the filtrate was concentrated. Tetrahydrofuran (8 ml) and ethanol (8 ml) was added to the residue, which was concentrated. Tetrahydrofuran (8 ml), ethyl acetate (8 ml) and ethanol (2 ml) were added to the residue, which was concentrated. Tetrahydrofuran (8 ml) and ethanol (16 ml) were added to the residue, which was concentrated to precipitate crystals. The crystals were suspended in tetrahydrofuran (16 ml), stirred at room temperature for 40 minutes, filtered, and dried to give the title compound (550 mg) as white crystals.
$^1$H-NMR Spectrum (DMSO-$d_6$) δ (ppm): 1.15-1.23 (2H, m), 1.24-1.38 (4H, m), 1.70-1.80 (2H, m), 2.41-2.50 (2H, brs), 2.50 (3H, s), 2.60-2.90 (9H, m), 4.10-4.18 (2H, m), 6.60 (1H, dd, J=2:4 Hz, 5.6 Hz), 6.93 (1H, d, J=8.8 Hz), 7.17 (1H, dd, J=2.4 Hz, 11.6 Hz), 7.33 (1H, d, J=2.4 Hz), 8.10 (1H, d, J=5.6 Hz), 8.35 (1H, t, J=8.8 Hz), 9.21 (1H, s).

(Method 2)
1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester (500 mg) was dissolved in a mixed solvent of tetrahydrofuran (2.5 ml), ethanol (2.5 ml) and water (1.5 ml), palladium on carbon (100 mg) was added, and the mixture was stirred at room temperature under a hydrogen atmosphere (0.15 MPa) for 3 hours. The reaction mixture was filtered, and the residue was washed with a 90% aqueous ethanol (1 ml), and the filtrate was concentrated. Addition of ethanol to the residue and subsequent concentration were repeated three times. Ethanol (2.5 ml), tetrahydrofuran (2.5 ml) and the seed crystals obtained in (Method 1) were added to the residue, and the mixture was stirred at room temperature for 1 hour. Ethyl acetate (5 ml) was added, and the mixture was further stirred for 1 hour. The crystals were filtered and dried to give the title compound (420 mg) as white crystals.

(Method 3)
1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester hydrochloride (2 g) was dissolved in water (20 ml) and ethyl acetate (20 ml), and a 2N aqueous solution of sodium hydroxide (4 ml) was added, and the layers were separated. The organic layer was washed with water and concentrated. Addition of tetrahydrofuran and subsequent concentration was repeated three times. The residue was dissolved in a mixed solvent of tetrahydrofuran (8 ml) and water (1.6 ml), and palladium on carbon (200 mg) was added, and the mixture was stirred at room temperature under a hydrogen atmosphere (0.2 MPa) for 5 hours. Tetrahydrofuran (4 ml) and methanol (6 ml) were added to the reaction mixture, which was filtered. The residue was washed with 90% aqueous methanol (3 ml). Tetrahydrofuran (12 ml) and the seed crystals obtained in (Method 1) were added to the filtrate, and the mixture was stirred at room temperature for 1 hour. Ethyl acetate (32 ml) was added, and the mixture was stirred for 14 hours. The crystals were filtered and dried to give the title compound (1.2 g) as white crystals.

Example 8-2

1-[2-Fluoro-4-(2-{[4-(4-methylpiperazin-1-yl)piperidine-1-carbonyl]amino}pyridin-4-yloxy)phenylcarbamoyl]cyclopropanecarboxylic acid trihydrochloride

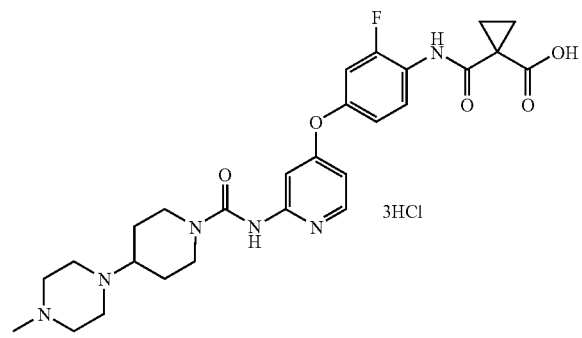

(Method 1)

1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester trihydrochloride (2 g) was dissolved in a mixed solvent of water (4 ml) and ethanol (8 ml), palladium on carbon (100 mg) was added, and the mixture was stirred at room temperature under a hydrogen atmosphere (ca. 1 atmospheric pressure) for 5 hours and 10 minutes. The reaction mixture was filtered, and the residue was washed with a mixed solvent of water (1 ml) and ethanol (2 ml). Ethanol (20 ml) was added to the filtrate, which was concentrated. Addition of ethanol (10 ml) to the residue and subsequent concentrate were repeated four times. The mixture was filtered with heating and ethyl acetate (40 ml) was added dropwise with stirring at the same time. After stirring at room temperature for 25 hours and 30 minutes, the crystals were filtered with washing with a mixed solvent of ethanol (2 ml) and ethyl acetate (2 ml) and dried to give the title compound (1.56 g) as a white solid.

$^1$H-NMR Spectrum (DMSO-$d_6$) δ (ppm): 1.50-1.78 (8H, m), 2.04-2.22 (2H, m), 2.46 (3H, s), 2.80-3.90 (9H, m), 4.22-4.40 (2H, m), 7.01 (1H, brs), 7.13 (1H, d, J=9.6 Hz), 7.22 (1H, s), 7.43 (1H, d, J=12.4 Hz), 8.22-8.32 (2H, m), 11.30 (1H, s).

(Method 2)

1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester trihydrochloride (5 g) was dissolved in a mixed solvent of water (10 ml) and ethanol (20 ml), and palladium on carbon (250 mg) was added, and the mixture was stirred at room temperature under a hydrogen atmosphere (0.2 MPa) for 7 hours and 50 minutes. The reaction mixture was filtered, and the residue was washed with a mixed solvent of water (6 ml) and ethanol (10 ml). Ethanol (50 ml) was added to the filtrate, which was azeotropically distilled off and concentrated, and water (0.6 g) and ethanol (8.3 ml) were added. 2-Propanol (10 ml) was added to the solution, followed by stirring at room temperature for 5 minutes. 1-[2-Fluoro-4-(2-{[4-(4-methylpiperazin-1-yl)piperidine-1-carbonyl]amino}pyridin-4-yloxy)phenylcarbamoyl]cyclopropanecarboxylic acid trihydrochloride (150 mg) was added, followed by stirring for 13 hours and 45 minutes. 2-Propanol (50 ml) was further added, and the mixture was stirred at room temperature for 24 hours and 35 minutes. The crystals were filtered and dried to give the title compound (4.26 g) as a white solid.

Example 9

N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide

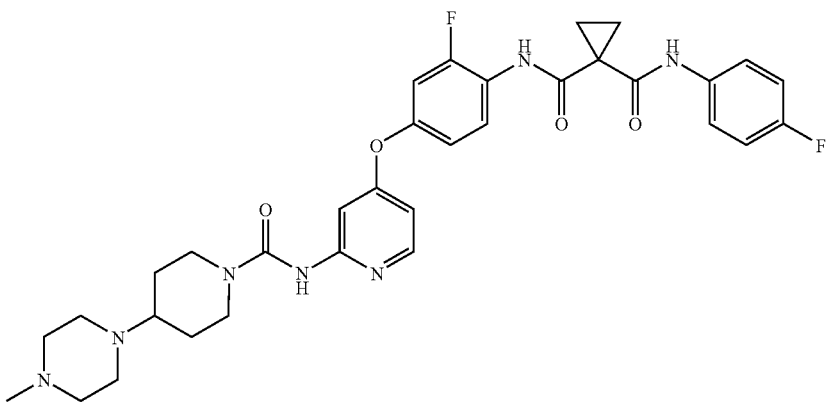

(Method 1)

4-(4,6-Dimethoxy[1,3,5]triazin-2-yl)-4-methylmorpholinium chloride hydrate (164 mg) was added to a suspension of 1-[2-fluoro-4-(2-{[4-(4-methylpiperazin-1-yl)piperidine-1-carbonyl]amino}pyridin-4-yloxy)phenylcarbamoyl]cyclopropanecarboxylic acid (100 mg) in mixture of tetrahydrofuran (1 ml), N,N-dimethylformamide (0.2 ml) and 4-fluoroaniline (0.0526 ml), followed by stirring at room temperature for 2.5 hours. A 5% aqueous solution of sodium hydrogencarbonate was added to the reaction mixture to quench the reaction, and ethyl acetate was added and the layers were separated. The organic layer was washed with water and concentrated. The residue was purified by silica gel column chromatography (Fuji Silysia NH, eluent; ethyl acetate, ethyl acetate:methanol=95:5). The eluate was concentrated. Ethyl acetate (2 ml) was added to the resultant residue, followed by stirring at room temperature for 30 minutes. Heptane (2 ml) was added, and the mixture was stirred for 30 minutes. The crystals were collected by filtration and dried to give the title compound (74 mg) as white crystals.

$^1$H-NMR Spectrum (DMSO-$d_6$) δ (ppm): 1.22-1.33 (2H, m), 1.54-1.63 (4H, m), 1.68-1.78 (2H, m), 2.12 (3H, s), 2.12-2.40 (5H, m), 2.40-2.60 (4H, m), 2.68-2.78 (2H, m), 4.06-4.14 (2H, m), 6.60 (1H, dd, J=2.4 Hz, 5.6 Hz), 7.00 (1H, m), 7.19 (2H, t, J=8 Hz), 7.22 (1H, dd, J=2.4 Hz, 11.2 Hz), 7.40 (1H, s), 7.61 (2H, dd, J=5.2 Hz, 8 Hz), 7.93 (1H, t, J=8.8 Hz), 8.13 (1H, d, J=5.6 Hz), 9.21 (1H, s), 9.90 (1H, brs), 10.55 (1H, brs).

(Method 2)

4-(4,6-Dimethoxy[1,3,5]triazin-2-yl)-4-methylmorpholinium chloride hydrate was added to a suspension of 1-[2-fluoro-4-(2-{[4-(4-methylpiperazin-1-yl)-piperidine-1-carbonyl]-amino}-pyridin-4-yloxy)phenylcarbamoyl]-cyclopropanecarboxylic acid (500 mg, 0.925 mmol) in a mixture of tetrahydrofuran (4.5 ml), N,N-dimethylformamide (1 ml) and 4-fluoroaniline (0.131 ml), followed by stirring at room temperature for 16 hours. Ethyl acetate (7.5 ml) was added to the reaction mixture, and a 5% aqueous solution of sodium hydrogencarbonate (7.5 ml) was added to quench the reaction, and the layers were separated. 1N hydrochloric acid (5 ml) was added to the organic layer, and the layers were separated. Tetrahydrofuran (7.5 ml) was added to the aqueous layer, and a 2N aqueous solution of sodium hydroxide (3 ml) was added to effect neutralization, and ethyl acetate (7.5 ml) was added and the layers were separated. The organic layer was washed with water and concentrated. Addition of ethyl acetate to the residue and subsequent concentration were repeated three times.

To the residue was added ethyl acetate until the whole weight reached to 2.34 g, and the seed crystals obtained in (Method 1) was added, and the mixture was stirred at room temperature for 30 minutes. Ethyl acetate (2.5 ml) was added, and the mixture was stirred for 1 hour, heptane (5 ml) was added and the mixture was stirred for 2 hours. The crystals were collected by filtration and dried to give the title compound (427 mg) as white crystals.

(Method 3)

N-Methylmorpholine (419 g) was added to a solution of 2-chloro-4,6-dimethoxy-1,3,5-triazine (238 g) in a mixture of tetrahydrofuran (4400 g) and 2-propanol (2159 g) with stirring, and tetrahydrofuran (122 g) was used for washing, and the mixture was stirred at 25° C. for 33 minutes. 1-[2-Fluoro-4-(2-{[4-(4-methylpiperazin-1-yl)piperidine-1-carbonyl]amino}piperidin-4-yloxy)phenylcarbamoyl]-cyclopropanecarboxylic acid benzyl ester trihydrochloride (550 g) was added to the reaction mixture, tetrahydrofuran (245 g) was used for washing, 4-fluoroaniline (132 g) was added, tetrahydrofuran (122 g) was used for washing, and the mixture was stirred at 25° C. for 4 hours and 20 minutes. Isopropyl acetate (7194 g) and a 1N aqueous solution of hydrochloric acid (5593 g) were added to the reaction mixture, and the layers were separated. Tetrahydrofuran (1147 g) and isopropyl acetate (7194 g) were added to the aqueous layer, a 2N aqueous solution of sodium hydroxide (5401 g) was added to effect neutralization, and the layers were separated. The organic layer was washed with a 5% aqueous solution of sodium chloride (1650 g) twice, and water (1650 g) once, and concentrated until the liquid volume became ca. 3 L. Isopropyl acetate (1440 g) was added to the concentrated solution, and the mixture was stirred at 25° C. for 1 hour and 20 minutes. Isopropyl acetate (959 g) was added, and the mixture was stirred at the same temperature for 3 hours and 7 minutes. Isopropyl acetate (2398 g) was added, and the mixture was stirred at the same temperature for 16 hours and 28 minutes. The precipitated crystals were collected by filtration and dried to give the title compound (408 g) as white crystals.

Example 10

4-(4-Amino-2,5-difluorophenyl)pyridine-2-carboxamide

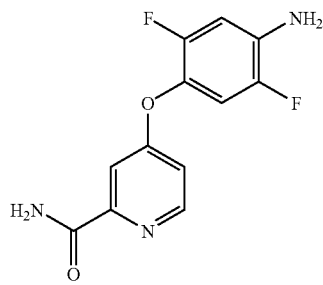

4-Amino-2,5-difluorophenol (4.95 g) was dissolved in dimethyl sulfoxide (50 ml) under a nitrogen stream, and potassium tert-butoxide (4.05 g) was added at room temperature, and the mixture was stirred for 25 minutes. 4-Chloropyridine-2-carboxamide (2.70 g) was added to the mixture, which was stirred at 80° C. for 2.5 hours. The reaction mixture was allowed to cool down to room temperature, and a 1N aqueous solution of sodium hydroxide (74.25 ml) was added, and the mixture was stirred for 10 hours. The precipitated solid was collected by filtration, and the resultant solid was washed with water. The solid was dried by hot air at 100° C. for 24 hours to give the title compound (3.38 g, 74%) as purple powder.

$^1$H-NMR Spectrum (DMSO-$d_6$) δ (ppm): 5.57 (2H, d, J=6.0 Hz), 6.75-6.80 (1H, m), 7.17-7.20 (1H, m), 7.26 (1H, dd, J=7.2, 10.8 Hz), 7.38 (1H, m), 7.73 (1H, s), 8.14 (1H, s), 8.52 (1H, d, J=5.6 Hz).

ESI-MS (m/z): 288[M+Na]$^+$.

Example 11

Benzyl 1-{[(4-{[2-(aminocarbonyl)pyridin-4-yl]oxy}-2,5-difluorophenyl)amino]carbonyl}cyclopropanecarboxylate

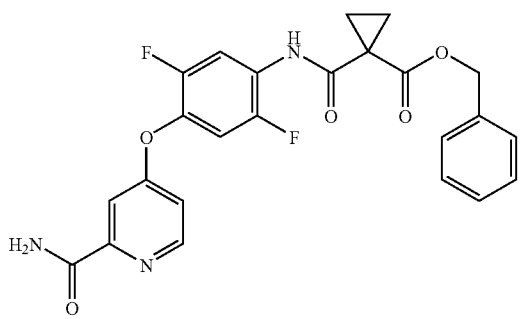

1-[(Benzyloxy)carbonyl]cyclopropanecarboxylic acid (1.04 g) was dissolved in tetrahydrofuran (15 ml) under a nitrogen atmosphere. N-Methylmorpholine (0.520 ml) was added at 0° C., and the mixture was stirred for 15 minutes. Thionyl chloride (0.345 ml) was added to the mixture at 0° C., and the mixture was stirred at the same temperature for 30 minutes. 4-(4-Amino-2,5-difluorophenoxy)pyridine-2-carboxamide (500 mg) and N-methylmorpholine (0.520 ml) was added, and the mixture was stirred at room temperature for 2 hours and 50 minutes. The reaction mixture was partitioned after the addition of a 1N aqueous solution of sodium hydroxide (15 ml) and ethyl acetate (20 ml). The organic layer was washed with a 1N aqueous solution of sodium hydroxide (15 ml), water (15 ml) and brine (15 ml), and dried over anhydrous magnesium sulfate. The desiccant was removed by filtration, and the filtrate was concentrated under reduced pressure. The resultant residue was purified by silica gel column chromatography (Fuji Silysia NH, eluent; heptane: ethyl acetate=1:1, then 1:2). The fractions containing the target compound was concentrated under reduced pressure to give the title compound (822.7 mg, 93%) as white powder.

$^1$H-NMR Spectrum (DMSO-$d_6$) δ (ppm): 1.58-1.63 (4H, m), 5.20 (2H, s), 7.24-7.27 (1H, m), 7.30-7.42 (5H, m), 7.43 (1H, d, J=2.8 Hz), 7.63-7.71 (1H, m), 7.72-7.78 (1H, m), 8.13-8.22 (2H, m), 8.56 (1H, d, J=5.6 Hz), 10.93 (1H, brs).

ESI-MS (m/z): 490[M+Na]$^+$.

Example 12

Benzyl 1-[({4-[(2-aminopyridin-4-yl)oxy]-2,5-difluorophenyl}amino)carbonyl]cyclopropanecarboxylate

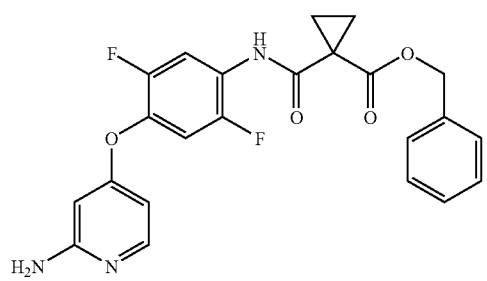

Benzyl 1-{[(4-{[2-(aminocarbonyl)pyridin-4-yl]oxy}-2,5-difluorophenyl)amino]carbonyl}cyclopropanecarboxylate (1.55 g) was dissolved in N,N-dimethylformamide (33 ml). Water (0.299 ml) and iodobenzene diacetate (1.18 g) were added at room temperature, and the mixture was stirred for 15 hours and 20 minutes. Iodobenzene diacetate (215 mg) was added again and the mixture was stirred for 2 hours and 20 minutes. Water (150 ml) was added to the mixture, and the mixture was stirred for 1 hour, and partitioned after the addition of a saturated aqueous solution of sodium hydrogencarbonate (200 ml) and ethyl acetate (300 ml). The organic layer was washed with water (200 ml, twice) and brine (150 ml), and dried over anhydrous magnesium sulfate. The desiccant was removed by filtration, and the filtrate was concentrated under reduced pressure. The resultant residue was purified by silica gel column chromatography (Fuji Silysia NH, eluent; heptane:ethyl acetate=1:2). The fractions containing the target compound were concentrated under reduced pressure to give the title compound (1.217 g, 83%) as a pale yellow solid.

$^1$H-NMR Spectrum (DMSO-$d_6$) δ (ppm): 1.54-1.65 (4H, m), 5.19 (2H, s), 5.83 (1H, d, J=2.0 Hz), 5.99 (2H, brs), 6.18 (1H, dd, J=2.4, 5.6 Hz), 7.30-7.45 (5H, m), 7.52 (1H, dd, J=7.2, 10.8 Hz), 7.82 (1H, d, J=5.6 Hz), 8.05-8.20 (1H, m), 10.86 (1H, brs).

ESI-MS (m/z): 440[M+H]$^+$.

Example 13

Benzyl 1-({[4-({2-[(phenoxycarbonyl)amino]pyridin-4-yl}oxy)-2,5-difluorophenyl]amino}carbonyl)cyclopropanecarboxylate

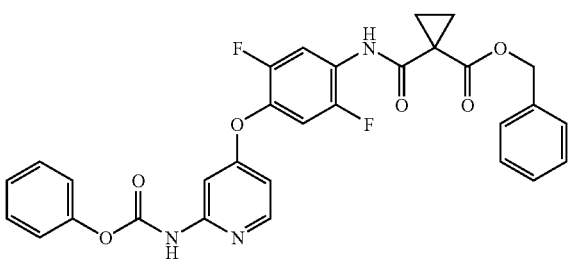

Benzyl 1-[({4-[(2-aminopyridin-4-yl)oxy]-2,5-difluorophenyl}amino)carbonyl]cyclopropanecarboxylate (1.15 g) was dissolved in tetrahydrofuran (12 ml) under a nitrogen atmosphere. Pyridine (0.424 ml) and phenyl chloroformate (0.657 ml) were added at room temperature, and the mixture was stirred for 20 minutes. A saturated aqueous solution of sodium hydrogencarbonate (36 ml) and hexane (36 ml) were added to the mixture, and the mixture was stirred for 55 minutes. The precipitated solid was collected by filtration. The resultant solid was washed with hexane and dried under aeration and dried by hot air (60° C.) for 5 hours. Water (150 ml) was added to the solid, and the mixture was stirred for 2 hours, and the solid was collected by filtration, and the resultant solid was washed with water. The solid was dried by hot air (60° C.) for 3 days to give the title compound (1.117 g, 76%) as a white solid.

$^1$H-NMR Spectrum (CDCl$_3$) δ (ppm): 1.69-1.90 (4H, m), 5.19 (2H, s), 6.62 (1H, dd, J=2.4, 6.0 Hz), 6.95-7.04 (1H, m), 7.12-7.21 (1H, m), 7.28-7.45 (9H, m), 7.56 (1H, d, J=2.4 Hz), 8.19 (1H, d, J=6.0 Hz), 8.34 (1H, dd, J=7.2, 12.0 Hz). 8.49 (1H, brs), 11.27 (1H, brs).

Example 14

Benzyl 1-[({2,5-difluoro-4-[(2-{[(3-hydroxyazetidin-1-yl)carbonyl]amino}pyridin-4-yl)oxy]phenyl}amino)carbonyl]cyclopropanecarboxylate

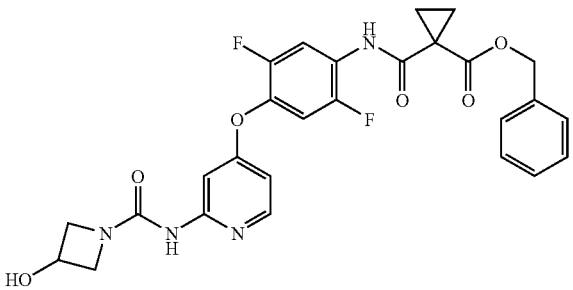

Triethylamine (0.100 ml) was added to a mixture of benzyl 1-({[4-({2-[(phenoxycarbonyl)amino]pyridin-4-yl}oxy)-2,5-difluorophenyl]amino}carbonyl)cyclopropanecarboxylate (200 mg), 3-hydroxyazetidine hydrochloride (39.1 mg) and N,N-dimethylformamide (4.0 ml) at room temperature under a nitrogen atmosphere, and the mixture was stirred for 6 hours and 10 minutes. 3-Hydroxyazetidine hydrochloride (10.0 mg) and triethylamine (0.025 ml) were added at room temperature, and the mixture was stirred for 1 hour and 20 minutes. A saturated aqueous solution of sodium hydrogencarbonate (16 ml) and hexane (5 ml) were added to the mixture, and the precipitated solid was collected by filtration. The solid was washed with water (2 ml, three times), and dried under aeration. The resultant solid was purified by silica gel column chromatography (Fuji Silysia NH, eluent; ethyl acetate, then ethyl acetate:methanol=10:1). The fractions containing the target compound was concentrated under reduced pressure to give the title compound (86.7 mg, 45%) as a white solid.

$^1$H-NMR Spectrum (CDCl$_3$) δ (ppm): 1.72-1.86 (4H, m), 3.93 (2H, dd, J=4.4, 10.0 Hz), 4.26-4.32 (2H, m), 4.66-4.73 (1H, m), 5.20 (2H, s), 6.54 (1H, dd, J=2.0, 6.0 Hz), 6.89 (1H, brs), 7.00 (1H, dd, J=7.2, 10.4 Hz), 7.30-7.43 (5H, m), 7.65 (1H, d, J=2.0 Hz), 8.04 (1H, d, J=6.0 Hz), 8.34 (1H, dd, J=7.2, 12.0 Hz), 11.27 (1H, brs).

ESI-MS (m/z): 537[M−H]$^-$.

Example 15

1-[({2,5-Difluoro-4-[(2-{[(3-hydroxyazetidin-1-yl) carbonyl]amino}pyridin-4-yl)oxy]phenyl}amino) carbonyl]cyclopropanecarboxylic acid triethylamine salt

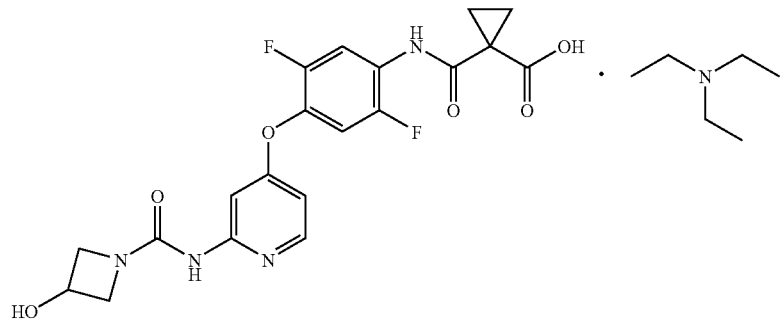

Benzyl 1-[({2,5-difluoro-4-[(2-{[(3-hydroxyazetidin-1-yl)carbonyl]amino}pyridin-4-yl)oxy]phenyl}amino)carbonyl]cyclopropanecarboxylate (84.2 mg) was dissolved in tetrahydrofuran and methanol (1:1) (2 ml) under a nitrogen atmosphere. 10% palladium on carbon (33.2 mg) was added and the air in the reaction vessel was replaced by hydrogen, and the mixture was stirred at room temperature for 20 hours. The air in the reaction vessel was replaced by nitrogen, and triethylamine (0.0435 ml) was added, and the mixture was stirred for 30 minutes. The catalyst was removed by filtration, and washed with methanol. The filtrate was concentrated under reduced pressure to give the title compound (75.3 mg, 88%) as a white solid.

ESI-MS (m/z): 447[M−H]$^-$.

Example 16

N-{2,5-Difluoro-4-[(2-{[(3-hydroxyazetidin-1-yl) carbonyl]amino}pyridin-4-yl)oxy]phenyl}-N'-(4-fluorophenyl)cyclopropane-1,1-dicarboxamide

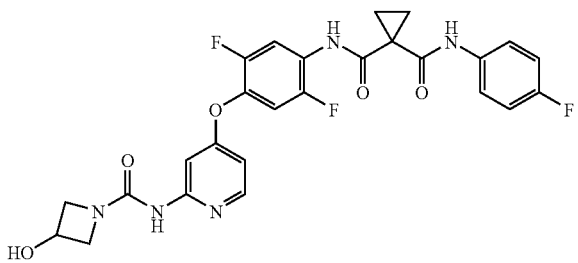

4-(4,6-Dimethoxy[1,3,5]triazin-2-yl)-4-methylmorpholinium chloride hydrate (80.8 mg) was added to a mixture of 1-[({2,5-difluoro-4-[(2-{[(3-hydroxyazetidin-1-yl)carbonyl]amino}pyridin-4-yl)oxy]phenyl}amino)carbonyl]cyclopropanecarboxylic acid triethylamine salt (75.3 mg), 4-fluoroaniline (0.026 ml) and tetrahydrofuran (1.0 ml) at room temperature under a nitrogen atmosphere, and the mixture was stirred for 5 hours. 4-(4,6-Dimethoxy[1,3,5]triazin-2-yl)-4-methylmorpholinium chloride hydrate (80.8 mg) was added at room temperature, and the mixture was stirred for 87 hours. A saturated aqueous solution of sodium hydrogencarbonate (5 ml) was added to the reaction mixture and stirred, and the mixture was partitioned after the addition of ethyl acetate (20 ml) and water (20 ml). The organic layer was washed with brine (10 ml), and dried over anhydrous magnesium sulfate. The desiccant was removed by filtration, and the filtrate was concentrated under reduced pressure. The resultant residue was purified by silica gel column chromatography (Fuji Silysia NH, eluent; ethyl acetate, ethyl acetate:methanol=10:1). The fractions containing the target compound was concentrated under reduced pressure to give the title compound (68.1 mg, 92%) as a white solid.

$^1$H-NMR Spectrum (DMSO-d$_6$) δ (ppm): 1.54-1.68 (4H, m), 3.65-3.72 (2H, m), 4.09-4.15 (2H, m), 4.33-4.41 (1H, m), 5.60 (1H, d, J=6.4 Hz), 6.62-6.66 (1H, m), 7.14-7.22 (2H, m), 7.50-7.65 (4H, m), 8.05-8.15 (1H, m), 8.13 (1H, d, J=5.6 Hz), 9.19 (1H, brs), 9.79-9.84 (1H, m), 10.95-11.02 (1H, m).

ESI-MS (m/z): 540[M−H]$^-$.

Example 17

Benzyl 1-({[(2,5-difluoro-4-{2-[3-methyl-3-(1-methylpiperidin-4-yl)ureido]pyridin-4-yl}oxy)phenyl]amino}carbonyl)cyclopropanecarboxylate

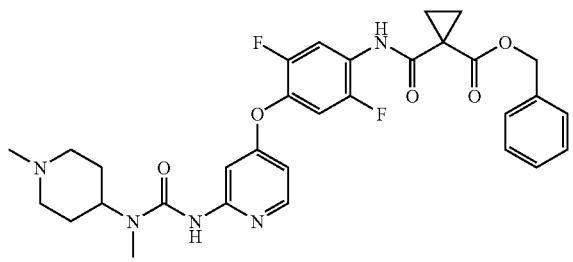

Benzyl 1-({[4-({2-[(phenoxycarbonyl)amino]pyridin-4-yl}oxy)-2,5-difluorophenyl]amino}carbonyl)cyclopropanecarboxylate (200 mg) was suspended in N-methylpyrrolidinone (2.0 ml) under a nitrogen atmosphere. 1-Methyl-4-(methylamino)piperidine (0.104 ml) was added at room temperature, and the mixture was stirred overnight. A saturated aqueous solution of sodium hydrogencarbonate (10 ml) was added to the reaction mixture, and the mixture was stirred. Extraction was performed with ethyl acetate (20 ml). The organic layer was washed with water (10 ml), a saturated aqueous solution of ammonium chloride (10 ml) and brine (10 ml), dried over anhydrous sodium sulfate. The desiccant was removed by filtration, and the filtrate was concentrated under reduced pressure. The resultant residue was purified by silica gel column chromatography (Fuji Silysia NH, eluent; ethyl acetate, then ethyl acetate:methanol=95:5). The fractions containing the target compound was concentrated under reduced pressure, and the residue was dried under reduced pressure to give the title compound (62.3 mg, 29%) as white powder.

$^1$H-NMR Spectrum (CDCl$_3$) δ (ppm): 1.60-1.90 (8H, m), 2.05-2.20 (2H, m), 2.32 (3H, s), 2.89 (3H, s), 2.90-3.00 (2H, m), 4.19 (1H, m), 5.20 (2H, s), 6.53 (1H, dd, J=2.4, 5.6 Hz), 7.00 (1H, brs), 7.20 (1H, m), 7.30-7.45 (5H, m), 7.68 (1H, d, J=2.4 Hz), 8.06 (1H, d, J=5.6 Hz), 8.33 (1H, dd, J=7.2, 12.0 Hz), 11.27 (1H, brs).

ESI-MS (m/z): 616[M+Na]$^+$.

Example 18

1-({[(2,5-Difluoro-4-{2-[3-methyl-3-(1-methylpiperidin-4-yl)ureido]pyridin-4-yl}oxy)phenyl]amino}carbonyl)cyclopropanecarboxylic acid

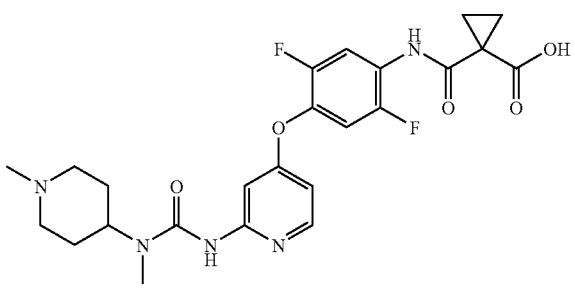

Benzyl 1-({[(2,5-difluoro-4-{2-[3-methyl-3-(1-methylpiperidin-4-yl)ureido]pyridin-4-yl}oxy)phenyl]amino}carbonyl)cyclopropanecarboxylate (61.0 mg) was dissolved in tetrahydrofuran and methanol (1:1) (4.0 ml) under a nitrogen atmosphere, and 10% palladium on carbon (45 mg) was added. The air in the reaction vessel was replaced by hydrogen, and the mixture was stirred at room temperature for 3.5 hours. The air in the reaction vessel was replaced by nitrogen, and the mixture was diluted with the addition of tetrahydrofuran and methanol (1:1) (4.0 ml). The catalyst was removed by filtration, and washed with methanol. The filtrate was distilled off under reduced pressure to give the title compound (49.2 mg, 95%) as a white solid.

ESI-MS (m/z): 502[M−H]$^-$.

Example 19

N-(2,5-Difluoro-4-({[2-({[methyl(1-methylpiperidin-4-yl)amino]carbonyl}amino)pyridin-4-yl]oxy}phenyl)-N'-(4-fluorophenyl)cyclopropane-1,1-dicarboxamide

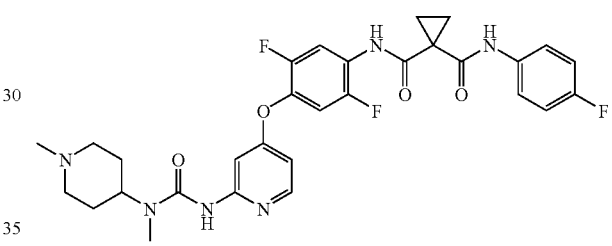

4-(4,6-Dimethoxy[1,3,5]triazin-2-yl)-4-methylmorpholinium chloride hydrate (57.6 mg) was added to a mixture of 1-({[(2,5-difluoro-4-{2-[3-methyl-3-(1-methylpiperidin-4-yl)ureido]pyridin-4-yl}oxy)phenyl]amino}carbonyl)cyclopropanecarboxylic acid (49.2 mg), 4-fluoroaniline (0.0186 ml) and tetrahydrofuran (2 ml) at room temperature under a nitrogen atmosphere, and the mixture was stirred for 15 hours. A saturated aqueous solution of sodium hydrogencarbonate (5 ml) was added to the reaction mixture, and the mixture was stirred. The mixture was partitioned after the addition of ethyl acetate (20 ml) and water (15 ml). The organic layer was washed with brine (10 ml), and dried over anhydrous sodium sulfate. The desiccant was removed by filtration, and the filtrate was concentrated under reduced pressure. The resultant residue was purified by silica gel column chromatography (Fuji Silysia NH, eluent; ethyl acetate, then ethyl acetate:methanol=95:5). The fractions containing the target compound was concentrated under reduced pressure to give the title compound (41.5 mg, 71%) as a white solid.

$^1$H-NMR Spectrum (CDCl$_3$) δ (ppm): 1.61-1.83 (8H, m), 2.03-2.10 (2H, m), 2.28 (3H, s), 2.88 (3H, s), 2.90-2.94 (2H, m), 4.10-4.20 (1H, m), 6.55 (1H, dd, J=2.4, 5.6 Hz), 6.98-7.08 (3H, m), 7.15 (1H, s), 7.46-7.50 (2H, m), 7.67 (1H, d, J=2.4 Hz), 8.08 (1H, d, J=5.6 Hz), 8.29 (1H, dd, J=7.2, 12.0 Hz), 8.57 (1H, s), 9.59 (1H, s).

ESI-MS (m/z): 597[M+H]$^+$.

Example 20

Benzyl 1-[({2,5-difluoro-4-[(2-{[((S)-3-hydroxypyrrolidin-1-yl)carbonyl]amino}pyridin-4-yl)oxy]phenyl}amino)carbonyl]cyclopropanecarboxylate

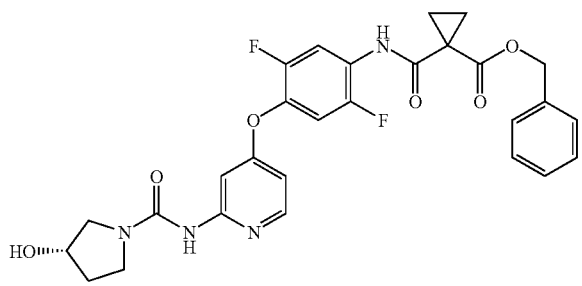

(S)-3-Hydroxypyrrolidine (0.0577 ml) was added to a mixture of benzyl 1-({[4-({2-[(phenoxycarbonyl)amino]pyridin-4-yl}oxy)-2,5-difluorophenyl]amino}carbonyl)cyclopropanecarboxylate (200 mg) and N-methylpyrrolidinone (4.0 ml) at room temperature under a nitrogen atmosphere, and the mixture was stirred for 2 hours. A saturated aqueous solution of sodium hydrogencarbonate (20 ml) was added to the mixture, and the mixture was stirred for 30 minutes. The precipitated solid was collected by filtration, and the solid was washed with water (20 ml, three times), and the solid was dried by hot air (80° C.) for 1 day to give the title compound (159.0 mg, 81%) as a white solid.

$^1$H-NMR Spectrum (CDCl$_3$) δ (ppm): 1.71-1.88 (4H, m), 2.00-2.17 (2H, m), 3.47-3.69 (4H, m), 4.53-4.59 (1H, m), 5.20 (2H, m), 6.54 (1H, dd, J=2.0, 5.6 Hz), 7.00 (1H, dd, J=7.2, 10.4 Hz), 7.08 (1H, brs), 7.30-7.44 (5H, m), 7.70 (1H, d, J=2.0 Hz), 8.05 (1H, d, J=5.6 Hz), 8.31-8.38 (1H, m), 11.27 (1H, brs).

ESI-MS (m/z): 551[M–H]$^-$.

Example 21

1-[({2,5-Difluoro-4-[(2-{[((S)-3-hydroxypyrrolidin-1-yl)carbonyl]amino}pyridin-4-yl)oxy]phenyl}amino)carbonyl]cyclopropanecarboxylic acid triethylamine salt

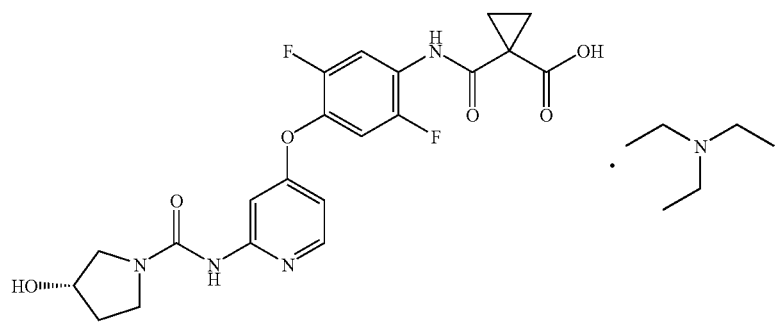

Benzyl 1-[({2,5-difluoro-4-[(2-{[((S)-3-hydroxypyrrolidin-1-yl)carbonyl]amino}pyridin-4-yl)oxy]phenyl}amino)carbonyl]cyclopropanecarboxylate (156.8 mg) was dissolved in tetrahydrofuran and methanol (1:1) (4 ml) under a nitrogen atmosphere. 10% palladium on carbon (60.4 mg) was added, and the air in the reaction vessel was replaced by hydrogen, and the mixture was stirred at room temperature for 19 hours. The air in the reaction vessel was replaced by nitrogen, and triethylamine (0.0991 ml) was added, and the mixture was stirred for 30 minutes. The catalyst was removed by filtration, and washed with methanol. The filtrate was concentrated under reduced pressure to give the title compound (174.9 mg, quant.) as a white solid.

ESI-MS (m/z): 461[M–H]$^-$.

Example 22

N-{2,5-Difluoro-4-[(2-{[((S)-3-hydroxypyrrolidin-1-yl)carbonyl]amino}pyridin-4-yl)oxy]phenyl}-N'-(4-fluorophenyl)cyclopropane-1,1-dicarboxamide

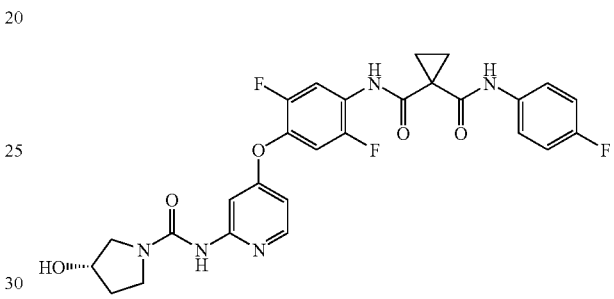

4-(4,6-Dimethoxy[1,3,5]triazin-2-yl)-4-methylmorpholinium chloride hydrate (365 mg) was added to a mixture of 1-[({2,5-difluoro-4-[(2-{[((S)-3-hydroxypyrrolidin-1-yl)carbonyl]amino}pyridin-4-yl)oxy]phenyl}amino)carbonyl]cyclopropanecarboxylic acid triethylamine salt (175 mg), 4-fluoroaniline (0.0587 ml) and tetrahydrofuran (4.0 ml) at room temperature under a nitrogen atmosphere, and the mixture was stirred for 68 hours and 30 minutes. A saturated aqueous solution of sodium hydrogencarbonate (10 ml) was added to the mixture and stirred, and the mixture was partitioned after the addition of ethyl acetate and tetrahydrofuran (1:1) (40 ml) and water (30 ml). The organic layer was washed with brine (20 ml), and dried over anhydrous magnesium sulfate. The desiccant was removed by filtration, and the filtrate was concentrated under reduced pressure. The resultant residue was purified by silica gel column chromatography (Fuji Silysia NH, eluent; ethyl acetate, then ethyl acetate:methanol=10:1). The fractions containing the target compound were concentrated under reduced pressure to give the title compound (128.5 mg, 75%) as a white solid.

$^1$H-NMR Spectrum (CDCl$_3$) δ (ppm): 1.67-1.77 (4H, m), 2.00-2.16 (2H, m), 3.46-3.67 (4H, m), 4.52-4.58 (1H, m), 6.55-6.59 (1H, m), 6.97-7.10 (4H, m), 7.45-7.52 (2H, m), 7.67 (1H, d, J=2.0 Hz), 8.07 (1H, d, J=5.6 Hz), 8.28 (1H, dd, J=7.6, 12.0 Hz), 8.64-8.70 (1H, m), 9.49-9.55 (1H, m).

ESI-MS (m/z): 554[M−H]$^-$.

Example 23

Benzyl 1-[({2,5-difluoro-4-[(2-{[((R)-3-hydroxypyrrolidin-1-yl)carbonyl]amino}pyridin-4-yl)oxy]phenyl}amino)carbonyl]cyclopropanecarboxylate

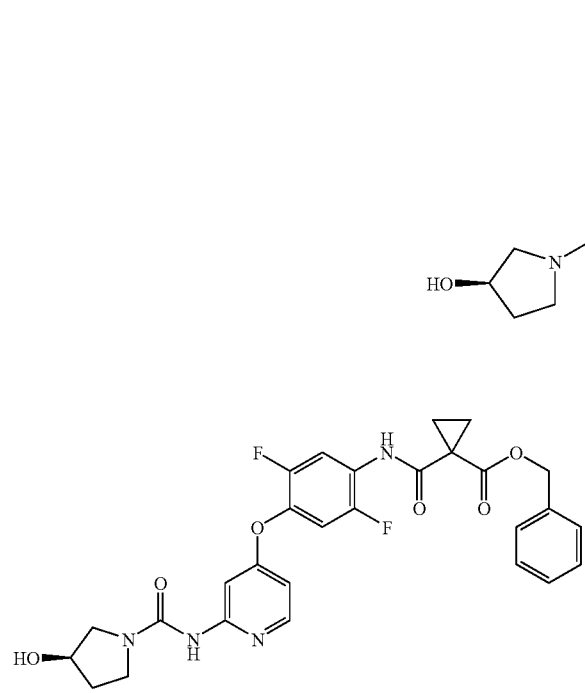

N,N-Diisopropylethylamine (0.249 ml) was added to a mixture of benzyl 1-({[4-({2-[(phenoxycarbonyl)amino]pyridin-4-yl}oxy)-2,5-difluorophenyl]amino}carbonyl)cyclopropanecarboxylate (200 mg), (R)-3-hydroxypyrrolidine hydrochloride (88.2 mg) and N-methylpyrrolidinone (4.0 ml) at room temperature under a nitrogen atmosphere, and the mixture was stirred for 5 hours. (R)-3-Hydroxypyrrolidine hydrochloride (44.1 mg) and N,N-diisopropylethylamine (0.125 ml) were added at room temperature, and the mixture was stirred for 15 hours and 40 minutes. A saturated aqueous solution of sodium hydrogencarbonate (20 ml) was added to the mixture to quench the reaction, and the mixture was partitioned after the addition of ethyl acetate and tetrahydrofuran (1:1) (50 ml) and (30 ml). The organic layer was washed with brine (30 ml), and dried over anhydrous magnesium sulfate. The desiccant was removed by filtration, and the filtrate was concentrated under reduced pressure. The resultant residue was purified by silica gel column chromatography (Fuji Silysia NH, eluent; ethyl acetate, then ethyl acetate:methanol=10:1). The fractions containing the target compound were concentrated under reduced pressure to give the title compound (178.2 mg, 90%) as a white solid.

$^1$H-NMR Spectrum (CDCl$_3$) δ (ppm): 1.71-1.88 (4H, m), 2.00-2.17 (2H, m), 3.47-3.69 (4H, m), 4.53-4.59 (1H, m), 5.20 (2H, m), 6.54 (1H, dd, J=2.0, 5.6 Hz), 7.00 (1H, dd, J=7.2, 10.4 Hz), 7.08 (1H, brs), 7.30-7.44 (5H, m), 7.70 (1H, d, J=2.0 Hz), 8.05 (1H, d, J=5.6 Hz), 8.31-8.38 (1H, m), 11.27 (1H, brs).

ESI-MS (m/z): 551[M−H]$^-$.

Example 24

1-[({2,5-Difluoro-4-[(2-{[((R)-3-hydroxypyrrolidin-1-yl)carbonyl]amino}pyridin-4-yl)oxy]phenyl}amino)carbonyl]cyclopropanecarboxylic acid triethylamine salt

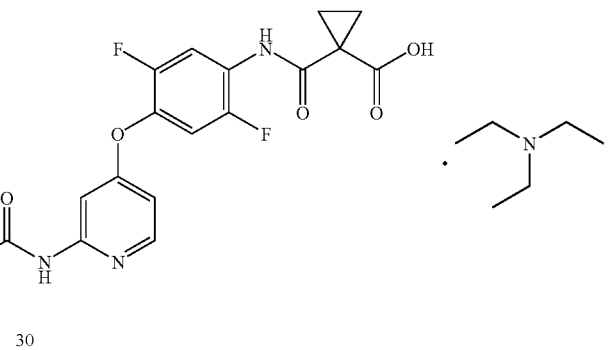

Benzyl 1-[({2,5-difluoro-4-[(2-{[((R)-3-hydroxypyrrolidin-1-yl)carbonyl]amino}pyridin-4-yl)oxy]phenyl}amino)carbonyl]cyclopropanecarboxylate (156.8 mg) was dissolved in tetrahydrofuran and methanol (2:1) (6 ml) under a nitrogen atmosphere. 10% palladium on carbon (68.6 mg) was added, and the air in the reaction vessel was replaced by hydrogen, and the mixture was stirred at room temperature for 16 hours and 30 minutes. The air in the reaction vessel was replaced by nitrogen, and triethylamine (0.112 ml) was added, and the mixture was stirred for 30 minutes. The catalyst was removed by filtration, and washed with methanol. The filtrate was concentrated under reduced pressure to give the title compound (185.3 mg, quant.) as a white solid.

ESI-MS (m/z): 461[M−H]$^-$.

Example 25) N-{2,5-Difluoro-4-[(2-{[((R)-3-hydroxypyrrolidin-1-yl)carbonyl]amino}pyridin-4-yl)oxy]phenyl}-N'-(4-fluorophenyl)cyclopropane-1,1-dicarboxamide

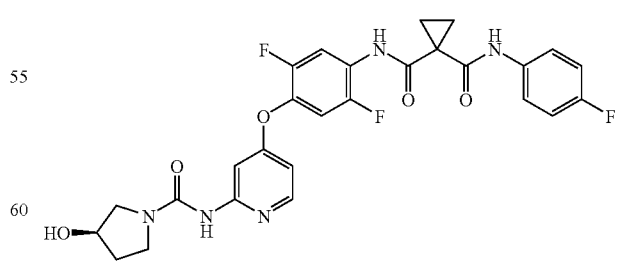

4-(4,6-Dimethoxy[1,3,5]triazin-2-yl)-4-methylmorpholinium chloride hydrate (388 mg) was added to a mixture of 1-[({2,5-difluoro-4-[(2-{[((R)-3-hydroxypyrrolidin-1-yl)carbonyl]amino}pyridin-4-yl)oxy]phenyl}amino)carbonyl]

cyclopropanecarboxylic acid triethylamine salt (185.3 mg), 4-fluoroaniline (0.0623 ml) and tetrahydrofuran (4.0 ml) at room temperature under a nitrogen atmosphere, and the mixture was stirred for 68 hours. A saturated aqueous solution of sodium hydrogencarbonate (10 ml) was added to the reaction mixture and stirred, and the mixture was partitioned after the addition of ethyl acetate and tetrahydrofuran (1:1) (40 ml) and water (30 ml). The organic layer was washed with brine (20 ml), and dried over anhydrous magnesium sulfate. The desiccant was removed by filtration, and the filtrate was concentrated under reduced pressure. The resultant residue was purified by silica gel column chromatography (Fuji Silysia NH, eluent; ethyl acetate, then ethyl acetate:methanol=10:1). The fractions containing the target compound were concentrated under reduced pressure to give the title compound (132.8 mg, 73%) as a white solid.

$^1$H-NMR Spectrum (CDCl$_3$) δ (ppm): 1.67-1.77 (4H, m), 2.00-2.16 (2H, m), 3.46-3.67 (4H, m), 4.52-4.58 (1H, m), 6.55-6.59 (1H, m), 6.97-7.10 (4H, m), 7.45-7.52 (2H, m), 7.67 (1H, d, J=2.0 Hz), 8.07 (1H, d, J=5.6 Hz), 8.28 (1H, dd, J=7.6, 12.0 Hz), 8.64-8.70 (1H, m), 9.49-9.55 (1H, m).

ESI-MS (m/z): 554[M−H]$^-$.

The preparing process according to the present invention can be carried out by performing a reaction similar to the above Examples using as a starting material the amine described in the above Production Example or a publicly known amine.

Pharmacological Test Examples

The biological activity and pharmaceutical effect (inhibitory activity for hepatocyte growth factor receptor, anti-tumor activity, inhibitory activity for angiogenesis, and inhibitory activity for cancer metastasis) of the compound according to the present invention were evaluated by methods described below.

Abbreviations and terms used in the following Pharmacological Test Examples are listed as follows:

(Abbreviation List)
HGFR (Hepatocyte growth factor receptor)
DNA (Deoxyribonucleic acid)
Human placenta (Human placenta)
PCR (Polymerase chain reaction)
VEGFR2 (Vascular endothelial growth factor receptor 2)
FGFR1 (Fibroblast growth factor receptor 1)
PDGFRβ (Platelet derived growth factor receptor β)
EGFR (Epidermal growth factor receptor)
FBS (Fetal bovine serum)
PBS (Phosphate buffered saline)
Tris (Tris(hydroxymethyl)aminomethane, Tris(buffer))
PMSF (Phenylmethylsulfonyl fluoride)
NP-40 (Nonidet P-40)
EGTA (O,O-Bis(2-aminoethyleneglycol)-N,N,N',N'-tetraacetic acid)
SDS (Sodium dodecyl sulfate)
BSA (Bovine serum albumin)
Hepes (N-[2-hydroxyethyl]piperazine-N'-[2-ethanesulfonic acid], Hepes(buffer))
ATP (Adenosine 5'-triphosphate)
EDTA (Ethylenediamine tetraacetic acid)
HTRF (Homogenous Time-Resolved Fluorescence)
HRP (Horseradish peroxidase)
ELISA (Enzyme-linked immunosorbent assay)

Pharmacological Test Example 1

Inhibitory Activity Against Receptor Tyrosine Kinase Activity

1. Cloning of Receptor Tyrosine Kinases, and Preparation of the Recombinant Baculovirus Solutions The cytoplasmic domain of HGFR (GenBank Accession No. J02958) is a 1.3 kb DNA fragment beginning with Lys974 and including a stop codon, and described by Park et al. (Proc. Natl. Acad. Sci. U.S.A. 84(18), 6379-6383, 1987). The DNA fragment was isolated from the human placental cDNA library (purchased from Clontech) by PCR (TaKaRa Ex Taq™ Kit, purchased from TaKaRa) using two kinds of primers (SEQ ID NO: 1,5'-CCGGCCGGATCCAAAAA-GAGAAAGCAAATTAAA-3' and SEQ ID NO: 2,5'-TTAAT-TCTGCAGCTATGATGTCTCCCAGAAGGA-3', purchased from Invitrogen). The DNA fragment was cloned into a baculovirus transplace vector (pFastBac™-HT (purchased from GIBCO BRL)) to produce a recombinant construct. The construct was transfected into insect cells (*Spodoptera frugiperda* 9(Sf9)) to produce a solution of HGFR transfected baculovirus (preparation of a recombinant baculovirus can be found in the standard text (Bac-to-Bac Baculovirus Expression System (GIBCO BRL)). The cloning of the other receptor tyrosine kinases and preparation of the recombinant baculovirus solutions were prepared using a cytoplasmic fragment starting from Lys791 (VEGFR2, GenBank Accession No. L04947), a cytoplasmic fragment starting from Lys398 (FGFR1, GenBank Accession No. X52833) and a cytoplasmic fragment starting from Lys558 (PDGFRβ, GenBank Accession No. M21616) in stead of HGFR in the above method. EGFR was purchased from Sigma (Production No. E-2645).

2. Expression and Purification of Receptor Tyrosine Kinases

To the suspension of Sf9 cells (3×10$^8$ cells) in SF-900II medium (purchased from Invitrogen) containing 2% FBS was added a solution of HGFR transfected baculovirus above (4 ml), followed by a shaking culture at 27° C. for 48 hrs. The cells infected with the HGFR transfected baculovirus were centrifuged at 1,000 rpm, 4° C. for 5 min to remove the supernatant. The precipitated infected cells were suspended in 80 ml of ice-cold PBS, and centrifuged at 1,000 rpm, 4° C. for 5 min to remove the supernatant. The precipitated infected cells were suspended in 40 ml of ice-cold Lysis Buffer (50 mM Tris-HCl (pH 8.5), 5 mM 2-mercaptoethanol, 100 mM KCl, 1 mM PMSF and 1% (v/v) NP-40). The suspension was centrifuged at 12,000 rpm, 4° C. for 30 min to provide a supernatant.

The supernatant was loaded onto an Ni-NTA agarose column (3 ml, purchased from Qiagen) equilibrated with 30 ml of Buffer A (20 mM Tris-HCl (pH 8.5), 5 mM 2-mercaptoethanol, 500 mM KCl, 20 mM imidazole and 10% (v/v) glycerol). The column was washed with 30 ml of Buffer A, 6 ml of Buffer B (20 mM Tris-HCl (pH 8.5), 5 mM 2-mercaptoethanol, 1 M KCl, and 10% (v/v) glycerol) and 6 ml of Buffer A in this order. Then, the column was eluted with 6 ml of Buffer C (20 mM Tris-HCl (pH 8.5), 5 mM 2-mercaptoethanol, 100 mM KCl, 100 mM imidazole, and 10% (v/v) glycerol) to provide a fraction. The fraction was entrapped in a dialysis membrane (purchased from Spectrum Laboratories), dialyzed at 4° C. overnight with 1 L of dialysis buffer (20 mM Tris-HCl (pH 7.5), 10% (v/v) glycerol, 1 mM dithiothreitol, 0.1 mM Na$_3$VO$_4$ and 0.1 mM EGTA), and stored at −80° C. until used. An aliquot of the dialyzed fraction was subjected to SDS electrophoresis, and then a recombinant protein (His6-HGFR, the HGFR cytoplasmic domain fused with six histidine at the N terminus) detected at a molecular weight of about 60 kDa when stained with Coomassie Brilliant Blue, was determined with regard to protein content using BSA (purchased from Sigma) as a standard. The VEGFR2 cytoplasmic domain, the FGFR1 cytoplasmic domain, and the PDGFRβ cytoplasmic domain were fused with six histidine at the N terminus by the similar method to produce respective recombinant proteins (His6-VEGFR2, His6-FGFR1, and His6-PDGFRβ).

3. Assay for the Inhibitory Activity Against HGFR Tyrosine Kinase Activity

To each well of a 96-well round plate (purchased from NUNC, Production No. 163320) were added 10 μl of a solution for kinase reaction (200 mM Hepes (pH 7.4), 80 mM $MgCl_2$, 16 mM $MnCl_2$ and 2 mM $Na_3VO_4$), 250 ng of biotinylated poly(Glu4: Tyr1) (biotin-poly(GT), purchased from Japan Schering) (6 μl, 15-fold diluted with distilled water), 30 ng of His6-HGFR (10 μl, 60-fold diluted with 0.4% BSA) and a test substance dissolved in dimethyl sulfoxide (4 μl, 100-fold diluted with 0.1% BSA) to mess up to 30 μl. To the well was added 10 μl of 4 μM ATP (purchased from Sigma) diluted with distilled water to incubate at 30° C. for 10 min. followed by adding 10 μl of 500 mM EDTA (pH 8.0) (purchased from Wako Pure Chemicals) to provide a kinase reaction solution.

The tyrosine-phosphorylated biotin-poly(GT) was detected using the Homogenous Time-Resolved Fluorescence (HTRF) method (Analytical Biochemistry, 269, 94-104, 1999). That is, to each well of a 96-well half-area black plate (purchased from COSTAR, Production No. 3694) were added 20 μl of the above kinase reaction solution and 30 μl of a dilution solution (50 mM Hepes (pH 7.4), 20 mM $MgCl_2$, 4 mM $MnCl_2$, 0.5 mM $Na_3VO_4$, 0.1% BSA and 100 mM EDTA). To the well was added 7.5 ng of an europium cryptate-labelled anti-phosphotyrosine antibody (Eu(K)-PY20, purchased from Japan Schering) (25 μl, 250-fold diluted with 20 mM Hepes (pH 7.0), 0.5 M KF and 0.1% BSA) and 250 ng of XL665-labelled streptavidin (XL665-SA, purchased from Japan Schering) (25 μl, 62.5-fold diluted with 20 mM Hepes (pH 7.0), 0.5 M KF and 0.1% BSA), and using a discovery HTRF microplate analyzer (Packard), the well was instantly irradiated at an excitation wavelength of 337 nm to determine fluorescence intensities at 665 nm and 620 nm. The tyrosine phosphorylation rate of a biotin-poly (GT) was calculated using a delta F % value described in the text of a HTRF standard experiment method by Japan Schering. While defining the delta F % value of a well added with His6-HGFR and no test substance as 100% and the delta F % value of a well added with no His6-HGFR and no test substance as 0%, ratio (%) of the delta F % value of each well added with the test substance was calculated. The ratio (%) was used to calculate the concentration ($IC_{50}$) of the test substance necessary to inhibit HGFR kinase activity by 50%, and the results are shown in Table 1.

TABLE 1

| Example | IC50 (μM) |
|---------|-----------|
| 9 | 0.053 |
| 16 | 0.004 |
| 19 | 0.049 |
| 22 | 0.016 |
| 25 | 0.010 |

4. Assay for the Inhibitory Activity Against Receptor Tyrosine Kinase Activities Other than HGFR The inhibitory activity against tyrosine kinase activities of VEGFR2, FGFR1, and EGFR were determined by the similar manner as in the assay for the inhibitory activity against HGFR tyrosine kinase activity described above, using 15 ng of His6-VEGFR2, 15 ng of His6-FGFR1 or 23 ng of EGFR, respectively instead of HGFR.

The inhibitory activity against PDGFRβ tyrosine kinase activity was evaluated by obtaining a kinase reaction solution by the above method using 50 ng of His6-PDGFRβ, followed by detecting the tyrosine phosphorylated biotin-poly(GT) by a method described below.

To each well of a 96-well streptavidin-coated plate (purchased from PIERCE, Production No. 15129) were added 34 μl of the kinase reaction solution and 16 μl of a dilution solution, followed by incubation at room temperature for 30 min. Then, the well was washed three times with 150 μl of a washing solution (20 mM Tris-HCl (pH 7.6), 137 mM NaCl, 0.05% Tween-20 and 0.1% BSA), and to the well was added 70 μl of anti-phosphotyrosine (PY20)-HRP conjugate (purchased from Transduction Laboratories, Production No. P-11625) (2,000-fold diluted with 20 mM Tris-HCl (pH 7.6), 137 mM NaCl, 0.05% Tween-20 and 1% BSA), followed by incubation at room temperature for 1 hr. Then, each well was washed three times with 150 μl of the washing solution, and supplied with 100 μl of TMB Membrane Peroxidase Substrate (purchased from Funakoshi, Production No. 50-5077-03). After incubating the same at room temperature for 10 min, 100 μl of 1 M phosphoric acid was added to each well, and using a Plate Reader MTP-500 (Corona Electric), the absorbance of the well was instantly determined at 450 nm. While defining the absorbance of a well supplied with His6-PDGFRβ and no test substance as 100% and the absorbance of a well supplied with no His6-PDGFRβ and no test substance as 0%, the absorbance ratio (%) of each well supplied with the test substance was calculated. The absorbance ratio (%) was used to calculate the concentration ($IC_{50}$) of the test substance necessary to inhibit PDGFRβ kinase activity by 50%.

Pharmacological Test Example 2

Inhibitory Activity Against the Proliferation of Human Gastric Cancer Cells (MKN-45)

Human gastric cancer cells (MKN-45) were suspended in a 1% FBS-containing RPMI1640 medium (purchased from Sigma). The cell suspension ($1 \times 10^4$ cells/ml) was added in a 96-well plate for cell culture (purchased from NUNC, Production No. 167008) at 0.1 ml/well, and then cultured in a 5% $CO_2$ incubator (37° C.) overnight. After the culture, each well was supplied with 0.1 ml of a test substance diluted with a 1% FBS-containing RPMI1640 medium, followed by culturing in a 5% $CO_2$ incubator (37° C.) for 3 days. After the culture, each well was supplied with 10 μl of Cell Counting Kit-8 (purchased from DOJINDO, Production No. 343-07623), followed by incubation in a 5% $CO_2$ incubator (37° C.) for about 1.5 hrs. After the incubation, using the Plate Reader MTP-500 (Corona Electric), the absorbance of each well was determined at a measurement wavelength of 450 nm and a reference wavelength of 660 nm. The ratio (%) of absorbance of each well supplied with a test substance to absorbance of the well supplied with no test substance was calculated, and the ratio was used to calculate the concentration ($IC_{50}$) of the test substance necessary to inhibit the cell proliferation by 50%, and the results are shown in Table 2.

TABLE 2

| Example | IC50 (μM) |
|---|---|
| 9 | 0.017 |
| 16 | 0.005 |
| 19 | 0.0049 |
| 22 | 0.0024 |
| 25 | 0.0022 |

Pharmacological Test Example 3

Inhibitory Activity Against the HGFR Autophosphorylation Using ELISA

1. Preparation of Cell Extract

Human gastric cancer cells (MKN-45) were suspended in a 1% FBS-containing RPMI1640 medium (purchased from Sigma). The cell suspension ($1 \times 10^5$ cells/ml) was put in a 96-well plate for cell culture (purchased from NUNC, Production No. 1670.08) at 0.1 ml/well, and then cultured in a 5% $CO_2$ incubator (37° C.) overnight. After the culture, from each well was removed the supernatant, followed by adding 0.05 ml of a 1% FBS-containing RPMI1640 medium. Then, the well was supplied with 0.05 ml of the test substance dissolved in dimethyl sulfoxide (diluted with a 1% FBS-containing RPMI1640 medium), followed by culturing in a 5% $CO_2$ incubator (37° C.) for 1 hr. From each well was removed the supernatant, and each well was washed with 150 μl of PBS, followed by adding 100 μl of a lysis buffer (50 mM Hepes (pH 7.4), 150 mM NaCl, 10% (v/v) glycerol, 1% Triton X-100, 1.5 mM $MgCl_2$, 1 mM EDTA (pH 8.0), 100 mM NaF, 1 mM PMSF, 10 μg/ml Aprotinin, 50 μg/ml Leupeptin, 1 μg/ml Pepstatin A and 1 mM $Na_3VO_4$). The plate was shaken at 4° C. for 1 hr to prepare the cell extract.

2. Preparation of an Anti-Phosphotyrosine Antibody-Immobilized Plate

To a 96-well plate for ELISA (purchased from COSTAR, Production No. 3369) was added 50 μl of 60 mM bicarbonate buffer (pH 9.6) containing 50 μg/ml of an anti-phosphotyrosine antibody (PY20, purchased from Transduction Laboratory, Production No. P-11120). The plate was incubated at 4° C. overnight.

3. Assay for Inhibitory Activity Against HGFR Autophosphorylation

Each well of the plate prepared in 2. was washed three times with 200 μl of PBS, and supplied with 150 μl of 3% BSA/PBS, followed by incubating at room temperature for 2 hrs. Each well was washed three times with 200 μl of PBS, and supplied with 50 μl of the above cell extract, followed by incubating at 4° C. overnight. After the incubation, each well was washed three times with 250 μl of a washing solution (0.1% BSA, 20 mM Tris-HCl (pH 7.6), 137 mM NaCl, and 0.05% Tween-20), and supplied with 70 μl of anti-HGFR antibody (h-Met(C-12), purchased from Santa Cruz, Production No. sc-10) 2,000-fold diluted with a reaction solution (1% BSA, 20 mM Tris-HCl (pH 7.6), 137 mM NaCl and 0.05% Tween-20), followed by incubating at room temperature for 1 hr. The well was washed three times with 250 μl of the washing solution, and supplied with 70 μl of peroxidase-labelled anti-rabbit IgG antibody (purchased from Cell Signaling, Production No. 7074) 2,000-fold diluted with the reaction solution, followed by incubating at room temperature for 1 hr. Each well was washed three times with 250 μl of the washing solution, and supplied with 70 μl of TMB Membrane Peroxidase Substrate (purchased from Funakoshi, Production No. 50-5077-03), followed by incubating at room temperature for 10 min. Each well was supplied with 70 μl of 1 M phosphoric acid, and using the Plate Reader MTP-500 (Corona Electric), the absorbance of the well was instantly determined at a measurement wavelength of 450 nm. While defining the absorbance of a well supplied with the cell extract having no test substance as 100% HGFR autophosphorylation activity, and the absorbance of a well supplied with 50 μl of the lysis buffer as 0% HGFR autophosphorylation activity, the HGFR autophosphorylation activity (%) was calculated for each well. The concentration of the test substance was changed by several levels to calculate HGFR autophosphorylation activities (%) in respective cases, and to calculate the concentration ($IC_{50}$) of the test substance necessary to inhibit HGFR autophosphorylation activity by 50%, and the results are shown in Table 3.

TABLE 3

| Example | IC50 (μM) |
|---|---|
| 9 | 0.016 |
| 16 | 0.0084 |
| 19 | 0.011 |
| 22 | 0.0045 |
| 25 | 0.0034 |

Measurement of Powder X-Ray Diffraction

With regard to the crystals obtained in Example 9 (Method 3), about 5 mg of sample was ground in a mortar and then sampled on an aluminum pan for measurement. Measurement was carried out under the conditions below.

Apparatus: X-ray DSC system TTR-III (manufactured by Rigaku Denki KK)
X-ray: CuKα
Goniometer: TTR-III horizontal goniometer
Counter: scintillation counter
Tube voltage: 50 kV
Tube current: 300 mA
Scan speed: 5°/min
Scan axis: 2θ/θ
Scan range: 2θ=5° to 35°
Divergent slit: 0.5 mm
Divergent vertical limited slit: 2 mm
Scattering slit: open
Receiving slit: open
Sampling width: 0.02°
Accumulation: 1

The powder X-ray diffraction pattern of the crystals obtained in Example 9 (Method 3) is shown in FIG. 1, and the representative peaks and their relative intensities of diffraction angles (2θ) of the crystals are shown in table 4.

TABLE 4

| 2θ | Relative Intensity |
|---|---|
| 6.3 | 100 |
| 12.3 | 52 |
| 17.3 | 58 |
| 18.3 | 31 |
| 18.4 | 19 |
| 19.2 | 19 |
| 19.8 | 29 |
| 20.0 | 15 |
| 20.1 | 18 |
| 20.2 | 21 |
| 22.1 | 19 |
| 23.7 | 18 |

INDUSTRIAL APPLICABILITY

The processes for preparing phenoxypyridine derivatives according to the present invention can provide phenoxypyridine derivatives useful as anti-tumor agents, angiogenesis inhibitors or inhibitors for cancer metastasis against various kinds of tumors such as a pancreatic cancer, a gastric cancer, a colorectal cancer, a breast cancer, a prostate cancer, a lung cancer, a renal cancer, a brain tumor or an ovarian cancer.

with a compound represented by the formula (III):

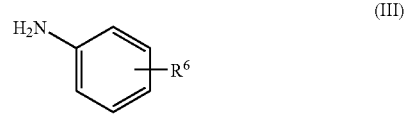

(III)

---

---

What is claimed is:

1. A process for preparing a compound represented by the formula (I):

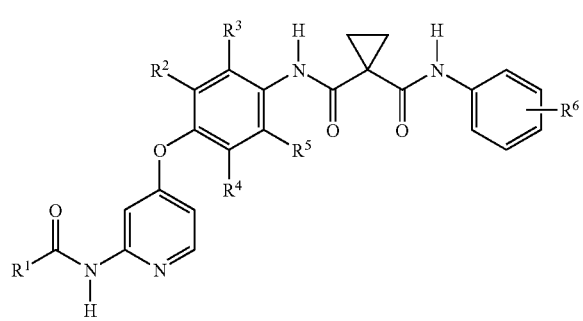

(I)

comprising reacting a compound represented by the formula (II) or salt thereof:

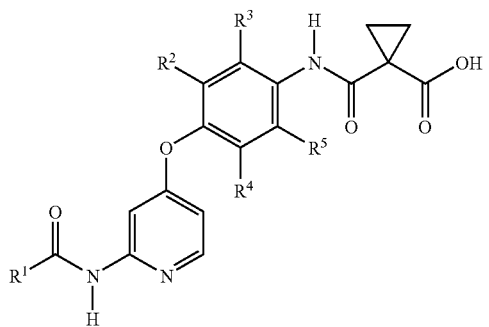

(II)

in the presence of a condensation reagent, wherein $R^1$ represents 1) azetidin-1-yl optionally substituted with a substituent selected from Substituent Group A, 2) pyrrolidin-1-yl optionally substituted with a substituent selected from Substituent Group A, 3) piperidin-1-yl optionally substituted with a substituent selected from Substituent Group A, 4) piperazin-1-yl optionally substituted with a substituent selected from Substituent Group A, 5) diazepan-1-yl optionally substituted with a substituent selected from Substituent Group A, 6) morpholin-4-yl optionally substituted with a substituent selected from Substituent Group A, or 7) —$NR^{11a}R^{11b}$, wherein $R^{11a}$ represents hydrogen or methyl, and $R^{11b}$ represents n-propyl, n-butyl, pyrrolidin-3-yl, piperidin-3-yl, piperidin-4-yl or tetrahydropyran-4-yl, and $R^{11b}$ may be substituted with a substituent selected from Substituent Group B;

$R^2$, $R^3$, $R^4$ and $R^5$ may be the same or different and each represents hydrogen or fluorine;

Substituent Group A consists of hydroxyl, dimethylaminoacetoxy, methyl, ethyl, dimethylamino, azetidinyl, pyrrolidinyl, piperidinyl and piperazinyl, where each group included in Substituent Group A other than hydroxyl and dimethylaminoacetoxy may be substituted with hydroxyl, methyl, dimethylamino, azetidinyl, pyrrolidinyl or piperidinyl;

Substituent Group B consists of methyl, ethyl, n-propyl, acetyl, dimethylamino, diethylamino, azetidinyl, pyrrolidinyl and piperazinyl, where each group included in Substituent Group B may be substituted with methyl or dimethylamino; and $R^6$ represents hydrogen or fluorine.

2. The process according to claim 1, wherein the compound represented by the formula (II) or salt thereof:

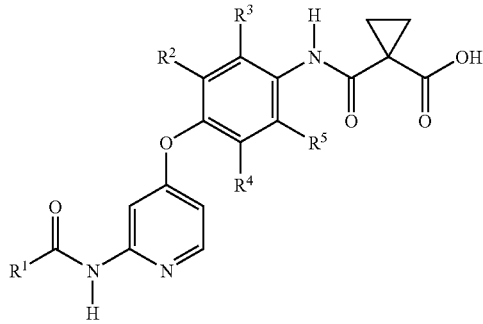

wherein $R^1$, $R^2$, $R^3$, $R^4$ and $R^5$ have the same definitions as defined in claim 1, is prepared by hydrolysis or catalytic hydrogenation of a compound represented by the formula (IV) or salt thereof:

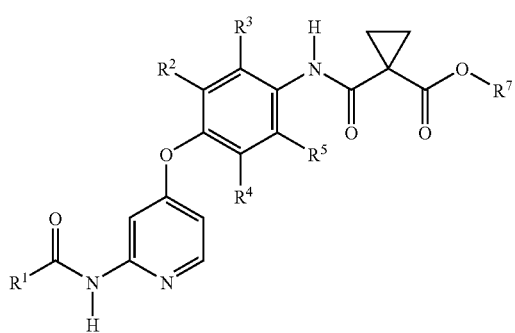

wherein $R^1$, $R^2$, $R^3$, $R^4$ and $R^5$ have the same definitions as defined in claim 1, and $R^7$ represents $C_{1-6}$ alkyl or benzyl optionally substituted with one or two substituents selected from (1) halogen, (2) hydroxyl, (3) nitro, (4) cyano, (5) trifluoromethyl, (6) $C_{1-6}$ alkyl, (7) $C_{1-6}$ alkoxy, (8) amino, (9) mono-$C_{1-6}$ alkylamino and (10) di-$C_{1-6}$ alkylamino on the benzene ring.

3. The process according to claim 2, wherein the compound represented by the formula (IV) or salt thereof:

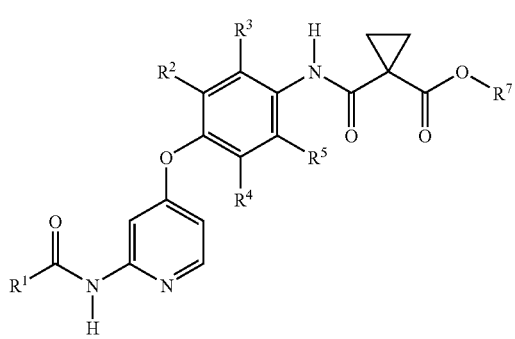

wherein $R^1$, $R^2$, $R^3$, $R^4$ and $R^5$ have the same definitions as defined in claim 1, and $R^7$ has the same definition as defined in claim 2, is prepared by reacting a compound represented by the formula (V):

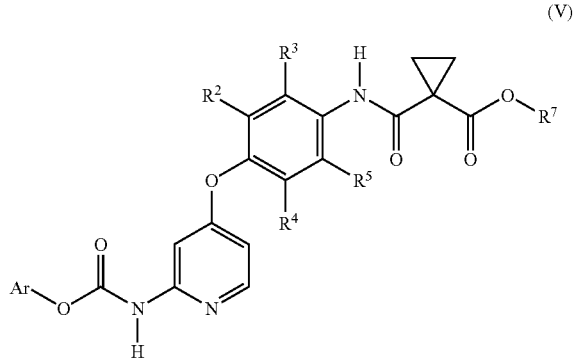

wherein $R^2$, $R^3$, $R^4$ and $R^5$ have the same definitions as defined in claim 1, $R^7$ has the same definition as defined in claim 2, and Ar represents phenyl optionally substituted with one or two substituents selected from halogen, methyl, methoxy, nitro, cyano and trifluoromethyl, with an amine or salt thereof selected from 1) azetidine optionally substituted with a substituent selected from Substituent Group A in claim 1, 2) pyrrolidine optionally substituted with a substituent selected from Substituent Group A in claim 1, 3) piperidine optionally substituted with a substituent selected from Substituent Group A in claim 1, 4) piperazine optionally substituted with a substituent selected from Substituent Group A in claim 1, 5) diazepane optionally substituted with a substituent selected from Substituent Group A in claim 1, 6) morpholine optionally substituted with a substituent selected from Substituent Group A in claim 1, or 7) $HNR^{11a}R^{11b}$, wherein $R^{11a}$ and $R^{11b}$ have the same definitions as defined in claim 1.

4. The process according to claim 3, wherein the compound represented by the formula (V):

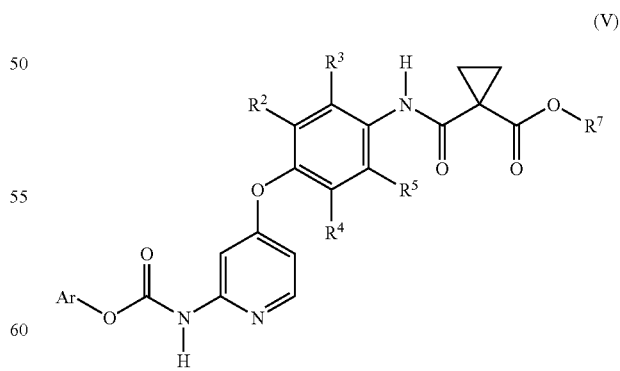

wherein $R^2$, $R^3$, $R^4$ and $R^5$ have the same definitions as defined in claim 1, $R^7$ has the same definition as defined in claim 2, and Ar has the same definition as defined in claim 3, is prepared by reacting a compound represented by the formula (VI):

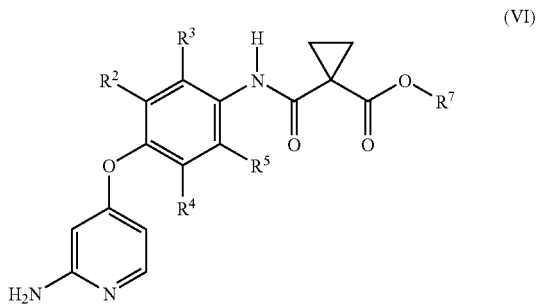

wherein $R^2$, $R^3$, $R^4$ and $R^5$ have the same definitions as defined in claim 1, and $R^7$ has the same definition as defined in claim 2, with a compound represented by the formula (VII):

wherein Ar has the same definition as defined in claim 3, in the presence of a base.

5. The process according to claim 4, wherein the compound represented by the formula (VI):

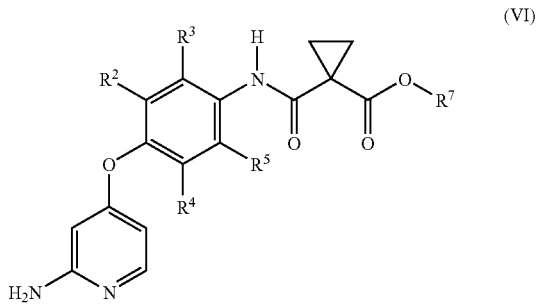

wherein $R^2$, $R^3$, $R^4$ and $R^5$ have the same definitions as defined in claim 1, and $R^7$ has the same definition as defined in claim 2, is prepared by reacting a compound represented by the formula (VIII):

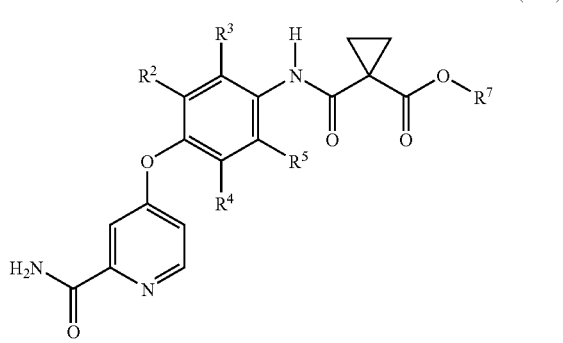

wherein $R^2$, $R^3$, $R^4$ and $R^5$ have the same definitions as defined in claim 1, and $R^7$ has the same definition as defined in claim 2, with a Hofmann rearrangement reagent.

6. The process according to claim 5, wherein the compound represented by the formula (VIII):

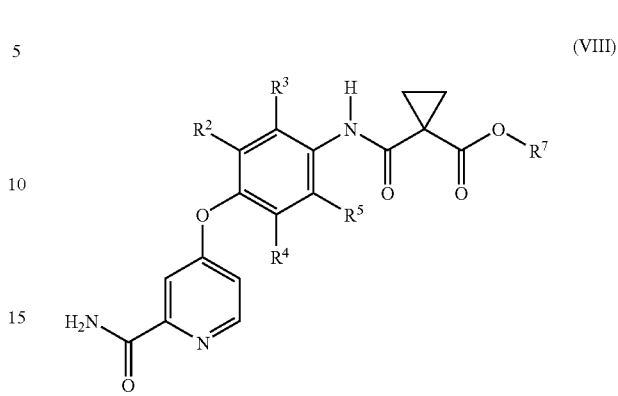

wherein $R^2$, $R^3$, $R^4$ and $R^5$ have the same definitions as defined in claim 1, and $R^7$ has the same definition as defined in claim 2, is prepared by reacting a compound represented by the formula (IX):

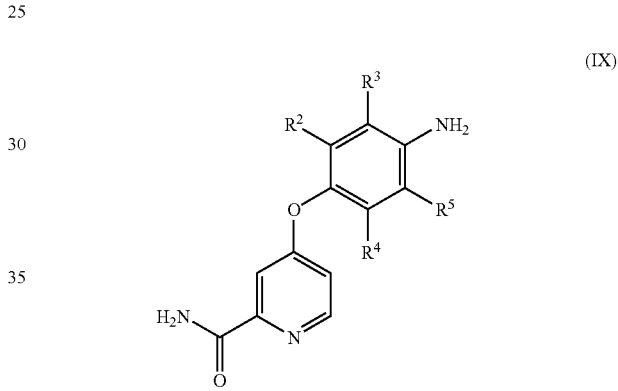

wherein $R^2$, $R^3$, $R^4$ and $R^5$ have the same definitions as defined in claim 1, with a compound represented by the formula (X):

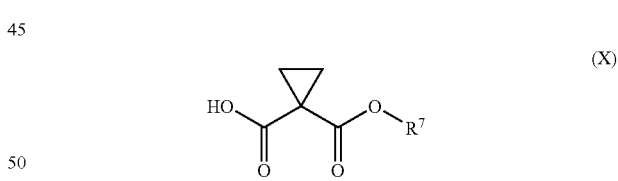

wherein $R^7$ has the same definition as defined in claim 2, in the presence of a halogenation regent or a condensation reagent.

7. The process according to claim 1, wherein the condensation reagent is 4-(4,6-dimethoxy[1.3.5]triazin-2-yl)-4-methylmorpholinium chloride hydrate or 2-chloro-4,6-dimethoxy-1,3,5-triazine.

8. The process according to claim 3, wherein the amine is 1-(2-dimethylaminoethyl)piperazine, 4-(pyrrolidin-1-yl)piperidine, 4-(dimethylaminomethyl)piperidine, 4-(azetidin-1-yl)piperidine, N,N-dimethyl-N-[1-(piperidin-4-yl)azetidin-3-yl]amine, 1-methyl-4-(piperidin-4-yl)piperazine, 4-(1-methylpiperidin-4-yl)piperazine, 1-(1-methylazetidin-3-yl) piperazine, 4-(dimethylamino)piperidine, 4-(azetidin-1-ylmethyl)piperidine, 4-(pyrrolidin-1-ylmethyl)piperidine, (3S)-3-(dimethylamino)pyrrolidine, (3R)-3-(dimethylamino)pyrrolidine, azetidine, pyrrolidine, morpholine, 1-methylpiperazine, 3-hydroxyazetidine, 3-(azetidin-1-yl)azetidine, 3-(hydroxymethyl)azetidine, 3-(dimethylamino)azetidine, 3-(dimethylaminomethyl)azetidine, 4-hydroxypiperidine, 4-(hydroxymethyl)piperidine, (3R)-3-hydroxypyrrolidine, (3S)-3-hydroxypyrrolidine, 3-(azetidin-1-ylmethyl)azetidine, 3-(2-dimethylaminoacetoxy)azetidine, 1-methyl-4-(methylamino)piperidine, N-(1-ethylpiperidin-4-yl)-N-methylamine, N,N-dimethyl-N'-methylpropane-1,3-diamine or N,N-diethyl-N'-methylpropane-1,3-diamine.

9. The process according to claim 5, wherein the Hofmann rearrangement reagent is iodobenzene diacetate or iodobenzene bis(trifluoroacetate).

10. The process according to claim 1, wherein $R^1$ is 4-[2-(dimethylamino)ethyl]piperazin-1-yl, 4-pyrrolidin-1-ylpiperidin-1-yl, 4-[(dimethylamino)methyl]piperidin-1-yl, 4-azetidin-1-ylpiperidin-1-yl, 4-[3-(dimethylamino)azetidin-1-yl]piperidin-1-yl, 4-(4-methylpiperazin-1-yl)piperidin-1-yl, 4-(1-methylpiperidin-4-yl)piperazin-1-yl, 4-(1-methylazetidin-3-yl)piperazin-1-yl, 4-(dimethylamino)piperidin-1-yl, 4-(azetidin-1-ylmethyl)piperidin-1-yl, 4-(pyrrolidin-1-ylmethyl)piperidin-1-yl, (3S)-3-(dimethylamino)pyrrolidin-1-yl, (3R)-3-(dimethylamino)pyrrolidin-1-yl, azetidin-1-yl, pyrrolidin-1-yl, morpholin-4-yl, 4-methylpiperazin-1-yl, 3-hydroxyazetidin-1-yl, 1,3'-biazetidin-1'-yl, 3-hydroxymethyl)azetidin-1-yl, 3-(dimethylamino)azetidin-1-yl, 3-[(dimethylamino)methyl]azetidin-1-yl, 4-hydroxypiperidin-1-yl, 4-hydroxymethyl)piperidin-1-yl, (3R)-3-hydroxypyrrolidin-1-yl, (3S)-3-hydroxypyrrolidin-1-yl, 3-(azetidin-1-ylmethyl)azetidin-1-yl, 3-(2-dimethylaminoacetoxy)azetidin-1-yl, methyl(1-methylpiperidin-4-yl)amino, (1-ethylpiperidin-4-yl)(methyl)amino, [3-(dimethylamino)propyl](methyl)amino or [3-(diethylamino)propyl](methyl)amino.

11. The process according to claim 1, wherein the group represented by the formula:

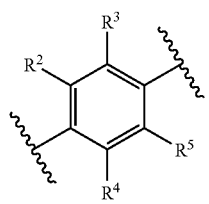

is a group represented by the formula:

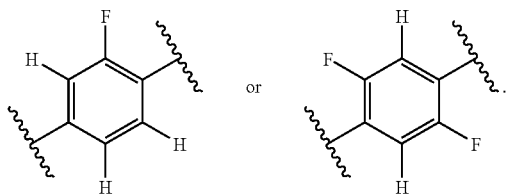

12. The process according to claim 2, wherein $R^7$ is benzyl.

13. A compound represented by the formula (IV-1) or salt thereof:

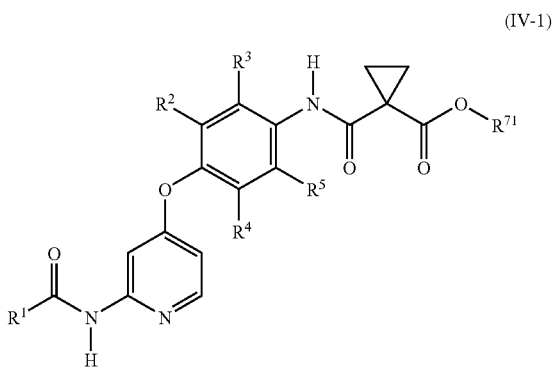

(IV-1)

wherein $R^1$ represents 1) azetidin-1-yl optionally substituted with a substituent selected from Substituent Group A, 2) pyrrolidin-1-yl optionally substituted with a substituent selected from Substituent Group A, 3) piperazin-1-yl optionally substituted with a substituent selected from Substituent Group A, 4) piperazin-1-yl optionally substituted with a substituent selected from Substituent Group A, 5) diazepan-1-yl optionally substituted with a substituent selected from Substituent Group A, 6) morpholin-4-yl optionally substituted with a substituent selected from Substituent Group A, or 7) $-NR^{11a}R^{11b}$, wherein $R^{11a}$ represents hydrogen or methyl, and $R^{11b}$ represents n-propyl, n-butyl, piperidin-3-yl, piperidin-4-yl or tetrahydropyran-4-yl, and $R^{11b}$ may be substituted with a substituent selected from Substituent Group B;

$R^2$, $R^3$, $R^4$ and $R^5$ may be the same or different and each represents hydrogen or fluorine;

$R^{71}$ represents hydrogen, $C_{1-6}$-alkyl or benzyl optionally substituted with one or two substituents selected from (1) halogen, (2) hydroxyl, (3) nitro, (4) cyano, (5) trifluoromethyl, (6) $C_{1-6}$ alkyl, (7) $C_{1-6}$ alkoxy, (8) amino, (9) mono-$C_{1-6}$ alkylamino and (10) di-$C_{1-6}$ alkylamino on the benzene ring;

Substituent Group A consists of hydroxyl, dimethylaminoacetoxy, methyl, ethyl, dimethylamino, azetidinyl, pyrrolidinyl, piperidinyl and piperazinyl, where each group included in Substituent Group A other than hydroxyl and dimethylaminoacetoxy may be substituted with hydroxyl, methyl, dimethylamino, azetidinyl, pyrrolidinyl or piperidinyl; and Substituent Group B consists of methyl, ethyl, n-propyl, acetyl, dimethylamino, diethylamino, azetidinyl, pyrrolidinyl and piperazinyl, where each group included in Substituent Group B may be substituted with methyl or dimethylamino.

14. A compound represented by the formula (V) or salt thereof:

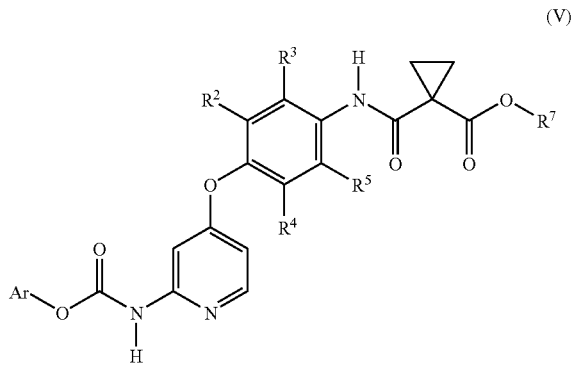

(V)

wherein $R^2$, $R^3$, $R^4$ and $R^5$ have the same definitions as defined in claim 13;

$R^7$ represents $C_{1-6}$ alkyl or benzyl optionally substituted with one or two substituents selected from (1) halogen, (2) hydroxyl, (3) nitro, (4) cyano, (5) trifluoromethyl, (6) $C_{1-6}$ alkyl, (7) $C_{1-6}$ alkoxy, (8) amino, (9) mono-$C_{1-6}$ alkylamino and (10) di-$C_{1-6}$ alkylamino on the benzene ring; and Ar represents phenyl optionally substituted with one or two substituents selected from halogen, methyl, methoxy, nitro, cyano and triflouromethyl.

15. A compound represented by the formula (VI) or salt thereof:

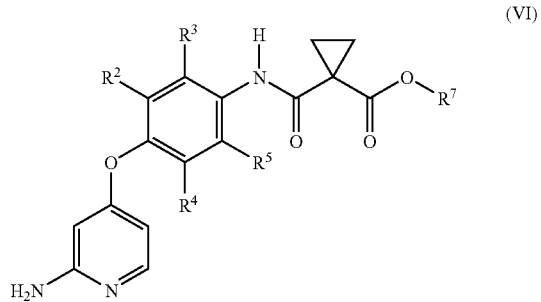

(VI)

wherein $R^2$, $R^3$, $R^4$ and $R^5$ have the same definitions as defined in claim 13, and $R^7$ has the same definition as defined in claim 14.

16. A compound represented by the formula (VIII) or salt thereof:

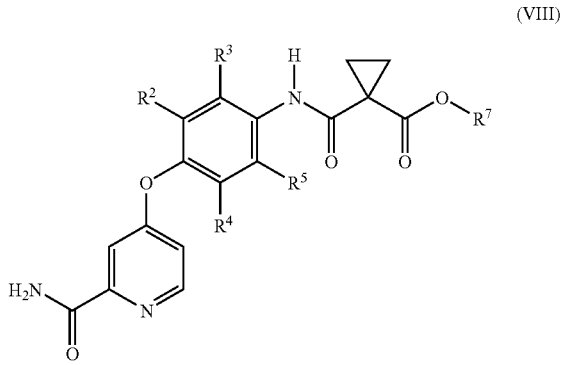

(VIII)

wherein $R^2$, $R^3$, $R^4$ and $R^5$ have the same definitions as defined in claim 13, and $R^7$ has the same definition as defined in claim 14.

17. The compound or salt thereof according to claim 13, wherein $R^1$ is 4-[2-(dimethylamino)ethyl]piperazin-1-yl, 4-pyrrolidin-1-ylpiperidin-1-yl, 4-[(dimethylamino)methyl]piperidin-1-yl, 4-azetidin-1-ylpiperidin-1-yl, 4-[3-(dimethylamino)azetidin-1-yl]piperidin-1-yl, 4-(4-methylpiperazin-1-yl)piperidin-1-yl, 4-(1-methylpiperidin-4-yl)piperazin-1-yl, 4-(1-methylazetidin-3-yl)piperazin-1-yl, 4-(dimethylamino)piperidin-1-yl, 4-(azetidin-1-ylmethyl)piperidin-1-yl, 4-(pyrrolidin-1-ylmethyl)piperidin-1-yl, (3S)-3-(dimethylamino)pyrrolidin-1-yl, (3R)-3-(dimethylamino)pyrrolidin-1-yl, azetidin-1-yl, pyrrolidin-1-yl, morpholin-4-yl, 4-methylpiperazin-1-yl, 3-hydroxyazetidin-1-yl, 1,3'-biazetidin-1'-yl, 3-(hydroxymethyl)azetidin-1-yl, 3-(dimethylamino)azetidin-1-yl, 3-[(dimethylamino)methyl]azetidin-1-yl, 4-hydroxypiperidin-1-yl, 4-(hydroxymethyl)piperidin-1-yl, (3R)-3-hydroxypyrrolidin-1-yl, (3S)-3-hydroxypyrrolidin-1-yl, 3-(azetidin-1-ylmethyl)azetidin-1-yl, 3-(2-dimethylaminoacetoxy)azetidin-1-yl, methyl(1-methylpiperidin-4-yl)amino, (1-ethylpiperidin-4-yl)(methyl)amino, [3-(dimethylamino)propyl](methyl)amino or [3-(diethylamino)propyl](methyl)amino.

18. The compound or salt thereof according to claim 13, wherein the group represented by the formula:

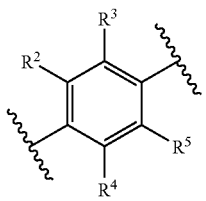

is a group represented by the formula:

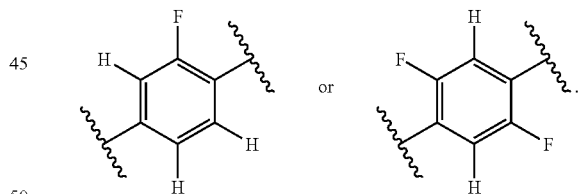

19. The compound or salt thereof according to claim 14, wherein $R^7$ is benzyl.

20. A Crystal of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide.

21. The crystal according to claim 20, having diffraction peaks at diffraction angles (2θ±0.2°) of 6.3°, 12.3° and 17.3° in a powder X-ray diffraction.

22. The process according to claim 6, wherein the condensation reagent is 4-(4,6-dimethoxy[1.3.5]triazin-2-yl)-4-methylmorpholinium chloride hydrate or 2-chloro-4,6-dimethoxy-1,3,5-triazine.

* * * * *